(12) United States Patent
Kakish et al.

(10) Patent No.: US 11,634,434 B2
(45) Date of Patent: Apr. 25, 2023

(54) BIFUNCTIONAL ALPHA-SYNUCLEIN BINDING AGENTS AND USES THEREOF

(71) Applicant: University of Saskatchewan, Saskatoon (CA)

(72) Inventors: Joseph Kakish, Saskatoon (CA); Edward Krol, Saskatoon (CA); Jeremy Lee, Saskatoon (CA); Kevin Allen, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 43 days.

(21) Appl. No.: 16/328,250

(22) PCT Filed: Sep. 8, 2017

(86) PCT No.: PCT/CA2017/051053
§ 371 (c)(1),
(2) Date: Feb. 25, 2019

(87) PCT Pub. No.: WO2018/045464
PCT Pub. Date: Mar. 15, 2018

(65) Prior Publication Data
US 2020/0062782 A1 Feb. 27, 2020

Related U.S. Application Data

(60) Provisional application No. 62/385,168, filed on Sep. 8, 2016.

(51) Int. Cl.
*C07D 519/00* (2006.01)
*A61K 51/04* (2006.01)
*C07D 473/12* (2006.01)

(52) U.S. Cl.
CPC ........ *C07D 519/00* (2013.01); *A61K 51/0459* (2013.01); *C07D 473/12* (2013.01)

(58) Field of Classification Search
None
See application file for complete search history.

(56) References Cited

FOREIGN PATENT DOCUMENTS

| WO | 96/21640 A2 | 7/1996 |
|---|---|---|
| WO | 2008/154083 A2 | 12/2008 |
| WO | 2010/036821 A1 | 4/2010 |

OTHER PUBLICATIONS

Sabitha et al. Finding new inhibitors for EML4-ALK fusion protein: a computational approach. 2012 IRJP 3: 171-176. (Year: 2012).*
Bertrand et al. Caffeine-based gold(I) N-heterocyclic carbenes as possible anticancer agents: synthesis and biological properties. 2014 Inorg. Chem. 53: 2296-2303. (Year: 2014).*
Shulman, J.M., De Jager, P.L., and Feany, M.B. (2011). Parkinson's Disease: Genetics and Pathogenesis. Annu, Rev. Pathol. 6, 193-222.
Stefureac, R., Long, Y.T., Kraatz, H.B., Howard, P. and Lee, J. S. (2006) Transport of alpha-helical peptides through alpha-hemolysin and aerolysin pores. Biochemistry 45, 9172-9179.
Stefureac, R.I. and Lee, J.S. (2008) Nanopore analysis of the folding of zinc fingers. Small 4, 1646-50.
Su, L. J., Auluck, P. K., Outeiro, T. F., Yeger-Lotem, E., Kritzer, J. A., Tardiff, D. F., Strathearn, K. E., Liu, F., Cao, S., Hamamichi, S., Hill, K. J., Caldwell, K. A., Bell, G. W., Fraenkel, E., Cooper, A. A., Caldwell, G. A., McCaffery, J. M., Rochet, J. C., and Lindquist, S. (2010) Compounds from an unbiased chemical screen reverse both ER-to-Golgi trafficking defects and mitochondrial dysfunction in Parkinson's disease models. Dis. Model Mech. 3, 194-208.
Tardiff, L., Jui, N. T., Khurana, V., Tambe, M. A., Thompson, M. L., Chung, C. Y., Kamadurai, H. B., Kim, H. T., Lancaster, A. K., Caldwell, K. A., Caldwell, G. A., Rochet, J-C., Buchwald, S. L. and Lindquist, S. (2013) Yeast reveal a druggable Rsp/Nedd4 network that ameliorates a-synuclein toxicity. Science 342, 979-983.
Tavassoly et al., "The use of nanopore analysis for discovering durgs which bind to α-synuclein for treatment of Parkinson's diseas", European Journal of Medicinal Chemistry 88 (2014) 42-54.
Tavassoly, O., Nokhrin, S., Dmitriev, O.Y., and Lee, J. S., (2014) Cu(II) and dopamine bind to alpha-Synuclein and cause large conformational changes, FEBS J. 281, 2738-2753.
Turner, E. L., Malo, M. E., Pisclevich, M. G., Dash, M. D., Davies, G. F., Amason, T. G., and Harkness, T. A. (2010) The *Saccharomyces cerevisiae* anaphase promoting complex interacts with multiple histone modifying enzymes to regulate cell cycle progression. Eukaryot. Cell 9, 1418-1431.
Uversky, V. N. (2008) Alpha-synuclein misfolding and neurodegenerative diseases. Curr. Protein Pept. Sci. 9, 507-540.
Wahlqvist, M. L., Lee, M-S., Hsu, C-C., Chuang, S-Y., Lee, J-T., and Tsai, H-N. (2012) Metformin-inclusive sulfonylurea therapy reduces the risk of Parkinson's disease occurring with Type 2 diabetes in a Taiwanese population cohort. Park. Rel. Dis. 18, 753-758.
Wang, A., Costello, S., Cockburn, M., Zhang, X., Bronstein, J., and Ritz, B. (2011) Parkinson's risk from ambient exposure to pesticides. Eur. J. Epidemiol. 26, 547-555.
Youle, R. J., and Nerendra, D. P. (2011) Mechanisms of Mitophagy. Nat. Rev. Mol. Cell Biol. 12, 9-14.
Zhao, Q., Jayawardhana, D.A., Wang, D. and Guan, X. (2009) Study of peptide transport through engineered protein channels. J. Phys. Chem. B 113, 3572-8.
Abelaira et al., Animal Models as Tools to Study the Pathophysiology of Depression. Revista Brasileira de Psiquiatria, 2013, 35(Suppl. 2), pp. S112-S120.
Chu et al., Design, Synthesis, and Characterization of 3-(Benzylidene)inodlin-2-one Derivatives as Lingands for alpha-Synuclein Fibrils. Journal of Medicinal Chemistry 2015, 58 (15), 6002-6017.
Kakish et al., Novel Dimer Compounds That Bind α-Synuclein Can Rescue Cell Growth in a Yeast Model Overexpressing α-Synuclein. A Possible Prevention Strategy for Parkinson's Disease. ACS Chemical Neuroscience 2016, 7, 1671-1680.

(Continued)

*Primary Examiner* — Jennifer Lamberski
(74) *Attorney, Agent, or Firm* — Oyen Wiggs Green & Mutala LLP

(57) ABSTRACT

Bifunctional molecules having first and second alpha-synuclein binding agents coupled by a linker are disclosed. The bifunctional molecules have potential utility in the diagnosis, treatment and/or prophylaxis of disorders in which alpha-synuclein is implicated, including Parkinson's disease. Methods of making and using the bifunctional molecules are disclosed.

9 Claims, 28 Drawing Sheets

(56) References Cited

OTHER PUBLICATIONS

Bar Am, O., Amit, T., and Youdim, M. B. H. (2004) Contrasting neuroprotective and neurotoxic actions of respective metabolites of anti-Parkinson drugs rasagiline and selegiline. Neurosci. Lett. 355, 169-172.

Bar-Am, O., Weinreb, O., Amit, T., and Youdim, M. B. H. (2010) The neuroprotective mechanism of 1-[R]-aminoindan, the major metabolite of the anti parkinsonian drug rasagiline. J. Neurochem. 112, 1131-1137.

Binolfi, A., Quintanar, L., Bertoncini, C.W., Griesinger, C., and Fernández, C.O. (2012). Bioinorganic chemistry of copper coordination to alpha-synuclein: Relevance to Parkinson's disease. Coord. Chem. Rev. 256, 2188-2201.

Burré, J., Sharma, M., and Sudhof, T.C. (2012). Systematic Mutagenesis of α-Synuclein Reveals Distinct Sequence Requirements for Physiological and Pathological Activities. J. Neurosci. 32, 15227-15242.

Callaghan, R.C., Cunningham, J. K., Sykes, J., and Kish, S.J. (2012) Increased risk of Parkinson's disease in individuals hospitalized with conditions related to the use of methamphetamine or other amphetamine-type drugs. Drug Alcohol Depend. 146, 30-38.

Chau, K. Y., Cooper, J. M., and Schapira, A. H. V. (2010) Rasagiline protects against alpha-synuclein induced sensitivity to oxidative stress in dopaminergic cells. Neurochem. Int. 57, 525-529.

Curtin, K., Fleckenstein, A. E., Robison, R. J., Crookston, M. J., Smith, K. R. and Hanson, G. R. (2015) Methamphetamine/ amphetamine abuse and risk of Parkinson's disease in Utah: a population-based assessment. Drug Alcohol Depend. 120, 35-40.

Davie, C. A. (2008) A review of Parkinson's disease. Br. Med. Bull. 86, 109-127.

Dimpfel, W., and Hoffmann, J. A. (2011) Effects of rasagiline, its metabolite aminoindan and selegiline on glutamate receptor mediated signaling in the rat hippocampus slice in vitro. BMC Pharmacology 11, 1-10.

Dufty, B., Warner, L., Hou, S., Jiang, S., Gomez-Isla, T., Leenhouts, K., Oxford, J., Feany, M., Masliah, E., and Rohn, T. (2007). Calpain-Cleavage of a-Synuclein: Connecting Proteolytic Processng to Disease-Linked Aggregation. Am. J. Pathol. 170, 1725-1738.

Feany, M. B., and Pallanck, L. J. (2003) Parkin: A Multipurpose Neuroprotective Agent? Neuron 38, 13-16.

Fink, A.L. (2006). The Aggregation and Fibrillation of α-Synuclein. Acc. Chem. Res. 39, 628-634.

Forno, L. S. (1996) Neuropathology of Parkinson's disease. J. Neuropathol. Exp. Neurol. 55, 259-272.

Games, D., Valera, E., Spencer, B., Rockenstein, E., Mante, M., Adame, A., Patrick, C., Ubhi, K., Nuber, S., Sacayon, P., Zago, W., Seubert, P., Barbour, R., Schenk, D., and Masliah, E. (2014). Reducing C-Terminal-Truncated Alpha-Synuclein by Immunotherapy Attenuates Neurodegeneration and Propagation in Parkinson's Disease-Like Models. J. Neurosci. 34, 9441-9454.

Georgieva, E.R., Ramlall, T.F., Borbat, P.P., Freed, J.H., and Eliezer, D. (2010). The Lipid-binding Domain of Wild Type and Mutant α-Synuclein: Compactness and interconversion between the broken and extended helix forms. J. Biol. Chem. 285, 28261-28274.

Ghavidel, A., Baxi, K., Ignatchenko, V., Prusinkiewics, M., Arnason, T. G., Kislinger, T., Carvalho, C. E., and Harkness, T. A. (2015) A genome scale screen for mutants with delayed exit from mitosis: Ire1-independent induction of autophagy integrates ER homeostasis into mitotic lifespan. PloS Genet. 11, e1005429.

Grosset, D.G., Grosset, K.A., Okun, M.S., and Fernandez, H.H. (2009). Drug treatment of Parkinson's disease. In Parkinson's Disease : Clinician's Desk Reference, Grosset, D.G., Grosset, K.A., Okun, M.S., and Fernandez, H.H., eds. (London: Manson Publishing Ltd), pp. 59-68.

Hu, R., Diao, J., Li, J., Tang, Z., Li, X., Leitz, J., Long, J., Liu, J., Yu, D., and Zhao, Q. (2016) Intrinsic and membrane-facilitated a-synuclein oligomerization revealed by label-free detection through solid-state nanopores. Sci. Rep. 6, 1-11.

J. Charlton, "Can "caffeitine" treat Parkinson's?". University of Saskatchewan, http://www.usask.ca/pharmacy-nutrition/news/2014/can-caffeitine-treat-parkinsons.php. Accessed Aug. 18, 2016.

J. Lee, and E. Krol, "New Drugs for Treatment of Parkinson's Disease". University of Saskatchewan, Creativity Commercialized, Industry liaison Office. Available at least as early as Sep. 7, 2016.

J. Schappi, "Aging and Parkinson's and Me: Caffeine and Nicotine Together: Powerful One-Two Parkin's Punch?". http://parkinsonsand5htp.blogspot.ca/2014/04/caffeine-and-nicotine-together-powerful.html. Accessed Aug. 18, 2016.

Jucker, M., and Walker, L. C. (2013) Self-propagation of pathogenic protein aggregates in neurodegenerative diseases. Nature 501, 45-51.

Kakish, J., Lee, D., and Lee, J. S. (2015) Drugs that bind to alpha-synuclein: Neuroprotective or neurotoxic? ACS Chem. Neurosci. 6, 1930-1940.

Kakish, J., Tavassoly, O., and Lee, J. S. (2015). Rasagiline, a suicide inhibitor of MAO-B, binds to alpha-synuclein. ACS Chem. Neurosci. 6, 347-355.

Kalla, R. V., Elzein, E., Perry, T., Li, X., Palle, V., Varkhedkar, V., Gimbel, A., Maa, T., Zeng, D., and Zablocki, J. (2006) Novel 1,3-Disubstituted 8-(1-benzyl-1H-pyrazol-4-yl) Xanthines: High Affinity and Selective A2B Adenosine Receptor Antagonists. J. Med. Chem. 49, 3682-3692.

Kamel, F. (2013) Paths from pesticides to Parkinson's. Science 341, 722-723.

Khurana, V., and Lindquist, S. (2010) Modeling neurodegeneration in *Saccharomyces cerevisiae*. Why cook with baker's yeast? Nat. Rev. Neurosci. 11, 436-449.

Klein, C., and Westenberger, A. (2012) Genetics of Parkinson's Disease. Cold Spring Harb. Perspect. Med. 2: a008888, 1-15.

Kraus, A., Groveman, B. R., and Caughey, B. (2013) Prions and the potential transmissability of protein misfolding diseases. Annu. Rev. Microbiol. 67, 543-564.

Kuter, K., Nowak, P., Golembiowska, K., and Ossowska, K. (2010) Increased reactive oxygen species production in the brain after repeated low-dose pesticide paraquat exposure in rats. A comparison with peripheral tissues. Neurochem. Res. 35, 1121-1130.

Lashuel, H.A., Overk, C.R., Oueslati, A., and Masliah, E. (2013). The many faces of [alpha]-synuclein: from structure and toxicity to therapeutic target. Nat. Rev. Neurosci. 14, 38-48.

Le Quement, S. T., Nielsen, T. E., and Meldal, M. (2007) Scaffold Diversity through Intramolecular Cascade Reactions of Solid-Supported Cyclic N-Acyliminium Intermediates. J. Comb. Chem. 9 (6), 1060-1072.

Lee, "Development of Drugs which Bind to α-Synuclein for treatment of Parkinson's Disease". Recipients, http://shrf.ca/Recipient?recipID=3638. Accessed Aug. 18, 2016.

Lotharius, J., and Brundin, P. (2002). Pathogenesis of Parkinson's disease: dopamine, vesicles and [alpha]-synuclein. Nat. Rev. Neurosci. 3, 932-942.

Luk, K. C., Kehm, V., Carroll, J., Zhang, B., O'Brien, P., Trojanowski, J. Q., and Lee, V. M.-Y. (2012) Pathological alpha-synuclein transmission initiates Parkinson-like neurodegeneration in nontransgenic mice. Science 338, 949-953.

Madampage, C., Tavassoly, O., Christensen, C., Kumari, M. and Lee, J. S. (2012) Nanopore analysis: An emerging technique for studying the folding and misfolding of proteins. Prion 6, 116-123.

Movileanu, L., Schmittschmitt, J.P., Scholtz, J.M. and Bayley, H. (2005) Interactions of peptides with a protein pore. Biophys. J. 89, 1030-45.

Outeiro TF, Lindquist S (2003) Yeast cells provide insight into alpha-synuclein biology and pathobiology. Science 302, 1772-1775.

Patil, S. P., Jain, P. D., Ghumatkar, P. J., Tambe, R., and Sathaye, S. (2014) Neuroprotective effect of metformin in MPTP-induced Parkinson's disease in mice. Neurosci, 277, 747-754.

Postuma, R. B., Lang, A. E., Munhoz, R.P., Charland, K., Pelletier, A., Moscovich, M., Filla, L., Zanatta, D., Romenets, S. R., Altman, R., and Chuang, R., (2012) Caffeine for treatment of Parkinson disease: A randomized controlled trial. Neurobiology, 79, 651-658.

Prediger, R.D. (2010) Effects of caffeine in Parkinson's disease: from neuroprotection to the management of motor and non-motor symptoms. J Alzheimers Dis. 20, 205-220.

(56) References Cited

OTHER PUBLICATIONS

Prusiner, S. B. (2012) A unifying role for prions in neurodegenerative diseases. Science 336, 1511-1513.
Qian et al., "Cucurbituril-Modulated Supramolecular Assemblies: From Cyclic Oligomers to Linear Polymers", Chem. Eur. J., 2012, 18, pp. 5087-5095.
Quik, M. (2004) Smoking, nicotine and Parkinson's disease. Trends Neurosci. 27, 561-568.
Quik, M., Perez, X.A., and Bordia, T. (2012) Nicotine as a potential neuroprotective agent for Parkinson's disease. Mov. Disord. 27, 947-957.
Ross, G.W., and Petrovitch, H. (2001) Current evidence for neuroprotective effects of nicotine and caffeine against Parkinson's disease. Drugs Aging, 18, 797-806.
Samii, A., Nutt, J. G., and Ransom, B. R. (2004) Parkinson's disease. Lancet 363, 1783-1789.
Fuchs et al., "Uber die Cyclisierung von 4-Alkylamino-5-nitrosouracilen und die Synthese von 8-substituierten Xanthinen und Bis(theophylline-8-yl)-alkan-Derivaten", Chem. Ber., 1978, 111, pp. 982-995.
Yoneda et al., "A Novel Synthesis of Theophylline Derivatives", J. Het. Chem., Jul.-Aug. 1982, 19, pp. 813-816.

\* cited by examiner

* P < 0.05
*** P < 0.001

Vehicle Control (DMSO/Saline)

ASIA

ASIA + C-I (3 mg/kg)

ASIA + C-I (5 mg/kg)

*P < 0.05
**P < 0.01
***P < 0.001

BIFUNCTIONAL ALPHA-SYNUCLEIN BINDING AGENTS AND USES THEREOF

REFERENCE TO RELATED APPLICATIONS

This application is a national phase entry of Patent Cooperation Treaty patent application No. PCT/CA2017/051053 filed 8 Sep. 2017, which claims priority to and the benefit of U.S. provisional patent application No. 62/385,168 filed 8 Sep. 2016. Both of the foregoing applications are incorporated by reference herein in their entireties for all purposes.

TECHNICAL FIELD

Some embodiments of the present invention pertain to compounds that bind to alpha-synuclein. Some embodiments of the present invention pertain to compounds that bind to alpha-synuclein with increased affinity. Some embodiments of the present invention pertain to compounds that bind to alpha-synuclein in a way that reduces aggregation of alpha-synuclein, in vitro and/or in vivo. Some embodiments of the present invention may have potential utility as therapeutic agents in PET scanning. Some embodiments of the present invention may have potential utility as diagnostic agents for Parkinson's disease. Some embodiments of the present invention may have potential utility as therapeutic agents in the prophylaxis and/or treatment of Parkinson's disease.

BACKGROUND

A characteristic pathogenic feature of Parkinson's Disease (PD) is the aggregation of alpha-synuclein (AS) into fibrils and inclusions known as Lewy bodies.[1-4] Alpha-synuclein is a natively unfolded or intrinsically disordered protein whose structure is extremely sensitive to its environment. For example, in the presence of anionic phospholipids an alpha-helix is formed in the N-terminal region, which may relate to the role of alpha-synuclein in synaptic vesicle trafficking.[5-8] In contrast, some divalent metal ions such as Cu(II) cause the protein to aggregate through beta-sheet formation which is similar to the initial steps of fibrillization.[9-11]

Current therapies for Parkinson's Disease include the use of drugs such as levodopa or rasagiline which increase the levels of dopamine in the substantia nigra and can alleviate the typical symptoms of resting tremor and slow movement.[12] However, over a period of 5-10 years the disease inevitably progresses leading to further cell death in the substantia nigra and in other brain regions.[1,2,13]

There is good evidence that aggregated alpha-synuclein can act as a prion.[14-16] That is, it can be released from a dying cell and infect a healthy cell, explaining the progressive nature of the disease.[17] Even so, the cause of neuronal cell death in Parkinson's Disease is not well understood and it has been suggested that increasing the activity of the misfolded protein clearance machinery or decreasing the rate of mitophagy might provide improved therapies.[18-20] However, since the misfolding and aggregation of alpha-synuclein appears to be the key toxic event, an emerging therapeutic target is prevention of the initial step of the misfolding pathway.[21]

Epidemiological studies have revealed that the environment can play an important role in the development and incidence of Parkinson's Disease.[22-24] For example, ingestion of caffeine in coffee or nicotine in tobacco smoke decreases the incidence of the disease by as much as 50%.[25-29] Other drugs such as metformin, which is used to treat diabetes, and 1-aminoindan which is a metabolite of rasagiline, may also be neuroprotective.[30-35] Conversely, recreational amphetamine use causes a significant increase in the incidence of the disease as does exposure to some agricultural chemicals such as paraquat.[22-24,36,37]

Previously, the inventors demonstrated by nanopore analysis and isothermal titration calorimetry (ITC) that caffeine, nicotine, 1-aminoindan, metformin, amphetamine and paraquat all bind to alpha-synuclein.[21] However, their mode of interaction is different. Caffeine, nicotine and 1-aminoindan all bind to alpha-synuclein at both the N- and C-terminus and the ITC results show that there is a 1:1 ratio of drug to alpha-synuclein in the complex. Without being bound by theory, one explanation for these results is that the compounds force alpha-synuclein to adopt a loop conformation, as shown in FIG. 1 for methylphenidate (Ritalin™) (on the left hand side), versus amphetamine (on the right hand side), which causes alpha-synuclein to adopt a more compact conformation and is neurotoxic.[40] It has been hypothesized that a loop inhibits beta-sheet formation because beta-sheets require an extended linear structure for two strands to associate. Thus, it has been hypothesized that direct binding to alpha-synuclein may contribute to the neuroprotective activity of these drugs.[21]

The mode of binding of metformin is different since there is no interaction with the N-terminus. However, it is known that C-terminal cleavage of alpha-synuclein increases the rate of aggregation and exacerbates the neurodegeneration and propagation of Parkinson's Disease in mouse models.[38,39] Thus, the neuroprotective effect of metformin may be due to the inhibition of cleavage of the C-terminus. In contrast, amphetamine and paraquat cause alpha-synuclein to adopt a more compact conformation and they only bind to the N-terminus which may contribute to the neurotoxicity of these drugs.[21]

Although drugs such as caffeine and nicotine may provide some protection against progression of Parkinson's Disease, they are toxic at high doses. There remains a need for compounds and methods that may potentially protect against the progression of Parkinson's Disease, including compounds that may limit, delay and/or reverse the aggregation of alpha-synuclein.

Positron emission tomography (PET) scanning is an imaging technique that can be used to visualize processes occurring within the body. A positron-emitting radionuclide is introduced into the body on a biologically active molecule. In the case of Parkinson's Disease, given the correlation between alpha-synuclein and Parkinson's Disease, molecules that can bind to alpha-synuclein have potential utility as imaging agents in PET scanning if an appropriate label (e.g. $^{18}F$ or $^{11}C$) is incorporated into a molecule. There remains a need for diagnostic agents that can be used to help diagnose Parkinson's Disease, and in particular which may help to provide an early diagnosis of Parkinson's Disease.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect provides a bifunctional molecule with a first alpha-synuclein binding agent covalently linked to a second alpha-synuclein binding agent by a linker. The first and second alpha-synuclein binding agents can be the same alpha-synuclein binding agent or different alpha-synuclein binding agents.

In one aspect, the bifunctional molecule has the general structure

wherein A is an alpha-synuclein binding agent, B is an alpha-synuclein binding agent, and n is an integer between 1 and 10 that defines a linker, wherein A and B are optionally the same alpha-synuclein binding agents or different alpha-synuclein binding agents, wherein the linker is optionally saturated, unsaturated, alkylated, substituted, modified to include one or more heteroatoms, halogenated, or otherwise modified, and wherein A and B are optionally analogues, derivatives, modified, substituted or halogenated versions of the alpha-synuclein binding agents.

In one aspect, the bifunctional molecule is used as an imaging agent for conducting PET scanning or other similar diagnostic procedure.

In one aspect, a method of preventing or delaying the aggregation of alpha-synuclein is provided, and includes administering a bifunctional molecule as defined in this specification to a mammal. In one aspect, a method of preventing, delaying or slowing the onset of Parkinson's disease is provided, which includes administering a bifunctional molecule as defined in this specification to a mammal. In some aspects, the mammal is a human.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 4A shows wild-type (WT), 1AS (1 copy of AS-GFP gene), and 2AS (2 copies of AS-GFP gene). FIG. 4B shows toxicity of drugs on WT yeast. FIG. 4C shows 1 micromolar compound ("drug")+100 micromolar galactose with 2AS yeast.

FIG. 5A shows monomers and combinations of monomers at 1 micromolar compound ("drug")+5 mM galactose. FIG. 5B shows the synthesized bifunctional molecules at 1 micromolar compound ("drug")+5 mM galactose. FIG. 5C shows dimers and monomers at 0.1 micromolar+5 mM galactose. "Others" indicates the other tested bifunctional molecules and monomers, which did not allow for growth of the yeast. FIG. 5D shows compound ("drug") at 0.01 micromolar+5 mM galactose.

FIG. 12A shows the individual scores measured with time for each group for vigor. FIG. 12B contrasts the average results across the first three minutes with the average results across the last three minutes of the test for each group for vigor. FIG. 12C shows the individual scores measured with time for each group for success. FIG. 12D contrasts the average results across the first three minutes with the average results across the last three minutes of the test for each group for vigor. FIG. 12E shows the percentage of immobility, calculated based on the % of time that the rat is motionless.

FIG. 14A shows the individual scores measured with time for each group for vigor. FIG. 14B contrasts the average results across the first three minutes with the average results across the last three minutes of the test for each group for vigor. FIG. 14C shows the individual scores measured with time for each group for success. FIG. 14D contrasts the average results across the first three minutes with the average results across the last three minutes of the test for each group for vigor. FIG. 14E shows the percentage of immobility, calculated based on the % of time that the rat is motionless.

DESCRIPTION

Figure 1:
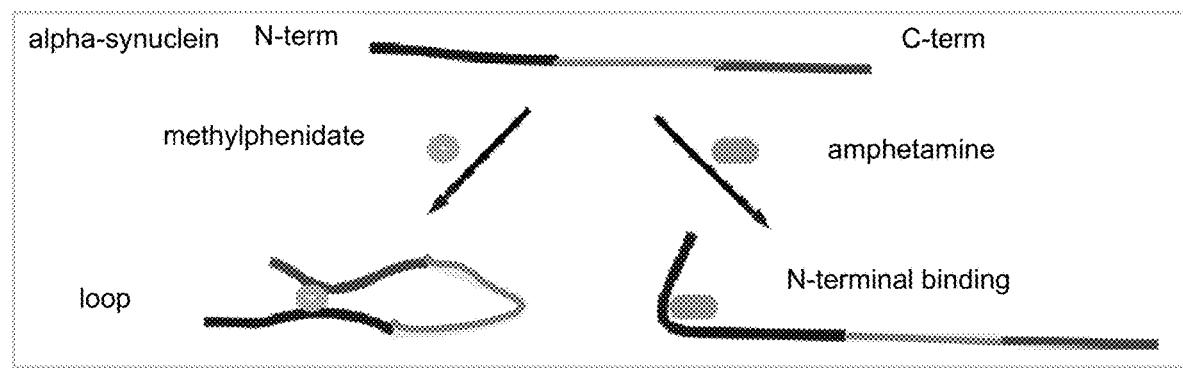
FIG. 1 shows predicted models of interaction of alpha-synuclein with methylphenidate (Ritalin™) and amphetamine.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

The inventors have now determined that structural modifications to compounds known to bind to alpha-synuclein may improve the likelihood that such compounds may be useful in the treatment of Parkinson's Disease, without necessarily increasing the toxicity of such compounds. The inventors have prepared bifunctional molecules comprising linked combinations of alpha-synuclein binding agents, and have demonstrated that the resulting bifunctional molecules can enhance growth and even in some embodiments cause the deaggregation of vacuolar inclusions in a yeast cell line which overexpresses alpha-synuclein under control of a galactose promoter. The inventors have further demonstrated that the resulting bifunctional molecules can prevent increased accumulation and/or aggregation of alpha-synuclein in a rat model in which alpha-synuclein expression is increased, and can increase the motor function of such rats, for example as evaluated by assessing the vigor and success of such rats in a forced swim test. Some embodiments of such bifunctional molecules also have potential utility as imaging agents, e.g. for use in PET scanning.

As used herein, "alpha-synuclein binding agent" means a compound that binds to alpha-synuclein. Examples of alpha-synuclein binding agents include caffeine, theophylline, theobromine, nicotine, metformin, 1-aminoindan (a derivative of rasagiline (Azilect™)), 2-aminoindan, curcumin, fluorinated-indans including 4-fluoro-1-aminoindan, amphetamine, methamphetamine, methylphenidate (Ritalin™), cocaine, paraquat, dopamine, 3-methoxydopamine, rotenone, as well as analogues of such compounds, for example, methylated analogues, ethylated analogues, and the like; halogenated analogues, including fluorinated analogues, including fluorinated analogues of nicotine, fluorinated analogues of caffeine, and as (Z)-1-(4-(2-fluoroethoxy)benzyl)-3-(E)-3-(4-nitrophenyl)-allylidene)indolin-2-one.[58]

As used herein "bifunctional molecule" means a molecule that comprises two linked alpha-synuclein binding agent molecules, wherein the alpha-synuclein binding agent molecules can be the same compound or different compounds. In some embodiments, bifunctional molecules in which the alpha-synuclein binding agent molecules are the same are referred to as a "dimer". In some embodiments, bifunctional molecules in which the alpha-synuclein binding agent molecules are different are referred to as a "chimera".

In some embodiments, a first alpha-synuclein binding agent and a second alpha-synuclein binding agent are covalently linked together to provide a bifunctional molecule. In some embodiments, the first and second alpha-synuclein binding agents are linked via a linker.

In some embodiments, the bifunctional molecule may be able to bind to two different sites on alpha-synuclein because its constituent first and second alpha-synuclein binding agents have different binding sites on alpha-synuclein. For example, it is known that caffeine and nicotine have different binding sites on alpha-synuclein.[40] Alternatively, in some embodiments, the bifunctional molecule may be able to bind to two different sites on alpha-synuclein because one or both of its constituent first and second alpha-synuclein binding agents can bind to two or more binding sites on alpha-synuclein. For example, some compounds such as caffeine, nicotine and 1-aminoindan themselves bind to two different binding sites on alpha-synuclein[21]. Thus, in some embodiments, a dimer composed of two such alpha-synuclein binding agents that bind to two different binding sites on alpha-synuclein can potentially bind to two or more different binding sites on alpha-synuclein.

In some embodiments, the first and second alpha-synuclein binding agents independently have one of the following structures (and in some embodiments may both be a same one of the following structures) (101), (102), (103), (104), (105), (106), (107), (108), (109), (110), (111), (112), (113), (114), (115), (116), or (117):

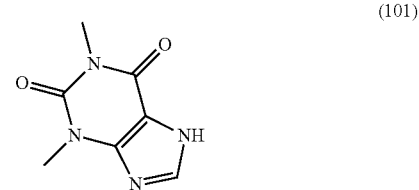

Theophylline (101)

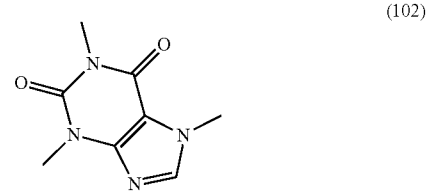

Caffeine (102)

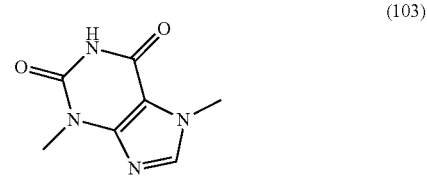

Theobromine (103)

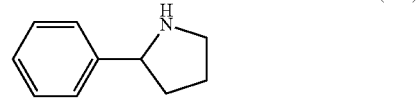

Nicotine (104)

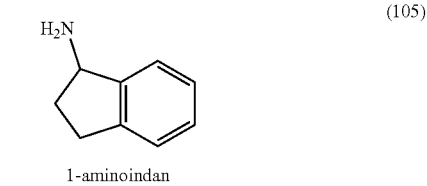

1-aminoindan (105)

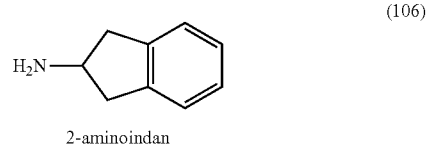

2-aminoindan (106)

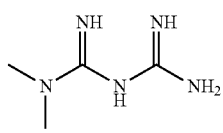

Metformin

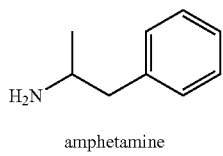

amphetamine

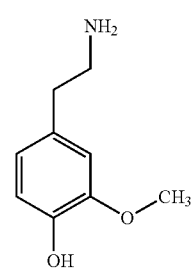

3-methoxydopamine

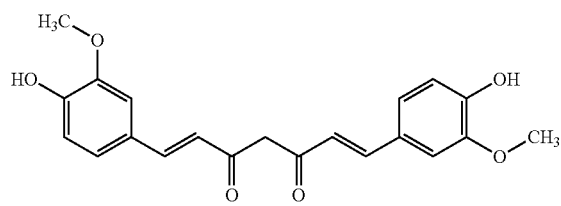

Curcumin

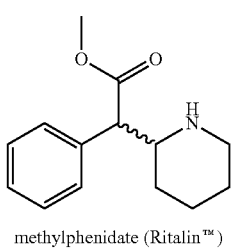

methylphenidate (Ritalin™)

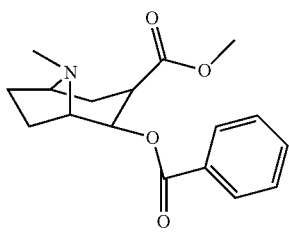

cocaine

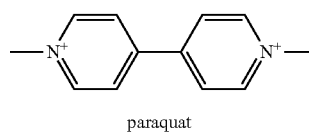

paraquat

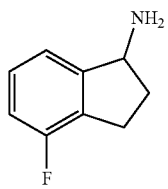

4-fluoro-1-aminoindan

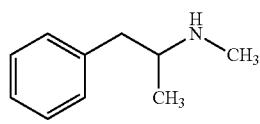

methamphetamine

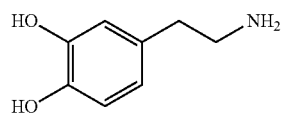

dopamine rotenone

In some embodiments, the first and second alpha-synuclein binding agents independently are: theophylline, caffeine, theobromine, nicotine, 1-aminoindan, 2-aminoindan, metformin, amphetamine, 3-methoxydopamine, curcumin, methylphenidate, cocaine, paraquat, 4-fluoro-1-aminoindan, methamphetamine, dopamine, or rotenone.

Without being bound by theory, it is believed that by linking two alpha-synuclein binding agents to produce a bifunctional molecule, e.g. a dimer or a chimera, the resulting bifunctional molecule will bind to more than one binding site on alpha-synuclein, and may bind alpha-synuclein with a higher affinity and/or with a different configuration than the individual monomeric compounds alone. In some embodiments, the binding of the bifunctional molecule to more than one binding site on alpha-synuclein is believed to cause the alpha-synuclein to assume a loop-like conformation such as that shown on the left-hand side of FIG. 1, which is believed to be neuroprotective by inhibiting or delaying the aggregation of alpha-synuclein associated with Parkinson's Disease.

In some embodiments, the first and second alpha-synuclein binding agents are covalently linked by a linker to provide the bifunctional molecule, e.g. having the structure A-L-B set forth below:

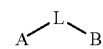

wherein A and B are alpha-synuclein binding agents (and wherein A and B may be the same alpha-synuclein binding agent or different alpha-synuclein binding agents), and wherein L is a linker.

In some embodiments, the linker used to link the first and second compounds is a saturated or unsaturated alkyl linker, for example, an alkyl linker having between 1 and 10 carbon atoms, including C1, C2, C3, C4, C5, C6, C7, C8, C9 or C10 alkyl linkers. In some embodiments, the linker can be modified, for example by being made saturated, unsaturated, alkylated, modified to include one or more heteroatoms, an aryl group, a cyclic carbon chain, halogenated, or the like. In some embodiments, the linker is an alkenyl linker or an alkynyl linker having between 1 and 10 carbon atoms, including C1, C2, C3, C4, C5, C6, C7, C8, C9 or C10 alkenyl or alkynyl linkers. In some embodiments, longer carbon chain linkers can be used if substitutions or modifications are made to increase the solubility of the linker in water, for example, unsaturated linkers, halogenated linkers or linkers containing certain heteroatoms may have increased solubility as compared with a corresponding saturated alkyl chain of the same length.

In some embodiments, the bifunctional molecules have the general structure set forth below:

wherein A is an alpha-synuclein binding agent, B is an alpha-synuclein binding agent, and n is an integer between 1 and 10, including any value therebetween e.g. 2, 3, 4, 5, 6, 7, 8, or 9. In some embodiments, A and B are the same alpha-synuclein binding agents (i.e. the bifunctional molecule is a dimer). In some embodiments, A and B are different alpha-synuclein binding agents (i.e. the bifunctional molecule is a chimera). In some embodiments, the alkyl linker covalently linking A and B is saturated, unsaturated, alkylated, substituted, modified to include one or more heteroatoms, halogenated, or otherwise modified.

In some embodiments, any heteroatom(s) present in the linker are independently nitrogen (N), oxygen (O), sulphur (S), phosphorous (P), chlorine (Cl), bromine (Br) or iodine (I).

In some embodiments, any halogen atom(s) present on the linker are independently fluorine (F), chlorine (Cl), bromine (Br) or iodine (I).

In some embodiments, the bifunctional molecules have the structure (I), (II), (III), (IV), (V), (VI), (VII), (VIII), (IX) or (X) set forth below, wherein $R_1$, $R_2$, $R_3$, $R_4$, $R_5$ and $R_6$ are independently hydrogen or a saturated or unsaturated alkyl group having between 1 and 10 carbon atoms, including 2, 3, 4, 5, 6, 7, 8, or 9 carbon atoms, wherein $R_1$, $R_2$, $R_3$, $R_4$, $R_5$ and $R_6$ are independently optionally substituted, modified to include one or more heteroatoms, halogenated, or otherwise modified, wherein n is an integer between 1 and 10, including any value therebetween e.g. 2, 3, 4, 5, 6, 7, 8, or 9, to define a linker. Heteroatoms that can be used in some embodiments in $R_1$, $R_2$, $R_3$, $R_4$, $R_5$ and $R_6$ include nitrogen (N), oxygen (O), sulphur (S), phosphorous (P), chlorine (Cl), bromine (Br) or iodine (I). Halogen atoms that can be used in some embodiments in $R_1$, $R_2$, $R_3$, $R_4$, $R_5$ and $R_6$ include fluorine (F), chlorine (Cl), bromine (Br) or iodine (I). In some embodiments, the linker is saturated, unsaturated, alkylated, substituted, modified to include one or more heteroatoms, halogenated, or otherwise modified, for example as described above.

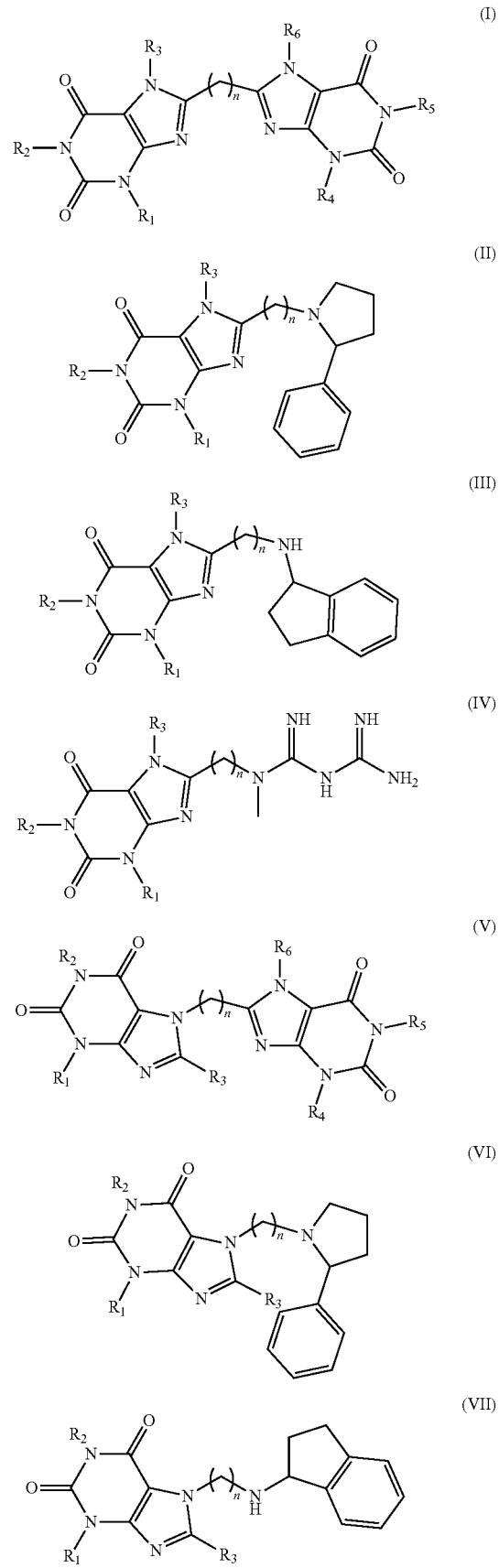

-continued (VIII)

(IX)

(X)

In some example embodiments selected for initial characterization, a two-, four-, five-, six-, seven- or eight-carbon alkyl linker was used to covalently link two alpha-synuclein binding agents. Without being bound by theory, it was believed that such alkyl linkers would likely minimize solubility problems and yet retain enough flexibility to allow both alpha-synuclein binding agents to bind simultaneously to alpha-synuclein.

In some example embodiments, a bifunctional molecule has one of the structures (1), (2), (3), (4), (5), (6), (7) or (8) shown below, wherein C denotes caffeine, M denotes Metformin, I denotes (R,S)-1-aminoindan, and N denotes (R,S)-nicotine, the subscript number indicates the ring position of attachment of caffeine to the linker, and the intermediate integer indicates the length of the alkyl linker:

(1) = $C_8$-6-$C_8$ (2) = $C_8$-6-N

-continued (3) = $C_8$-6-I (4) = $C_8$-6-M (5) = $C_7$-6-$C_7$ (6) = $C_7$-6-N (7) = $C_7$-6-I (8) = $C_7$-6-M In some example embodiments, a bifunctional molecule has one of the structures shown below, wherein C denotes caffeine, M denotes Metformin, I denotes (R,S)-1-aminoindan, and N denotes (R,S)-nicotine, the subscript number indicates the ring position of attachment of caffeine to the linker, and the intermediate integer indicates the length of the alkyl linker:

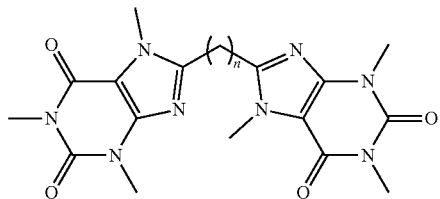

C$_8$-n-C$_8$
(9) n = 2, C$_8$-2-C$_8$
(10) n = 4, C$_8$-4-C$_8$
(1) n = 6, C$_8$-6-C$_8$

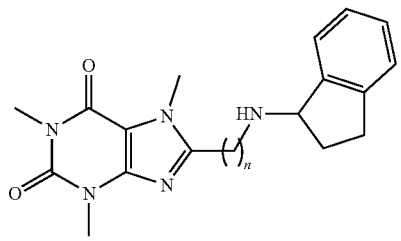

C$_8$-n-I
(11) n = 4, C$_8$-4-I
(3) n = 6, C$_8$-6-I
(12) n = 8, C$_8$-8-I

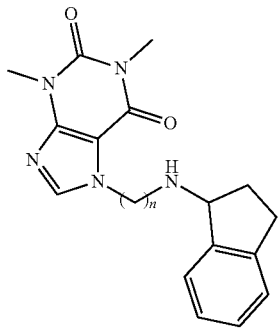

C$_7$-n-I
(13) n = 2, C$_7$-2-I
(14) n = 4, C$_7$-4-I
(7) n = 6, C$_7$-6-I
(15) n = 8, C$_7$-8-I

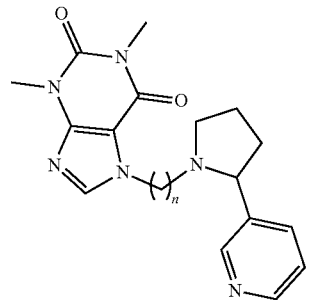

C$_7$-n-N
(16) n = 2, C$_7$-2-N
(17) n = 4, C$_7$-4-N
(6) n = 6, C$_7$-6-N
(18) n = 8, C$_7$-8-N

-continued

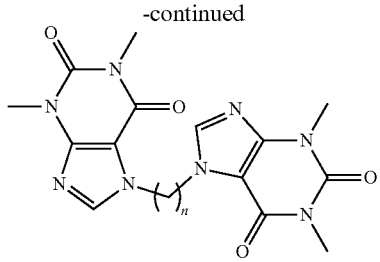

C$_7$-n-C$_7$
(19) n = 2, C$_7$-2-C$_7$
(20) n = 4, C$_7$-4-C$_7$
(5) n = 6, C$_7$-6-C$_7$
(21) n = 8, C$_7$-8-C$_7$

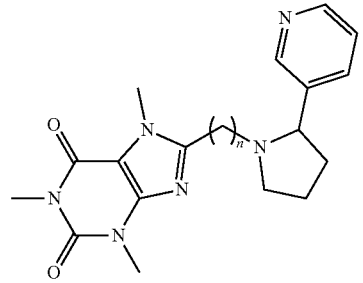

C$_8$-n-N
(22) n = 4, C$_8$-4-N
(2) n = 6, C$_8$-6-N
(23) n = 8, C$_8$-8-N

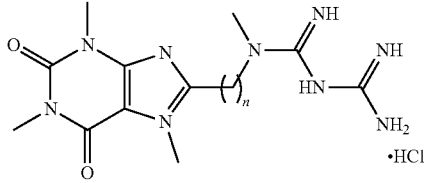

C$_8$-n-M
(24) n = 4, C$_8$-4-M
(25) n = 5, C$_8$-5-M
(4) n = 6, C$_8$-6-M
(26) n = 7, C$_8$-7-M
(27) n = 8, C$_8$-8-M

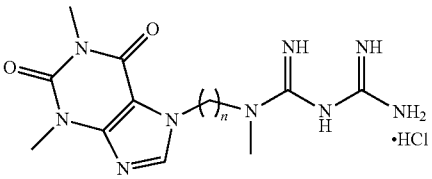

C$_7$-n-M
(8) n = 6, C$_7$-6-M

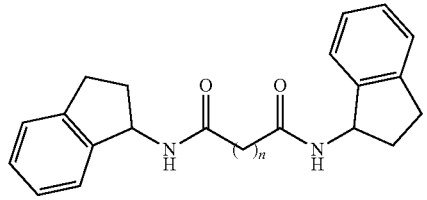

I-n-I (amide)
(28) n = 2, I-4-I (amide)
(29) n = 4, I-6-I (amide)

In some embodiments, the bifunctional molecule has one of the following structures:

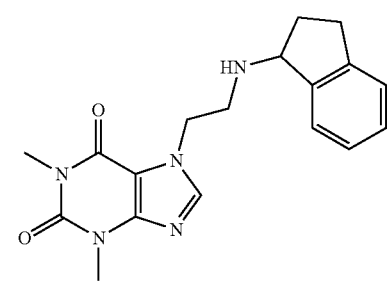
(13) = C$_7$-2-I
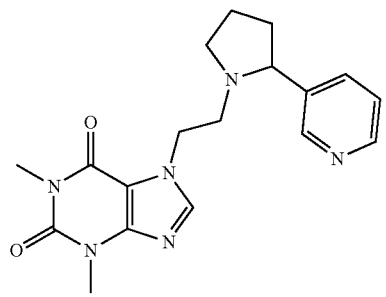
(16) = C$_7$-2-N
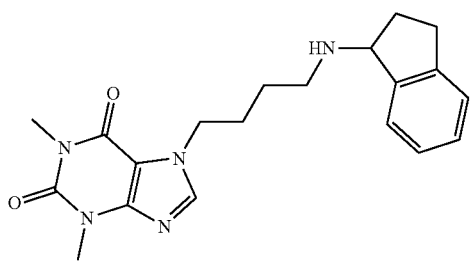
(14) = C$_7$-4-I
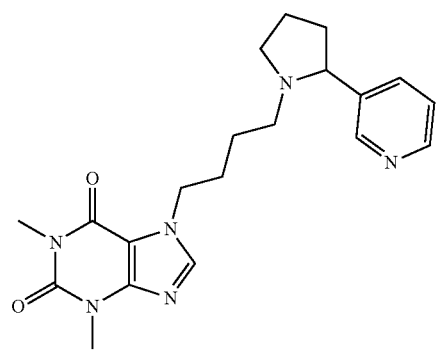
(17) = C$_7$-4-N
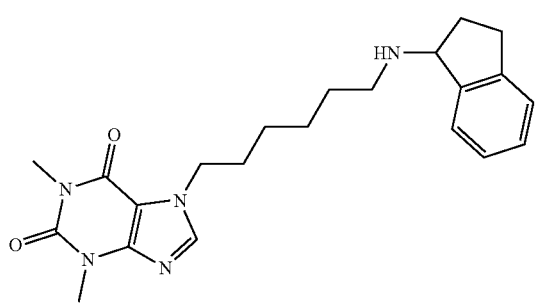
(7) = C$_7$-6-I
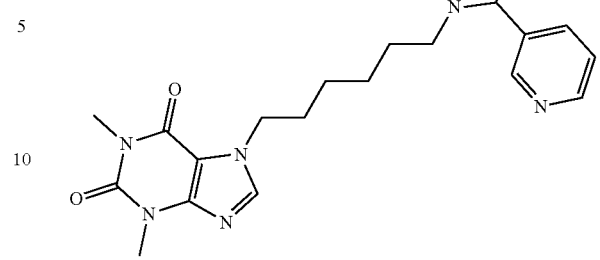
(6) = C$_7$-6-N
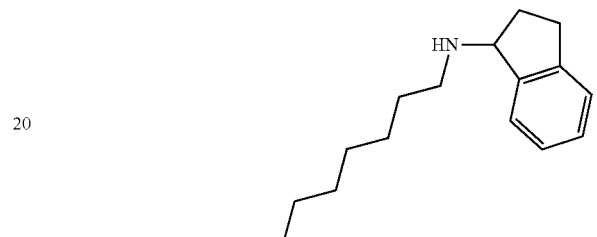
(15) = C$_7$-8-I
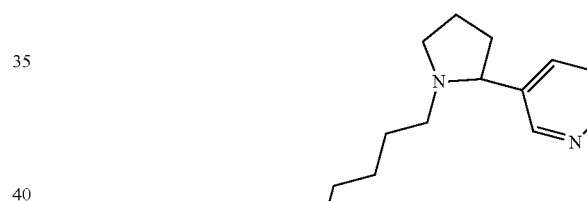
(18) = C$_7$-8-N
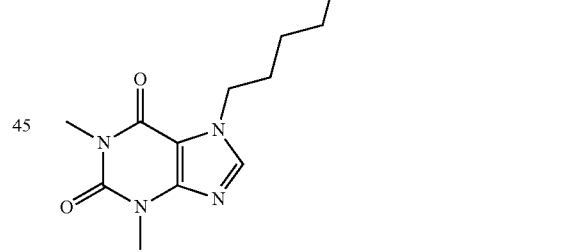
(19) = C$_7$-2-C$_7$

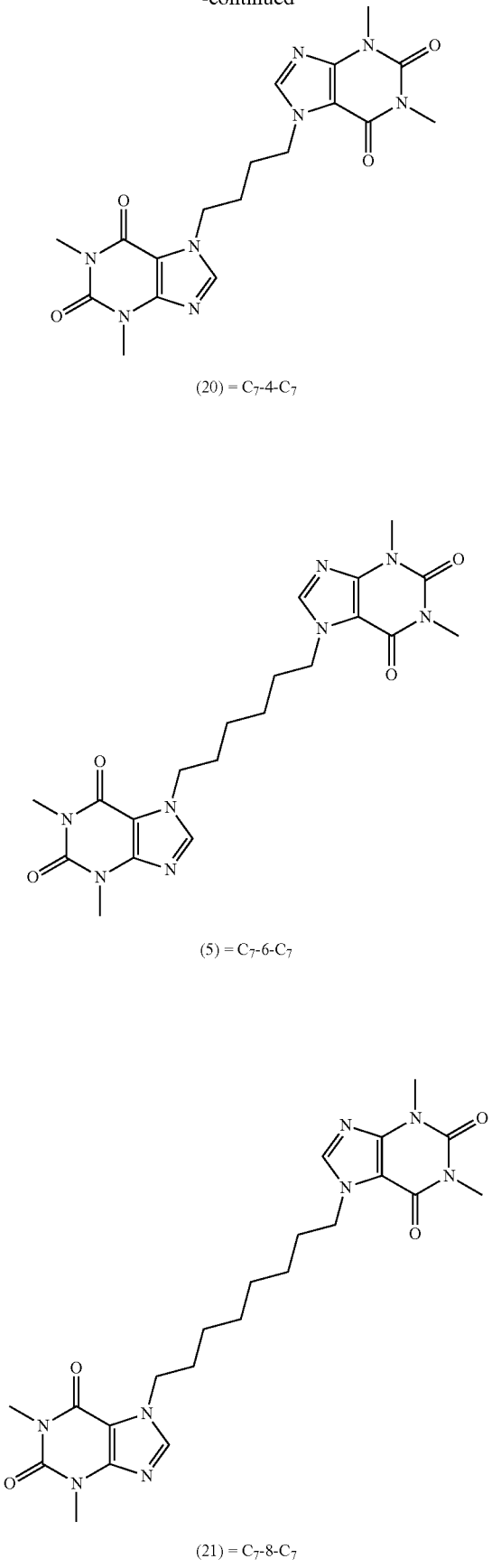
(20) = C₇-4-C₇
(5) = C₇-6-C₇
(21) = C₇-8-C₇
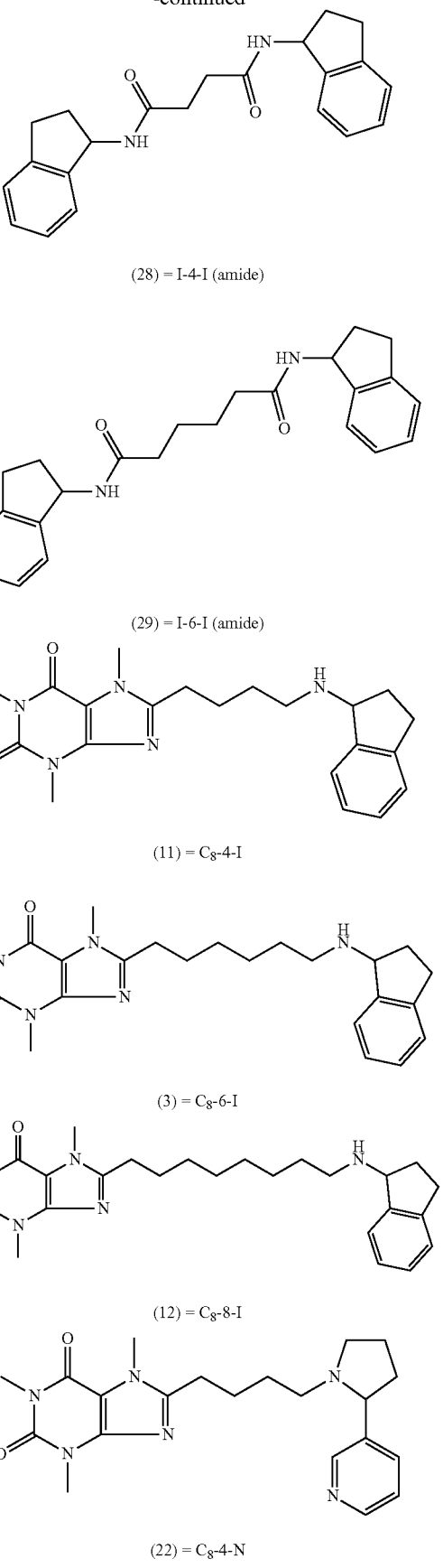
(28) = I-4-I (amide)
(29) = I-6-I (amide)
(11) = C₈-4-I
(3) = C₈-6-I
(12) = C₈-8-I
(22) = C₈-4-N -continued

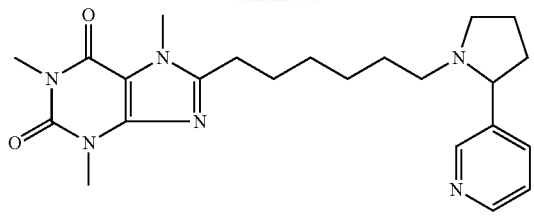

(2) = C_8-6-N

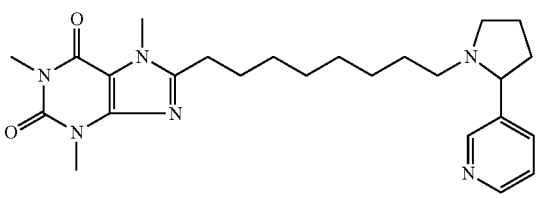

(23) = C_8-8-N

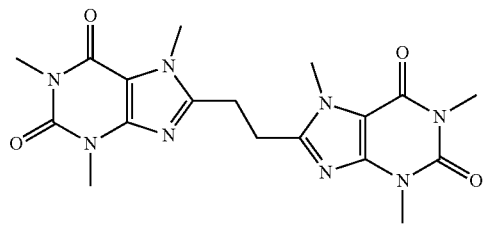

(9) = C_8-2-C_8

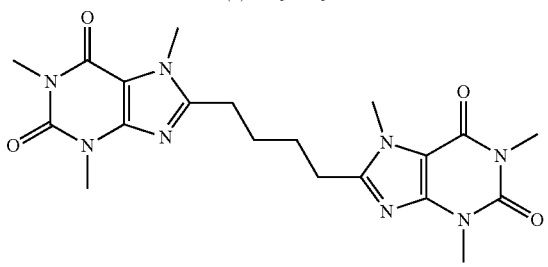

(10) = C_8-4-C_8

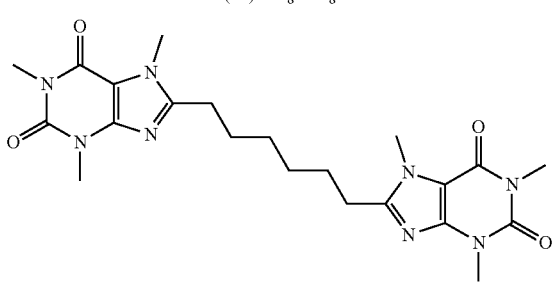

(1) = C_8-6-C_8

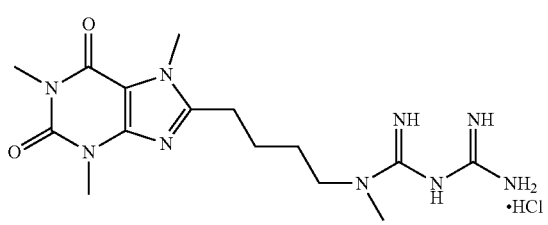

(24) = C_8-4-M

-continued

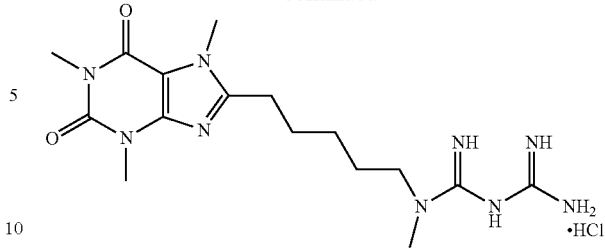

(25) = C_8-5-M

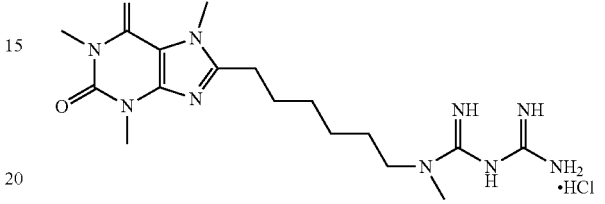

(4) = C_8-6-M

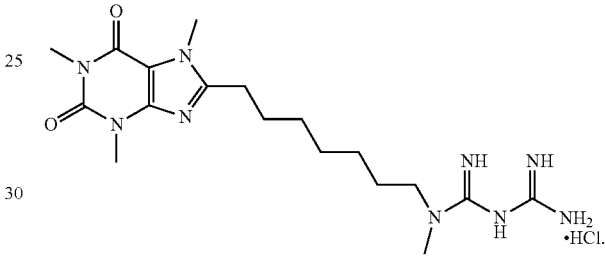

(26) = C_8-7-M

In some embodiments, the bifunctional molecule binds to alpha-synuclein in a manner that promotes formation of a loop structure on the part of the alpha-synuclein.

In some embodiments, there is one binding site for the bifunctional molecule per molecule of alpha-synuclein. In some embodiments, there is 0.25, 0.5, 2, 3 or more binding sites for the bifunctional molecule per molecule of alpha-synuclein.

In some embodiments, the binding of the bifunctional molecule to alpha-synuclein causes the alpha-synuclein to adopt a loop-like conformation. In some embodiments, alpha-synuclein is considered to have a loop-like conformation if analysis of the alpha-synuclein-bifunctional molecule complex by nanopore analysis indicates a major translocation peak at between −40 pA and −80 pA when the ratio of alpha-synuclein to the bifunctional molecule in the tested solution is approximately 1:20, including any value therebetween, e.g. −41, −42, −43, −44, −45, −46, −47, −48, −49, −50, −51, −52, −53, −54, −55, −56, −57, −58, −59, −60, −61, −62, −63, −64, −65, −66, −67, −68, −69, −70, −71, −72, −73, −74, −75, −76, −77, −78 or −79 pA. In some such embodiments, the nanopore analysis indicates only a minor bumping peak for the alpha-synuclein-bifunctional molecule complex. A "minor" bumping peak is considered to be present if at least 70% of the events detected are translocation events rather than bumping events, including any value greater than 70%, e.g. 75%, 80%, 82%, 84%, 86%, 88%, 90%, 91%, 92%, 93%, 94%, 95%, 96%, 97%, 98% or 99% up to a maximum of 100% of events being translocation events.

In some embodiments, the bifunctional molecule is labelled with a suitable label and used as a diagnostic agent in PET scanning. In some embodiments, the bifunctional molecule is labelled with $^{18}$F, $^{11}$C, $^{13}$N or $^{15}$O and injected into a subject suspected to have or at risk of having Parkinson's Disease. In some embodiments the subject is a mammal, for example a human being. In some embodiments, the distribution and quantity of alpha-synuclein present in the subject is evaluated by PET scanning. In some embodiments, the distribution of alpha-synuclein in the subject's brain, including the substantia nigra, is evaluated. In some embodiments, if the alpha-synuclein distribution in the subject, the subject's brain, and/or the subject's substantia nigra is similar to patients suffering from Parkinson's Disease, it is concluded that the subject has a likelihood of having or developing Parkinson's Disease.

In some embodiments, a bifunctional molecule is labelled with a suitable label and provided as a reagent for use as an imaging agent in PET scanning. In some embodiments, the bifunctional molecule is labelled with $^{18}F$, $^{11}C$, $^{13}N$ or $^{15}O$ and provided as a reagent for use as an imaging agent in PET scanning. In some embodiments, kits for conducting PET scanning comprising a bifunctional molecule labelled with $^{18}F$, $^{11}C$, $^{13}N$ or $^{15}O$ are provided.

In some embodiments, the bifunctional molecule decreases aggregation of alpha-synuclein. In some embodiments, the bifunctional molecule decreases the aggregation of alpha-synuclein in a yeast model of Parkinson's Disease. In some embodiments, the bifunctional molecule allows improved growth of yeast overexpressing alpha-synuclein in a yeast model of Parkinson's Disease. In some embodiments, the bifunctional molecule causes disaggregation of previously aggregated alpha-synuclein foci in a yeast model of Parkinson's Disease. In some embodiments, the bifunctional molecule decreases the accumulation and/or aggregation of alpha-synuclein in the substantia nigra of a rat model in which alpha-synuclein expression is increased. In some embodiments, the bifunctional molecule can improve the motor function of rats in which alpha-synuclein expression is increased. Improved motor function can be evaluated, for example, by assessing the vigor and success of such rats in a forced swim test.

In some embodiments, a therapeutically effective amount of the bifunctional molecule is administered to a mammal, including a human being, in need of reduced aggregation of alpha-synuclein. In some embodiments, a therapeutically effective amount of the bifunctional molecule is administered to a human having Parkinson's Disease to treat or limit the progression of the disease. In some embodiments, the bifunctional molecule is administered to a human believed to be at risk of developing Parkinson's Disease to prevent or delay the progression of the development of Parkinson's Disease.

EXAMPLES

Some exemplary embodiments are further described with reference to the following examples, which are intended to be illustrative and not limiting in nature.

Example 1.0—Synthesis of Test Compounds

One set of tested compounds were based on caffeine linked through either the C-8 or N-7 positions. Carbodiimide-coupling between 5,6-diamino-1,3-dimethyluracil and the appropriate carboxylic acid, followed by ring closing hydrolysis,[50] furnished the C-8 modified xanthines (compounds (1), (2), (3) and (4)). Scheme 1 outlines synthetic schemes by which these alkyl-linked bifunctional drugs were produced (e.g., alkylation, guanidinylation, deprotection sequences, etc.). N-7 modified bifunctional drugs were prepared via alkylation of theophylline,[51] using the appropriate alkyl bromide, followed by a similar series of synthetic manipulations to that described above (Scheme 2) to yield compounds (5), (6), (7) and (8).

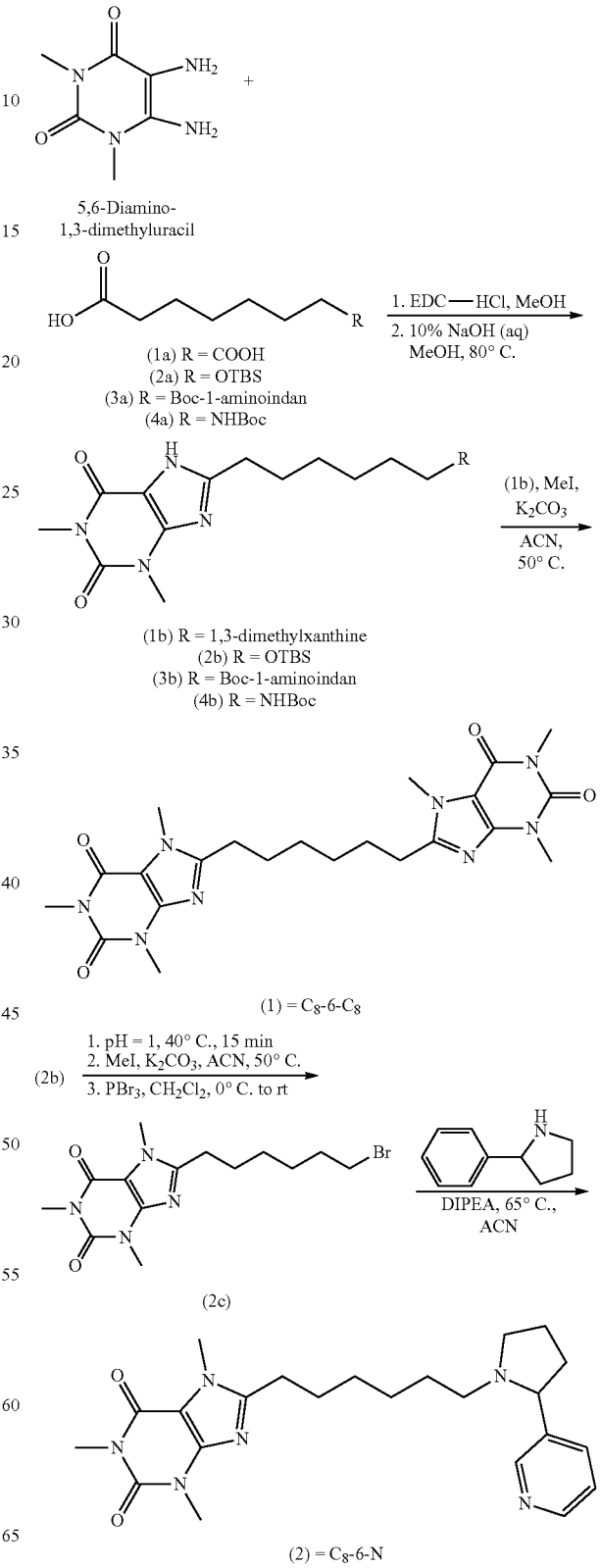

Scheme 1: Brief overview of synthesis of C8 linked bifunctional molecules.

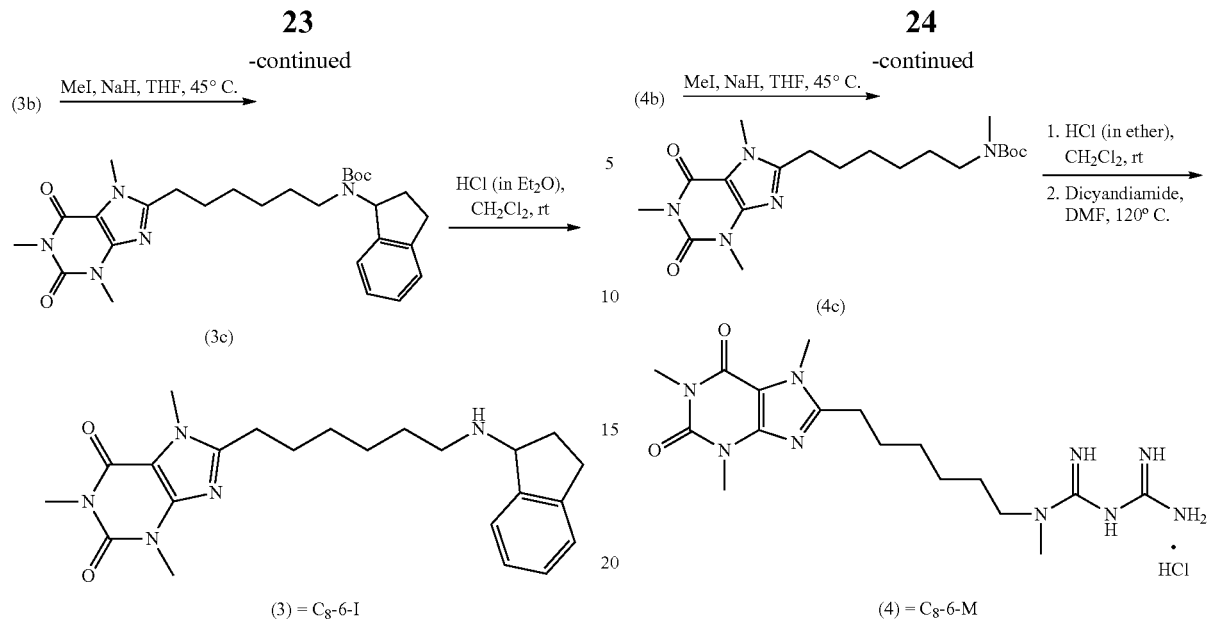
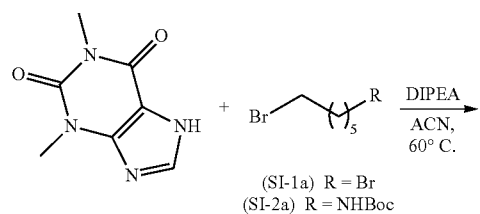
Scheme 2: Brief overview of synthesis of $N_7$ linked bifunctional molecules.
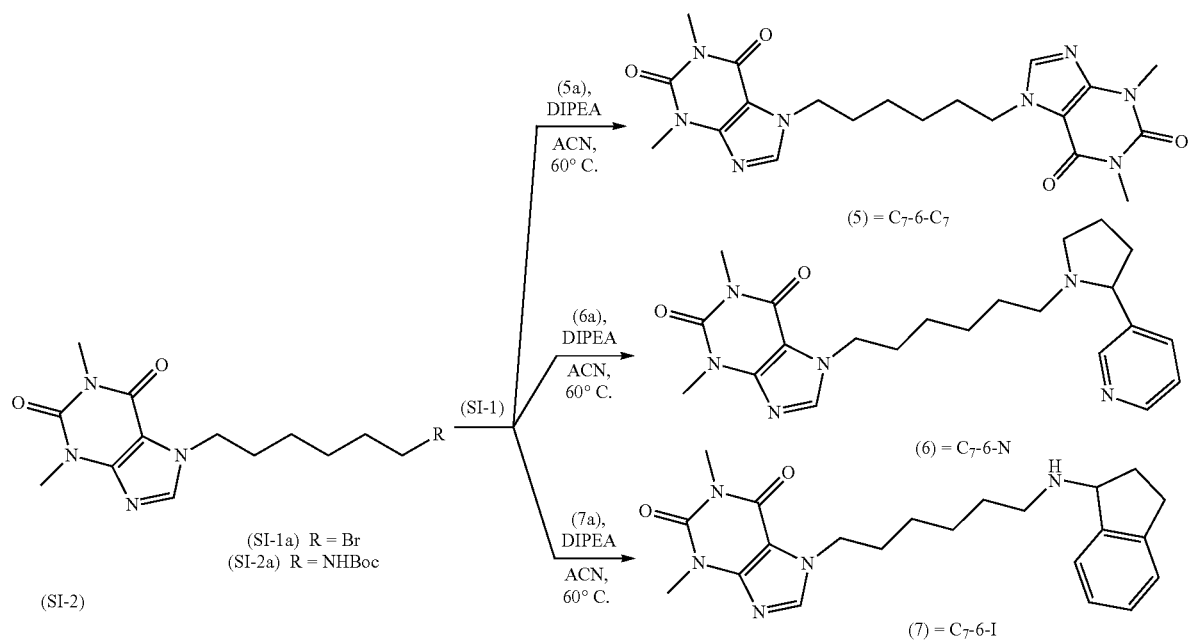

-continued

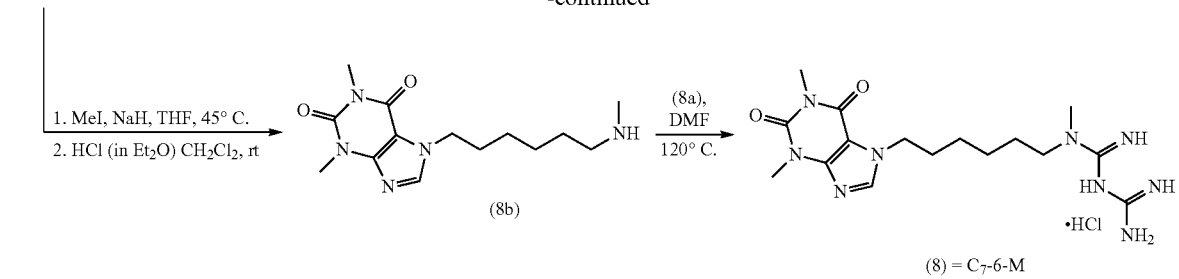

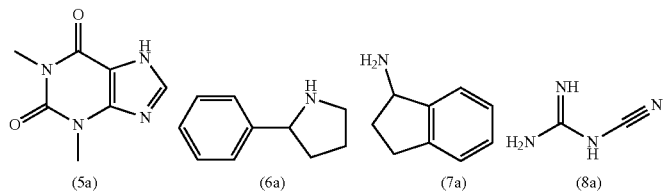

For ease of synthesis, linkage of nicotine, 1-aminoindan and metformin was achieved through their respective amino groups. As well, the inventors had previously demonstrated that nornicotine and buformin (1-butylbiguanide) bound well to alpha-synuclein, suggesting that substitution on the N1 of nicotine and the N1 position of metformin might not interfere with binding. This suggested that linkers at these positions might not interfere with binding. For caffeine, linkage was accomplished through both the N-7 and C-8 positions because synthetic methods were already available and because compounds substituted at these positions, specifically 7-ethyltheophyline and 8-propenylcaffeine, had been previously found by the inventors to bind well to alpha-synuclein. 1-aminoindan and nicotine were provided as (R,S) enantiomers. It would be within the expected ability of the person of ordinary skill in the art to synthesize or isolate and test the corresponding pure isomers.

All chemicals were purchased from Sigma-Aldrich or Chem-impex and used as is. Solvents were highest-purity available and purchased from Fisher Scientific (Fairlawn, N.J.). Deionised water was obtained using a Millipore Q-POD Milli-Q 0.22 μm filter, 18 mΩ. (2a) (40%) was synthesized using an established literature method.[56] EDC coupling and xanthine formation were based on an establish literature procedure.[57]

TLC aluminium sheets, coated with silica gel 60 F254, were purchased from EMD Chemicals Inc. (Gibbstown, N.J.). Solvents were evaporated using a Büchi Rotavapor R-200, and Büchi v700 vacuum pump with attached v850 vacuum controller. Trace solvents were removed with an Edwards High vacuum pump. HPLC experiments were carried out using an Agilent Series 1200 quaternary pump (G1311A) with online degasser (G1322A), autosampler (G1329A) and photodiode array detector (G1315D) (Agilent Technologies, Mississauga, ON). Data was processed using Chemstation software.

Samples for NMR spectroscopy were recorded on a Bruker AMX-500 MHz NMR spectrometer, or Bruker AMX-600 MHz NMR, data was processed using TopSpin 3.2. HR-ESI-MS data was collected using an AB SCIEX QSTAR XL, MS/MS system. * denotes peaks that are split due to intermediate exchange (on the NMR time scale) between rotamers causing peak broadening or peak splitting.

Purity was determined by HPLC using a Lichrosphere RP-C18 5 μm (length=150 mm, ID=4.6 mm) column at 1 mL/min running a gradient from 90:10 $H_2O$/ACN (v/v) to 60:40 $H_2O$/ACN (v/v) (t=8 minutes) to 10:90 $H_2O$/ACN (v/v) (t=14 minutes) to 10:90 $H_2O$/ACN (v/v) (t=16 minutes) to 90:10 $H_2O$/ACN (v/v) (t=20 minutes). All solvents contained 0.1% TFA and 0.1% $Et_3N$.

Scheme 3: Detailed Synthesis of (1) - $C_8$-6-$C_8$.

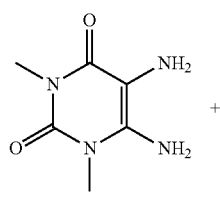

5,6-Diamino-1,3-dimethyluracil

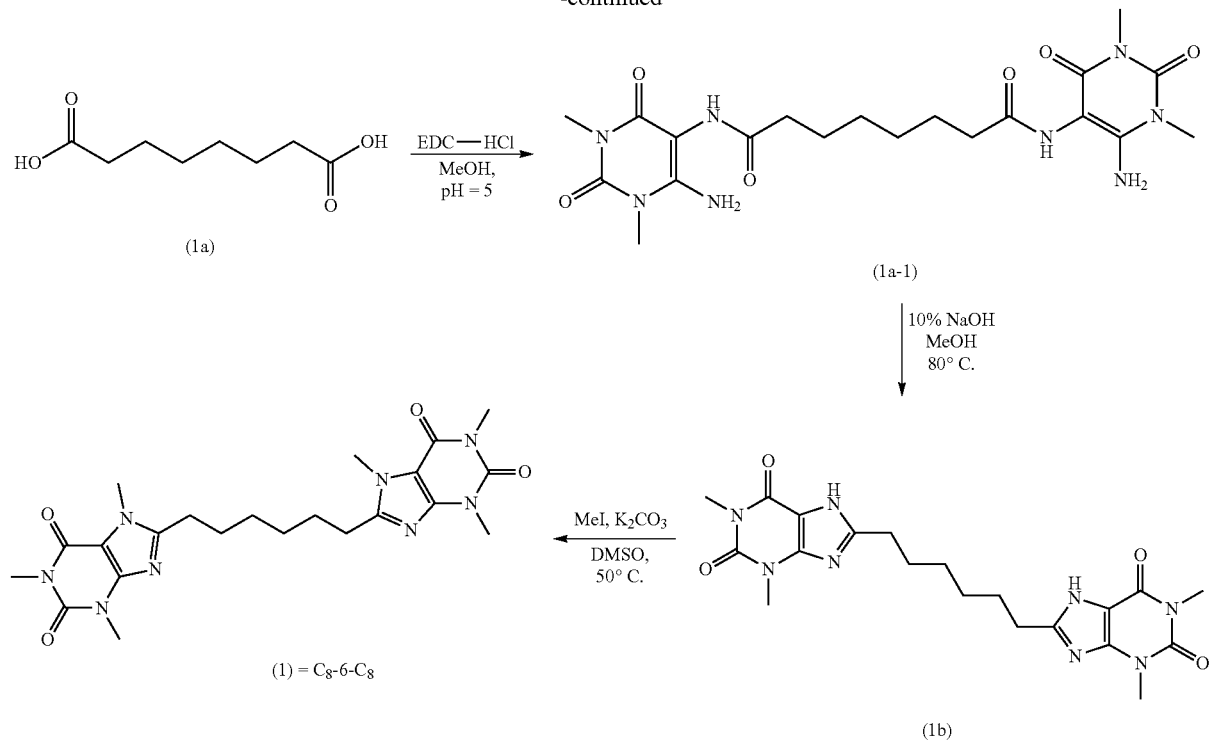

1,6-di-(N-6-amino-1,2,3,4-tetrahydro-1,3-dimethyl-2,4-dioxo-5-pyrimidyl)-hexanamide, (1a-1)

5,6-Diamino-1,3-dimethyluracil hydrate (0.20 g, 1.2 mmol) and suberic acid (0.092 g, 0.53 mmol) were added to MeOH (15 mL). EDC-HCl (2.6 g, 1.4 mmol) was then added in one portion and stirred overnight at room temperature. The pH was adjusted to 8 and a white precipitate formed. The precipitate was filtered and washed with acetone giving (1a-1). Yield: 0.082 g (32%). $^1$H NMR (d$_6$-DMSO, 500 MHz, 22° C.): δ 8.27 (s, 2H), 6.53 (s, 4H), 3.31 (s, 6H), 3.11 (s, 6H), 2.25 (t, $^3J_{HH}$=7.4 Hz, 4H), 1.61-1.53 (m, 4H), 1.37-1.32 (m, 4H).

1,6-di-(1,3-dimethylxantine)-hexane, (1b)

(1a-1) (0.082 g, 0.17 mmol) was dissolved in MeOH (5 mL) and 10% NaOH in H$_2$O (0.5 mL) was added. The vial was sealed and heated to 80° C. and let stir overnight. The solution was allowed to cool to room temperature and the pH was adjusted to 5 with 2 M HCl causing a white precipitate to form. The precipitate was filtered and washed with acetone giving (1b). Yield: 0.060 g (79%). $^1$H NMR (d$_6$-DMSO+basic D$_2$O, 500 MHz, 22° C.): δ 3.37 (s, 6H), 3.19 (s, 6H), 2.55-5.50 (m, 4), 1.65-1.57 (m, 4H), 1.32-1.27 (m, 4H).

C$_8$-6-C$_8$, (1)

(1b) (0.060 g, 0.14 mmol) was dissolved in anhydrous DMSO (5 mL) under N$_2$ and K$_2$CO$_3$ (0.112 g, 0.84 mmol) was added followed by MeI (0.1 mL, 1.4 mmol). The vial was sealed and heated to 50° C. overnight. The mixture was allowed to cool to room temperature and H$_2$O (10 mL) was added to quench the reaction and the mixture was then extracted with CH$_2$Cl$_2$ (3×20 mL). The organic layers were combined and dried over MgSO$_4$. The solvent was removed under reduced pressure giving a white solid, which was washed with acetone giving C$_8$-6-C$_8$ (1). Yield: 0.023 g (36%). $^1$H NMR (CDCl$_3$, 500 MHz, 22° C.): δ 3.93 (s, 3H), 3.58 (s, 3H), 3.41 (s, 3H), 2.75 (t, $^3J_{HH}$=7.7 Hz, 4H), 1.84-1.76 (m, 4H), 1.52-1.45 (m, 4H). $^{13}$C{$^1$H} NMR (CHCl$_3$, 125 MHz): δ 155.33, 154.08, 151.69, 147.91, 107.30, 31.75, 29.77, 29.01, 27.90, 27.40, 26.75. HR-ESI-MS: 471.2462 ([M+H]$^+$, C$_{22}$H$_{31}$N$_8$O$_4$; calcd: 471.2468). Purity (HPLC): ≥95%, RT=9.86 min.

Scheme 4: Detailed Synthesis of (2) - C$_8$-6-N.

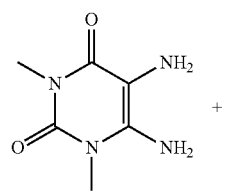

5,6-Diamino-1,3-dimethyluracil

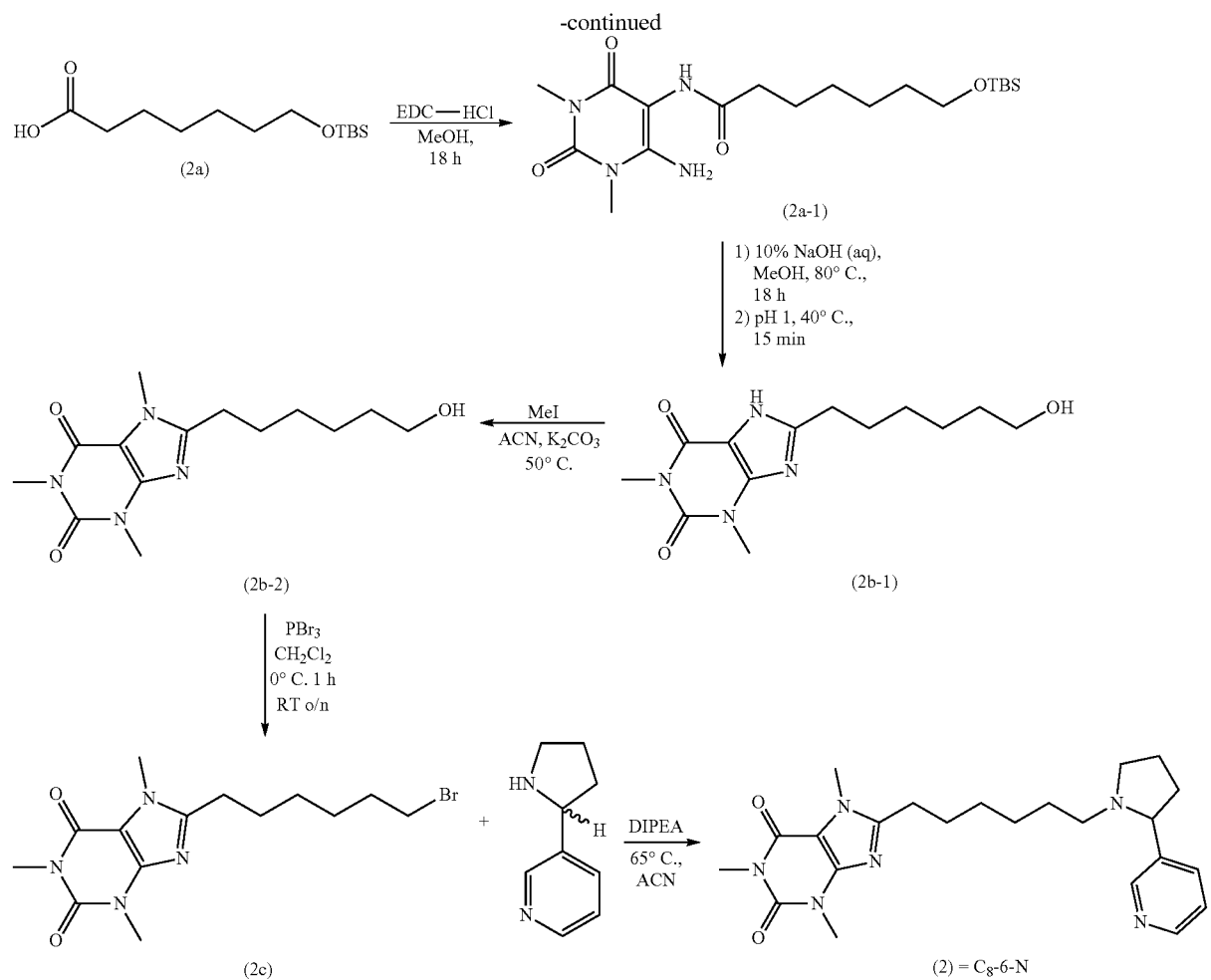

1,3-dimethyl-8-(6-hexan-1-ol)-xanthine, (2b-1)

5,6-Diaminο-1,3-dimethyluracil hydrate (0.59 g, 3.5 mmol) and (2a)[56] (1.0 g, 3.8 mmol) was added to MeOH (20 mL). EDC-HCl (1.0 g, 5.2 mmol) was added in one portion and stirred overnight at room temperature. The reaction was quenched with $H_2O$ (10 mL) and the mixture was then extracted with $CH_2Cl_2$ (3×20 mL). The organic layers were combined and dried over $MgSO_4$, filtered, and the solvent was removed under reduced pressure to give an orange solid. The crude solid was purified by column chromatography (90:10, EtOAc/MeOH (v/v)) to give a (2a-1) as a semi-pure pale yellow solid. Semi-pure (2a-1) was then dissolved in MeOH (5 mL) and 10% NaOH in $H_2O$ (0.5 mL) was added. The vessel was sealed and heated to 80° C. and stirred overnight. The solution was allowed to cool to room temperature and the pH was adjusted to 1 with HCl, the solution was then stirred for 15 minutes at 40° C. After 0.25 h the pH was adjusted to 6-7 and the solvent was removed under reduced pressure to give a yellow solid. A minimum amount of MeOH was added to dissolve the solid, followed by addition of $H_2O$ causing (2b-1) to precipitate out of solution. Yield: 0.11 g (11%). $^1$H NMR (CDCl$_3$, 500 MHz, 22° C.): δ 12.16 (1H), 3.67-3.62 (m, 2H), 3.60 (s, 3H), 3.43 (s, 3H), 2.88-2.83 (m, 2H), 1.85-1.75 (m, 2H), 1.63-1.54 (m, 3H), 1.48-1.35 (m, 4H).

1,3,7-trimethyl-8-(6-hexan-1-ol)-xanthine, (2b-2)

(2b-1) (0.11 g, 0.38 mmol) was dissolved in anhydrous ACN (8 mL) under an atmosphere of $N_2$. $K_2CO_3$ (0.21 g, 1.5 mmol) was added followed by MeI (0.1 mL, 1.5 mmol). The vial was sealed and heated to 50° C. over night. The mixture was allowed to cool to room temperature and the reaction quenched with $H_2O$ (10 mL). The mixture was then extracted with EtOAc (3×20 mL), the organic layers were combined and dried over $MgSO_4$. The solvent was removed under reduced pressure giving a colourless oil which was purified by column chromatography (90:10, EtOAc/MeOH (v/v)) giving (2b-2) as a white solid. Yield: 0.061 g (55%). $^1$H NMR (CDCl$_3$, 500 MHz, 22° C.): δ 3.94 (s, 3H), 3.68 (t, $^3J_{HH}$=6.4 Hz, 2H), 3.60 (s, 3H), 3.43 (s, 3H), 2.77 (t, $^3J_{HH}$=7.3 Hz, 2H), 1.79 (p, $^3J_{HH}$=7.4 Hz, 2H), 1.61 (p, $^3J_{HH}$=7.0 Hz, 2H), 1.49-1.43 (m, 4H).

1,3,7-trimethyl-8-(6-(1-bromohexyl)-xanthine, (2c)

(2b-2) (0.061 g, 0.21 mmol) was dissolved in anhydrous $CH_2Cl_2$ (5 mL) under $N_2$ and cooled to 0° C. PBr$_3$ (0.030 mL, 0.31 mmol) was then added drop-wise to the solution. The solution was stirred for 1 hour at 0° C. then allowed to warm to room temperature. The reaction was monitored by TLC until all starting material was consumed (3 hours). The reaction was then quenched with $H_2O$ (10 mL) and extracted with $CH_2Cl_2$ (3×20 mL). The organic layers were combined and dried over $MgSO_4$, filtered, and the solvent was removed under reduced pressure. The reaction mixture was then purified by column chromatography (95:5, EtOAc/MeOH (v/v)) giving (1c) as a colourless viscous oil. Yield: 0.035 g (47%). $^1$H NMR (CDCl$_3$, 500 MHz, 22° C.): δ 3.95 (s, 3H), 3.60 (s, 3H), 3.4 (t, $^3J_{HH}$=6.9 Hz, 2H), 3.43 (s, 3H), 2.76 (t, $^3J_{HH}$=7.7 Hz, 2H), 1.90 (p, $^3J_{HH}$=7.2 Hz, 2H), 1.81 (p, $^3J_{HH}$=7.6 Hz, 2H), 1.53 (p, $^3J_{HH}$=7.5 Hz, 2H), 1.46 (p, $^3J_{HH}$=7.4 Hz, 2H).

$C_8$-6-N, (2)

(+/−)-Nornicotine (0.015 mL, 0.11 mmol) was dissolved in anhydrous ACN (5 mL) under $N_2$, DIPEA (0.026 mL, 0.15 mmol) was added and stirred for 1 h. (2c) dissolved in anhydrous ACN (0.5 mL) was then added in one portion and the vial was sealed. The reaction vessel was then heated to 65° C. and let stir overnight. The solution was allowed to cool to room temperature and the reaction quenched with $H_2O$ (10 mL). The mixture was extracted with $CH_2Cl_2$ (3×20 mL), the organic layers were then combined, dried over $MgSO_4$, filtered, and the solvent was removed under reduced pressure. The reaction mixture was then purified via column chromatography (80:20, EtOAc/MeOH (v/v)) giving $C_8$-6-N (2) as a viscous yellow oil. Yield: 0.012 g (29%). $^1H$ NMR (MeOD, 500 MHz, 22° C.): δ 8.67-8.32 (br. m, 2H), 7.85 (d, $^3J_{HH}$=7.9 Hz, 1H), 7.41 (s, 1H), 3.88 (s, 3H), 3.49 (s, 3H), 3.40 (t, $^3J_{HH}$=8.0 Hz, 2H), 3.32 (s, 3H), 2.73 (t, $^3J_{HH}$=7.6 Hz, 2H), 2.52-2.45 (m, 1H), 2.32 (q, $^3J_{HH}$=9.0 Hz, 1H), 2.28-2.21 (m, 1H), 2.20-2.13 (m, 1H), 2.02-1.86 (m, 2H), 1.76-1.65 (m, 3H), 1.50-1.41 (m, 2H), 1.37-1.29 (m, 4H). $^{13}C\{^1H\}$ NMR (MeOD, 125 MHz): 153.56, 153.52, 150.19, 146.85, 146.18, 146.07, 137.91, 134.55, 122.35, 105.48, 66.14, 52.43, 51.74, 32.64, 29.26, 27.12, 27.04, 26.29, 25.41, 25.23, 25.07, 24.33, 20.45. HR-ESI-MS: 425.2649 ([M+H]$^+$, $C_{23}H_{33}N_6O_2$; calcd: 425.2665). Purity (HPLC): ≥95%, RT=7.17 min Scheme 5: Detailed Synthesis of (3) - $C_8$-6-I.

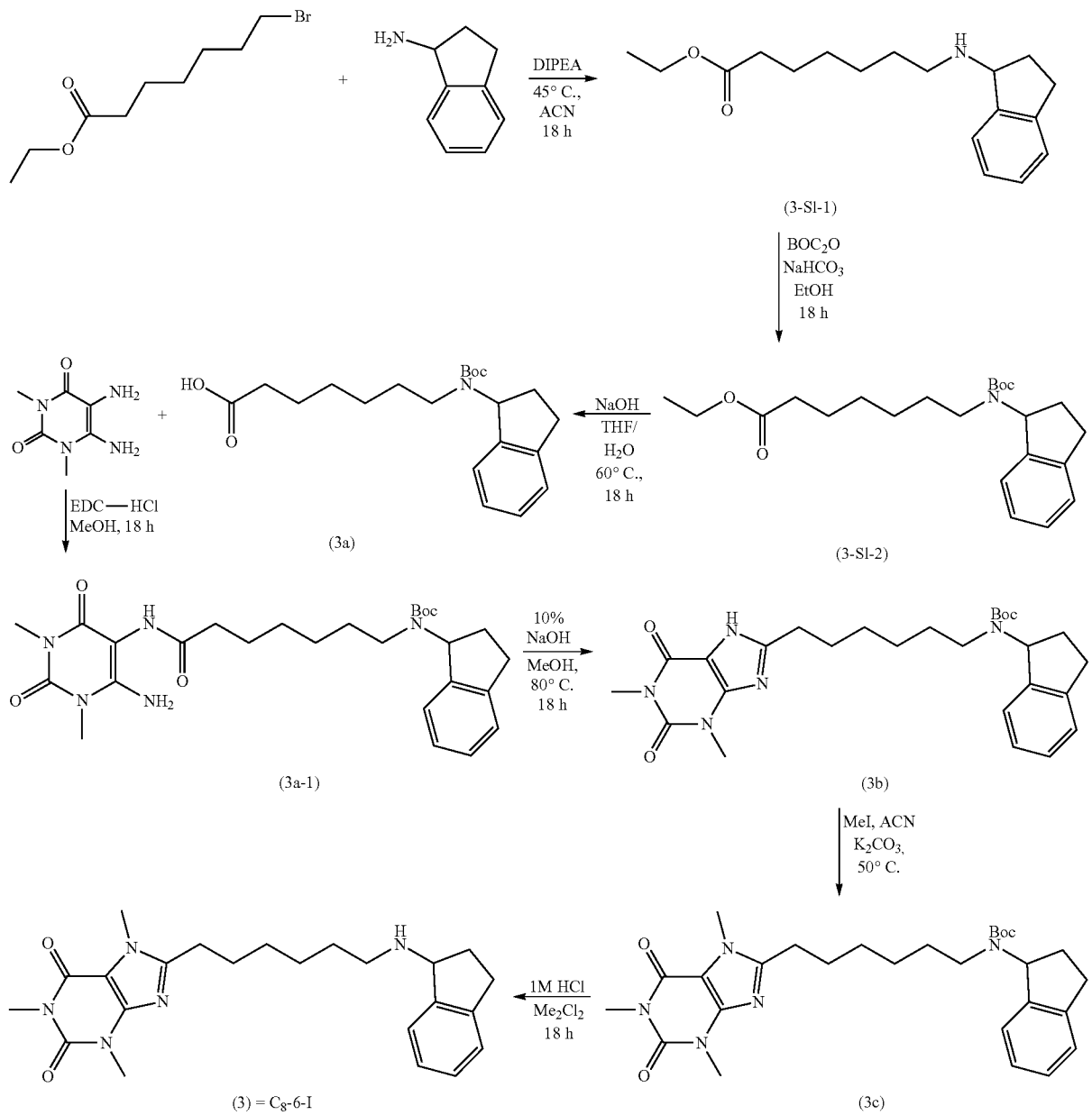

N-ethylheptanoate-2,3-dihydro-1H-indan-1-amine, (3-SI-1)

(+/−)-1-aminoindan (0.45 mL, 3.5 mmol) was dissolved in anhydrous ACN (10 mL) under $N_2$, DIPEA (1.2 mL, 7.0 mmol) was added and let stir for 1 hour. Ethyl 7-bromoheptanoate (0.45 mL, 2.33 mmol) was then added drop-wise and the vial was sealed. The reaction vessel was heated to 45° C. and stirred overnight. The solution was allowed to cool to room temperature and the reaction quenched with $H_2O$ (10 mL). The mixture was extracted with $CH_2Cl_2$ (3×20 mL), the organic layers were combined and dried over $MgSO_4$. The solution was filtered, and the solvent was removed under reduced pressure followed by purification via column chromatography (EtOAc) giving (3-SI-1). Yield: 0.41 g (60%). $^1H$ NMR (CDCl$_3$, 500 MHz, 22° C.): δ 7.38-7.34 (m, 1H), 7.28-7.21 (m, 3H), 4.26 (t, $^3J_{HH}$=6.5 Hz, 1H), 4.26 (q, $^3J_{HH}$=7.2 Hz, 2H), 3.06-2.98 (m, 1H), 2.88-2.80 (m, 1H), 2.73 (t, $^3J_{HH}$=7.2 Hz, 2H), 2.46-2.38 (m, 1H), 2.32 (t, $^3J_{HH}$=7.6 Hz, 2H), 1.89-1.81 (m, 1H), 1.65 (q, $^3J_{HH}$=7.2 Hz, 2H), 1.55 (q, $^3J_{HH}$=7.0 Hz, 2H), 1.44 (br. s, 1H), 1.42-1.32 (m, 4H), 1.55 (t, $^3J_{HH}$=7.3 Hz, 3H)

N-Boc-N-ethylheptanoate-2,3-dihydro-1H-indan-1-amine, (3-SI-2)

(3-SI-1) (0.41 g, 1.4 mmol) was dissolved in EtOH (4 m). To this solution $K_2CO_3$ (1.95 g, 14 mmol) and $BOC_2O$ (0.36 mL, 1.5 mmol) were added and stirred for 18 hours. $H_2O$ (15 mL) was added to quench the reaction and the mixture was extracted with $CH_2Cl_2$ (3×20 mL). The organic layers were combined and dried over $MgSO_4$. The solution was filtered and the solvent was removed under reduced pressure followed by purification via column chromatography (70:30, Hexanes/EtOAc (v/v)) giving 3-SI-2 as a white solid. Yield: 0.52 g (94%). $^1H$ NMR (CDCl$_3$, 500 MHz, 22° C.): δ 7.22-7.09 (m, 4H), 7.28-7.21 (m, 3H), 5.74* (s, 0.5H), 5.24* (s, 0.5H), 4.08 (q, $^3J_{HH}$=6.9 Hz, 2H), 3.17* (s, 0.5H), 3.00-2.88 (m, 2H), 2.70* (s, 0.5H), 2.84-2.76 (m, 1H), 2.42-2.31 (br. s, 1H), 2.22 (t, $^3J_{HH}$=7.6 Hz, 2H), 1.97 (fluxional doublet, 76.4 Hz, 1H), 1.58-1.39 (m, 9H), 1.34-1.16 (m, 11H).

N-Boc-N-ethylheptanoic acid-2,3-dihydro-H-indan-1-amine, (3a)

In a pressure vessel (3-SI-2) (0.52 g, 1.3 mmol) was dissolved in THF (5 mL). 10% NaOH (1 mL) was added, the vessel was sealed and heated to 60° C. for 18 h. The solution was then allowed to cool to room temperature and $H_2O$ (15 mL) was added to quench the reaction. The pH was adjusted to 4 using 1 M HCl and extracted with $CH_2Cl_2$ (3×20 mL). The organic layers were combined and dried over $MgSO_4$. The solution was filtered and the solvent was removed under reduced pressure followed by purification via column chromatography (60:40, Hexanes/EtOAc (v/v)) giving (3a) as viscous colourless oil that solidified upon standing. Yield: 0.44 g (91%). $^1H$ NMR (CDCl$_3$, 500 MHz, 22° C.): δ 7.22-7.09 (m, 4H), 5.74* (s, 0.5H), 5.24* (s, 0.5H), 3.00-2.88 (m, 2H), 3.17* (s, 0.5H), 2.85-2.77 (m, 1H), 2.71* (s, 0.5H), 2.37 (br. s, 1H), 2.27 (t, $^3J_{HH}$=6.9 Hz, 2H), 2.05* (s, 0.5H), 1.90* (s, 0.5H), 1.64-1.05 (m, 17H).

1,3-dimethyl-8-(N-Boc-N-ethylheptyl-2,3-dihydro-1H-indan-1-amine)-xanthine, (3b)

5,6-Diamino-1,3-dimethyluracil hydrate (0.23 g, 1.33 mmol) and (3a) (0.44 g, 1.2 mmol) was added to MeOH (20 mL). EDC-HCl (0.35 g, 1.82 mmol) was added in one portion to a vessel and stirred overnight at room temperature. The reaction was quenched with $H_2O$ (20 mL) and the mixture was then extracted with $CH_2Cl_2$ (3×20 mL). The organic layers were combined and dried over $MgSO_4$, filtered, and the solvent was removed under reduced pressure to give an orange solid. The crude solid was purified by column chromatography (80:20, EtOAc/MeOH (v/v)) to give (3a-1) as a semi-pure pale orange solid. Semi-pure (3a-1) was then dissolved in MeOH (10 mL) and 10% NaOH in $H_2O$ (1 mL) was added. The vial was sealed and heated to 80° C. and stirred overnight. The solution was allowed to cool to room temperature and the pH was adjusted to 6-7 and the solvent was removed under reduced pressure to give a yellow solid. A minimum amount of MeOH was added to dissolve the solid, followed by addition of $H_2O$ causing (3b) to precipitate as a white solid. Yield: 0.12 g (19%). $^1H$ NMR (CDCl$_3$, 500 MHz, 22° C.): δ 12.52 (s, 1H), 7.19-7.08 (m, 4H), 5.72* (s, 0.5H), 5.22* (s, 0.5H), 3.59 (s, 3H), 3.41 (s, 3H), 3.18* (s, 0.5H), 3.01-2.87 (m, 2H), 2.70* (s, 0.5H), 2.85-2.75 (m, 3H), 2.35 (br. s, 1H), 2.10-1.67 (m, 5H), 1.53-1.18 (m, 13H).

1,3,7-trimethyl-8-(N-Boc-N-ethylheptyl-2,3-dihydro-1H-indan-1-amine)-xanthine, (3c)

(3c) was prepared by the same procedure as (2b-2) by substituting (3b) for (2b-1). Yield: 0.080 g (71%). $^1H$ NMR (CDCl$_3$, 500 MHz, 22° C.): δ 7.20-7.08 (m, 4H), 5.74* (s, 0.5H), 5.26* (s, 0.5H), 3.86 (s, 3H), 3.53 (s, 3H), 3.37 (s, 3H), 3.17* (s, 0.5H), 3.01-2.89 (m, 2H), 2.72* (s, 0.5H), 2.85-2.75 (m, 1H), 2.65 (t, $^3J_{HH}$=7.5 Hz, 2H), 2.36 (br. s, 1H), 2.02* (s, 0.5H), 1.89* (s, 0.5H), 1.71-1.26 (m, 17H).

$C_8$-6-I, (3)

(3c) was dissolved in $CH_2Cl_2$ (2 mL) followed by the addition of 1M HCl in ether (1 mL) and stirred overnight. The reaction was quenched by the addition of saturated NaHCO$_3$ (10 mL) and extracted with $CH_2Cl_2$ (3×20 mL). The solution was filtered and the solvent was removed under reduced pressure followed by purification via column chromatography (80:20, EtOAc:MeOH) giving $C_8$-6-I (3) as a viscous colourless oil. Yield: 0.053 g (82%). $^1H$ NMR (CDCl$_3$, 500 MHz, 22° C.): δ 7.33-7.30 (m, 1H) 7.23-7.15 (m, 3H), 4.24 (t, $^3J_{HH}$=6.5 Hz, 1H), 3.89 (s, 3H), 3.54 (s, 3H), 3.38 (s, 3H), 3.03-2.96 (m, 1H), 2.84-2.76 (m, 1H), 2.72-2.66 (m, 4H), 2.42-2.34 (m, 1H), 1.91-1.83 (m, 1H), 1.73 (p, $^3J_{HH}$=7.5 Hz, 2H), 1.55 (p, $^3J_{HH}$=7.0 Hz, 2H), 1.43-1.35 (m, 4H). $^{13}C\{^1H\}$ NMR (CDCl$_3$, 125 MHz): δ 155.33, 154.34, 151.72, 147.99, 143.84 (2 carbons), 127.75, 126.33, 124.88, 124.39, 107.28, 62.94, 46.57, 32.57, 31.72, 30.44, 29.72, 29.63, 29.17, 27.87, 27.52, 27.04, 26.78. HR-ESI-MS: 410.2545 ([M+H]$^+$, $C_{23}H_{32}N_5O_2$; calcd: 410.2556). Purity (HPLC): ≥99%, RT=9.15 min Scheme 6: Detailed Synthesis of (4) - C₈-6-M.

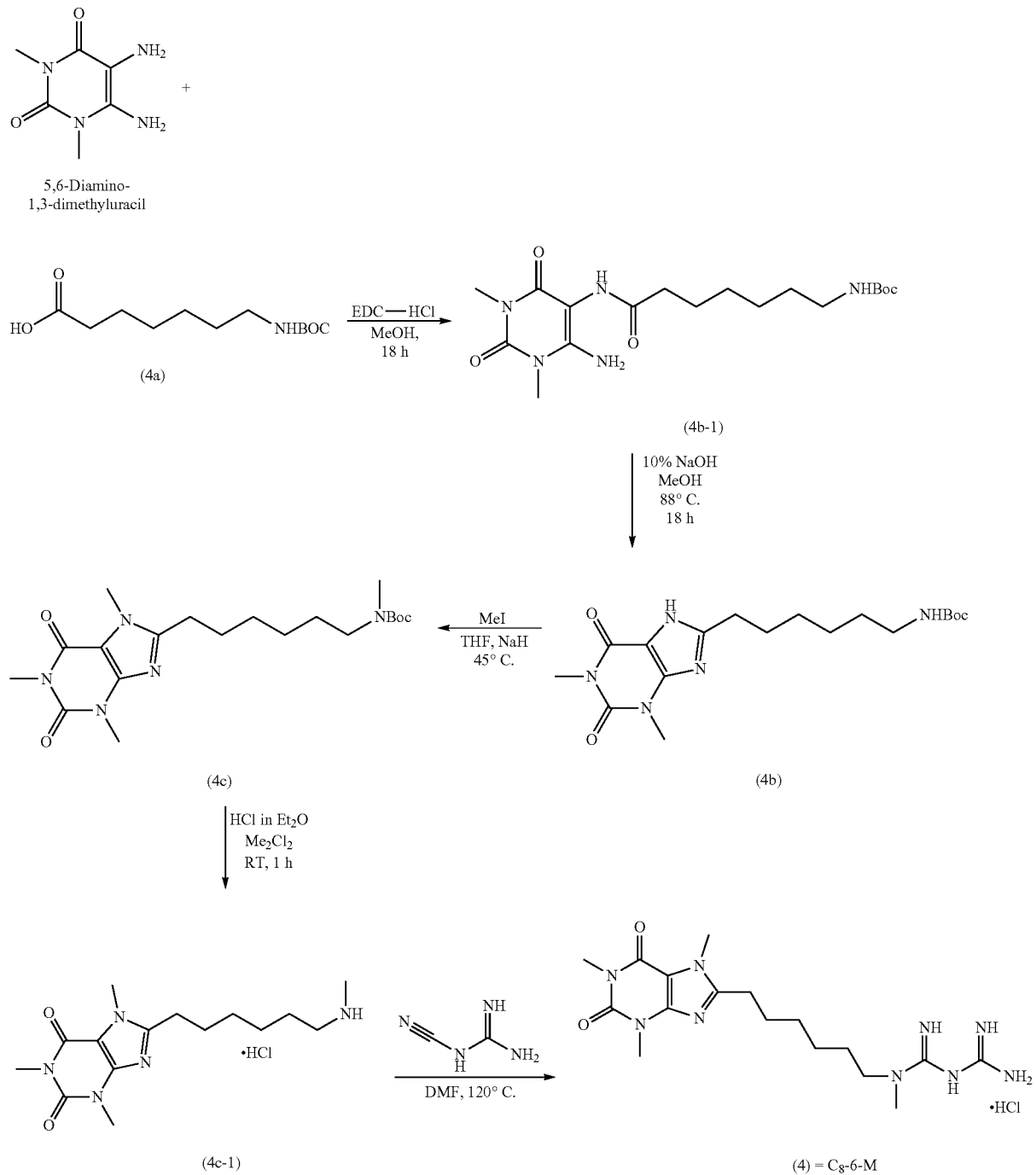

1,3-dimethyl-8-(2-(2-methylpropyl)-6-(N-methyl-N-hexyl-carbamyl))-xanthine, (4b)

(4b) was prepared by the same procedure as (3b) by substituting 7-(Boc-amino)enanthic acid (4a) for (3a). Yield: 0.31 g (47%). ¹H NMR (MeOD, 500 MHz, 22° C.): δ 3.57 (s, 3H), 3.38 (s, 3H), 3.03 (t, ³$J_{HH}$=6.9 Hz, 2H), 2.81 (t, ³$J_{HH}$=7.6 Hz, 2H), 1.89 (p, ³$J_{HH}$=7.3 Hz, 2H), 1.52-1.42 (m, 11H), 1.42-1.34 (m, 4H).

1,3,7-trimethyl-8-(2-(2-methylpropyl)-6-(N-methyl-N-hexyl-carbamyl))-xanthine, (4c)

(4b) (0.31 g, 0.38 mmol) was dissolved in anhydrous THF (8 mL) under N₂ and NaH (0.160 g, 4.0 mmol, 60% in mineral oil) was added followed by MeI (1 mL, 16 mmol). The vial was sealed and heated to 45° C. overnight. The mixture was allowed to cool to room temperature, H₂O (10 mL) was added to quench the reaction and the mixture was then extracted with $CH_2Cl_2$ (3×20 mL). The organic layers were combined and dried over $MgSO_4$. The solvent was removed under reduced pressure giving a colourless oil which was purified by column chromatography (70:30, Hexanes:EtOAc) giving (4c) as a white solid. Yield: 0.152 g (46%). $^1$H NMR ($CDCl_3$, 500 MHz, 22° C.): δ 3.87 (s, 3H), 3.53 (s, 3H), 3.36 (s, 3H), 3.16 (br. s, 2H), 2.78 (s, 3H), 2.68 (t, $^3J_{HH}$=7.8 Hz, 2H), 1.72 (p, $^3J_{HH}$=7.8 Hz, 2H), 1.48 (p, $^3J_{HH}$=7.6 Hz, 2H), 1.43-1.35 (m, 11H), 1.33-1.27 (m, 2H).

1,3,7-trimethyl-8-(6-(N-methyl-hexylamino))-xanthine, (4c-1)

(4c) (0.152 g, 37.3 mmol) was dissolved in $CH_2Cl_2$ (2 mL) followed by the addition of 1M HCl in ether (1 mL) and stirred until starting material was consumed as monitored by TLC. Once the reaction was complete the solvent was removed under reduced pressure giving pure (4c-1). Yield: 0.127 g (99%). $^1$H NMR (MeOD, 500 MHz, 22° C.): δ 4.01 (s, 3H), 3.54 (s, 3H), 3.38 (s, 3H), 3.02 (t, $^3J_{HH}$=7.6 Hz, 2H), 2.95 (t, $^3J_{HH}$=7.6 Hz, 2H), 2.72 (s, 3H), 1.84 (p, $^3J_{HH}$=7.4 Hz, 2H), 1.73 (p, $^3J_{HH}$=7.3 Hz, 2H), 1.56-1.46 (m, 4H).

$C_8$-6-M, (4)

(4c-1) (0.050 g, 0.15 mmol) was dissolved in DMF (2 mL) followed by the addition of dicyanodiamide (DCDA) (0.098 g, 1.16 mmol) and heated to 120° C. overnight. The solvent was then removed under reduced pressure. The crude mixture was purified via semi-preparatory HPLC using an Alltech C18 ODS-2 5μ (length=300 mm, ID=10 mm) column at 3 mL/min by running a gradient from 90:10 $H_2O$/ACN (v/v) to 70:30 $H_2O$/ACN (v/v) (t=8 minutes) to 60:40 $H_2O$/ACN (v/v)(t=14 minutes) to 10:90 $H_2O$/ACN (v/v) (t=20 minutes) to 10:90 $H_2O$/ACN (v/v) (t=22 minutes) to 90:10 $H_2O$/ACN (v/v) (t=24 minutes) to 90:10 $H_2O$/ACN (v/v) (t=30 minutes) all solvents contained 0.1% TFA and 0.1% $Et_3N$. The fractions containing (4) were combined and dried down leaving (4) dissolved in a TFA: $Et_3N$ complex. This mixture was dissolved in $CH_2Cl_2$ and 1 M HCl in ether (1 mL) was added causing (4) to precipitate from solution. The solution was filtered and the precipitate was washed with $CH_2Cl_2$ (3×1 mL) leaving $C_8$-6-$C_8$ (4) as a white solid. Yield: 0.014 g (22%).

$^1$H NMR ($D_2O$, 600 MHz, 50° C.): δ 4.21 (s, 3H), 3.84-3.72 (m, 5H), 3.60 (s, 3H), 3.49 (s, 3H), 3.18 (t, $^3J_{HH}$=7.28 Hz, 2H), 2.08-1.98 (m, 4H), 1.76-1.63 (m, 4H). $^{13}C\{^1H\}$ NMR ($CHCl_3$, 125 MHz): δ 156.09, 155.51, 155.36, 152.80, 152.53, 146.37, 107.85, 52.34, 37.30, 32.39, 30.53, 28.33, 28.13, 26.84, 26.35, 25.79, 25.55. HR-ESI-MS: 392.2503 ([M+H]$^+$, $C_{17}H_{30}N_9O_2$; calcd: 392.2522). Purity (HPLC): ≥99%, RT=7.25 min.

Scheme 7: Detailed Synthesis of (5) - $C_7$-6-$C_7$, (6) - $C_7$-6-N and (7) - $C_7$-6-I.

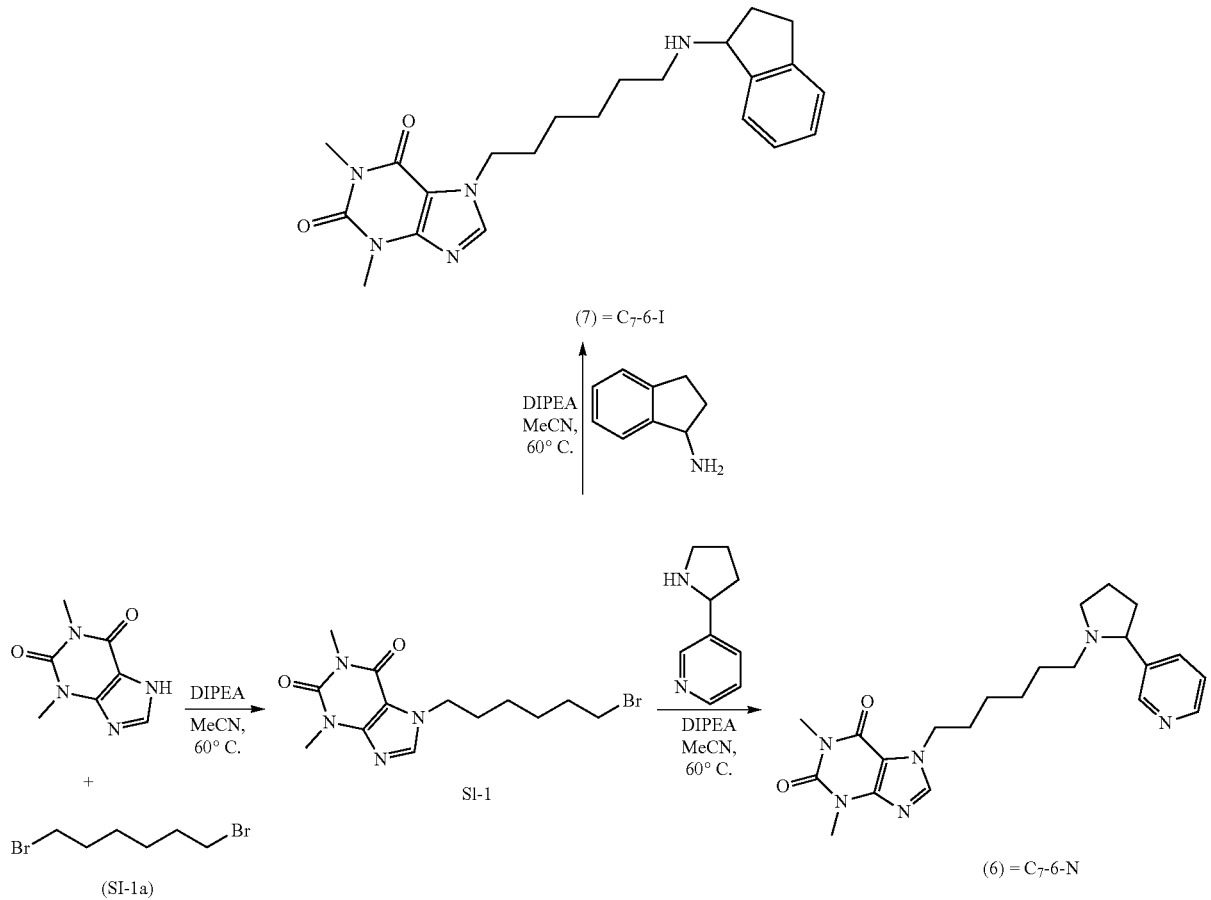

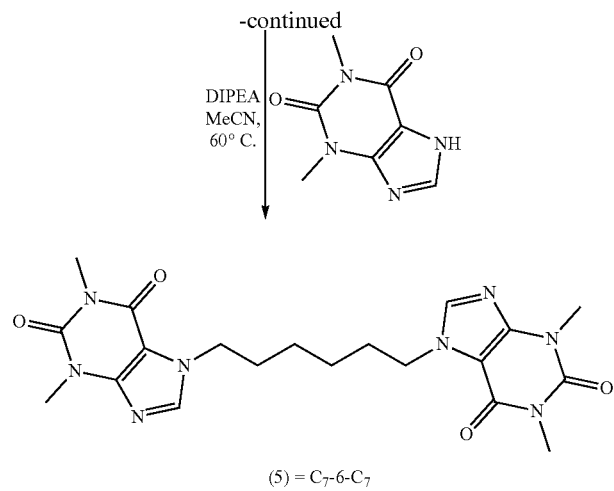

(5) = C₇-6-C₇

1,3-dimethyl-7-(6-(1-bromohexane))-xanthine, (SI-1)

Theophylline (1.0 g, 5.6 mmol) was added to anhydrous ACN (60 mL) under $N_2$, DIPEA (1.5 mL, 8.3 mmol) was added and stirred for 1 hour. 1,6-dibromohexane (SI-1a) (3.4 mL, 22 mmol, 4 equiv.) was then added drop-wise and the vial was sealed. The reaction vessel was heated to 60° C. and stirred overnight. The solution was allowed to cool to room temperature and $H_2O$ (10 mL) and sat $NaHCO_3$ (30 mL) was added to quench the reaction. The mixture was extracted with $CH_2Cl_2$ (3×40 mL), the organic layers were then combined and dried over $MgSO_4$. The solution was filtered, and the solvent was removed under reduced pressure followed by purification via column chromatography (97:3, EtOAc/MeOH (v/v)) giving (SI-1) as a white solid. Yield: 1.2 g (63%). ¹H NMR ($CDCl_3$, 500 MHz, 22° C.): δ 7.51 (s, 1H), 4.26 (t, $^3J_{HH}$=7.34 Hz, 2H), 3.57 (s, 3H), 3.39 (s, 3H), 3.64 (t, $^3J_{HH}$=6.7 Hz, 2H), 1.91-1.79 (m, 4H), 1.47 (p, $^3J_{HH}$=7.7 Hz, 2H), 1.32 (p, $^3J_{HH}$=7.7 Hz, 2H).

C₇-6-C₇, (5)

Theophylline (0.081 g, 0.45 mmol) was added to anhydrous ACN (10 mL) under $N_2$, DIPEA (0.12 mL, 0.68 mmol) was added and stirred for 1 hour. (SI-1) (0.171 g, 0.50 mmol) was then added in one portion and the vial was sealed. The reaction vessel was heated to 60° C. and stirred overnight. The solution was allowed to cool to room temperature and sat. $NaHCO_3$ (30 mL) was added. The mixture was extracted with $CH_2Cl_2$ (3×40 mL), the organic layers were then combined and dried over $MgSO_4$. The solution was filtered, and the solvent was removed under reduced pressure. Compound (5) was then purified via column chromatography (80:20, EtOAc/MeOH (v/v)) giving C₇-6-C₇ (5) as a white solid. Yield: 0.086 g (43%). ¹H NMR ($CDCl_3$, 500 MHz, 22° C.): δ 7.56 (s, 2H), 4.26 (t, $^3J_{HH}$=7.66 Hz, 4H), 3.58 (s, 6H), 3.39 (s, 6H), 1.91-1.78 (m, 4H), 1.38-1.33 (m, 4H). ¹³C{¹H} NMR ($CHCl_3$, 125 MHz): δ 155.14, 151.68, 148.97, 140.79, 106.96, 47.08, 30.72, 29.80, 28.03, 25.78. HR-ESI-MS: 443.2162 ([M+H]⁺, $C_{20}H_{27}N_8O_4$; calcd: 443.2155). Purity (HPLC): ≥99%, RT=9.09 min.

C₇-6-N, (6)

(6) was prepared by the same procedure as (5) by substituting (+/−)-nornicotine for theophylline giving C₇-6-N (6) as yellow oil. Yield: 0.016 g (27%). ¹H NMR (MeOD, 500 MHz, 22° C.): δ 8.51 (s, 1H), 8.43 (d, $^3J_{HH}$=4.9 Hz, 1H), 7.93 (s, 1H), 7.86 (dt, $^3J_{HH}$=7.8 Hz, $^4J_{HH}$=1.8 Hz, 1H), 7.42 (dd, $^3J_{HH}$=7.8 Hz, $^4J_{HH}$=4.9 Hz, 1H), 4.29 (t, $^3J_{HH}$=7.1 Hz, 2H), 3.56 (s, 3H), 3.4-3.36 (m, 5H), 2.50-2.42 (m, 1H), 2.31-2.21 (m, 2H), 2.16-2.10 (m, 1H), 2.02-1.87 (m, 2H), 1.87-1.80 (m, 2H), 1.75-1.66 (m, 1H), 1.49-1.42 (m, 2H), 1.38-1.21 (m, 4H). ¹³C{¹H} NMR (MeOD, 125 MHz): δ 154.94, 151.80, 148.86, 148.37, 147.54, 142.01, 139.81, 136.08, 123.95, 106.65, 67.59, 53.97, 53.28, 46.66, 34.36, 30.42, 28.78, 27.91, 26.93, 26.44, 25.68, 22.05. HR-ESI-MS: 411.2495 ([M+H]⁺, $C_{22}H_{31}N_6O_2$; calcd: 411.2508). Purity (HPLC): ≥96%, RT=6.86 min.

C₇-6-I, (7)

(7) was prepared by the same procedure as (5) by substituting (+/−)-1-aminoindan for theophylline. Column conditions were adjusted to 70:30, EtOAc/MeOH (v/v), giving C₇-6-I (7) as a yellow oil that contained an unknown impurity. This mixture was then dissolved in hot ether and allowed to cool overnight at −4° C. al owing (7) to crystallize out as a white solid. Yield: 0.021 g (36%). ¹H NMR (MeOD, 500 MHz, 22° C.): δ 7.96 (s, 1H), 7.38 (d, $^3J_{HH}$=7.3 Hz, 1H), 7.26-7.16 (m, 3H), 4.33 (t, $^3J_{HH}$=7.1 Hz, 2H), 4.27 (t, $^3J_{HH}$=6.6 Hz, 1H), 3.54 (s, 3H), 3.35 (s, 3H), 3.08-3.01 (m, 1H), 2.87-2.80 (m, 1H), 2.70-2.64 (m, 2H), 2.41-2.34 (m, 1H), 1.94-1.86 (m, 3H), 1.62-1.53 (m, 2H), 1.46-1.32 (m, 4H). ¹³C{¹H} NMR (MeOD, 125 MHz): δ 153.45, 150.26, 147.17, 142.15, 142.05, 140.51, 125.82, 124.36, 122.82, 122.32, 105.14, 61.17, 45.08, 44.82, 30.22, 28.85, 28.32, 27.28, 27.22, 25.37, 24.88, 24.17. HR-ESI-MS: 396.2407 ([M+H]⁺, $C_{22}H_{30}N_5O_2$; calcd: 396.2400). Purity (HPLC): ≥97%, 9.08

Scheme 8: Detailed Synthesis of (8) - C₇-6-M.

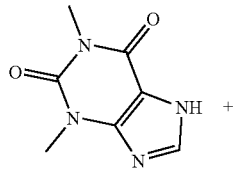 +

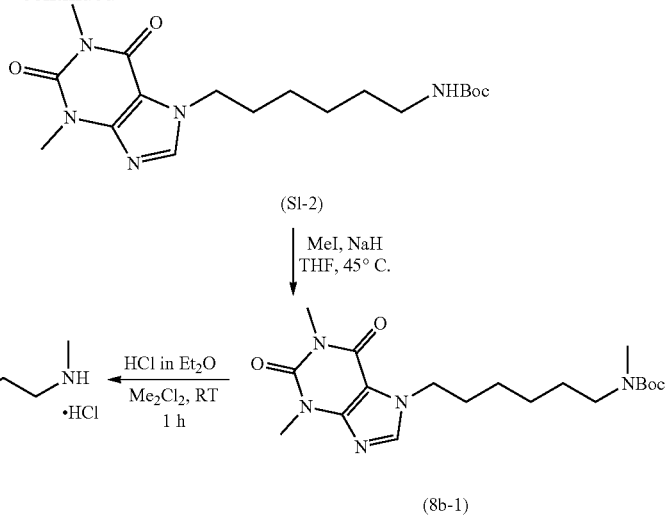
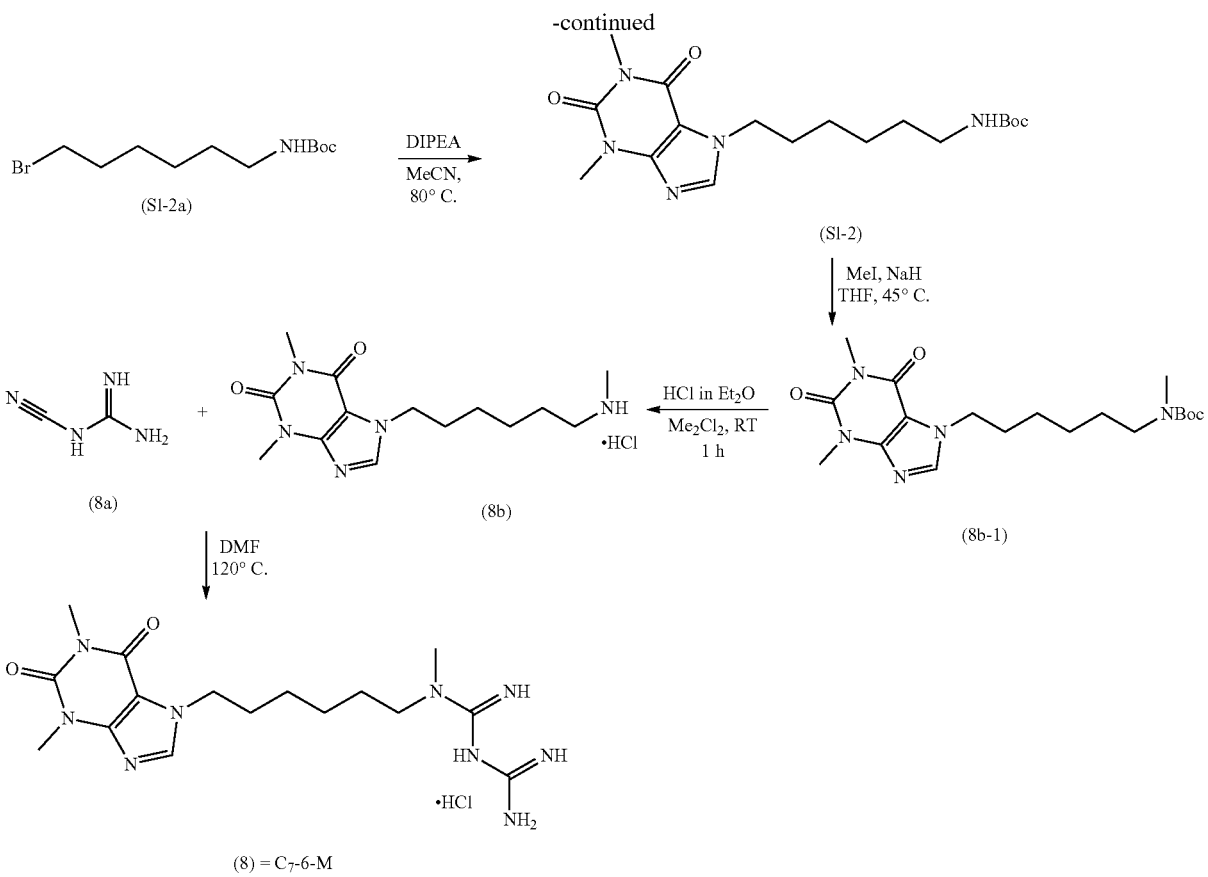

1,3-dimethyl-7-(2-(2-methylpropyl)-6-(N-methyl-N-hexyl-carbamyl))-xanthine, (SI-2)

(SI-2) was prepared by the same procedure as (SI-1) by substituting 6-(Boc-amino)hexyl bromide (SI-2a) for 1,6-dibromohexane (SI-1a). Yield: 0.213 g (52%). $^1$H NMR (CDCl$_3$, 500 MHz, 22° C.): δ 7.51 (s, 1H), 4.51 (br, s, 1H), 4.25 (t, $^3J_{HH}$=7.5 Hz, 2H), 3.57 (s, 3H), 3.38 (s, 3H), 3.11-3.01 (m, 2H), 1.85 (p, $^3J_{HH}$=7.2 Hz, 2H), 1.48-1.38 (m, 11H), 1.36-1.27 (m, 4H).

1,3-dimethyl-7-(2-(2-methylpropyl)-6-(N-methyl-N-hexyl-carbamyl))-xanthine, (8b-1)

(8b-1) was prepared by the same procedure as (4c) by substituting (SI-2) for (4b). Yield: 0.136 g (62%). $^1$H NMR (CDCl$_3$, 500 MHz, 22° C.): δ 7.55 (s, 1H), 4.28 (t, $^3J_{HH}$=7.0 Hz, 2H), 3.60 (s, 3H), 3.42 (s, 3H), 3.18 (br. s, 2H), 2.82 (s, 3H), 1.94-1.84 (m, 2H), 1.53-1.41 (m, 11H), 1.38-1.28 (m, 4H).

1,3-dimethyl-7-(6-(N-methyl-hexylamino))-xanthine, (8b)

(8b) was prepared by the same procedure as (4c-1) by substituting (8b-1) for (4c). Yield: 0.136 g (62%). $^1$H NMR (MeOD, 500 MHz, 22° C.): δ 8.56 (s, 1H), 4.45 (t, $^3J_{HH}$=7.5 Hz, 2H), 3.58 (s, 3H), 3.42 (s, 3H), 3.38 (s, 3H), 3.02 (t, $^3J_{HH}$=7.5 Hz, 2H), 2.73 (s, 3H), 2.02-1.91 (m, 2H), 1.77-1.69 (m, 2H), 1.52-1.38 (m, 4H).

C$_7$-6-M, (8)

(8) was prepared by the same procedure as (4) by substituting (8b) for (4c-1), giving C$_7$-6-M (8) as a white solid. Yield: 0.011 g (18%). $^1$H NMR (D$_2$O, 600 MHz, 50° C.): δ 8.30 (s, 1H), 4.60 (t, $^3J_{HH}$=7.7 Hz, 2H), 3.81 (s, 3H), 3.79 (t, $^3J_{HH}$=6.90 Hz, 2H), 3.62 (s, 3H), 3.47 (s, 3H), 2.14 (p, $^3J_{HH}$=6.90 Hz, 2H), 2.00-1.93 (m, 2H), 1.68-1.59 (m, 4H). $^{13}$C{$^1$H} NMR (CHCl$_3$, 125 MHz): δ 156.30, 155.42, 152.97, 152.90, 148.72, 143.04, 107.52, 52.16, 47.40, 37.16, 30.28, 29.99, 28.35, 26.23, 25.32, 25.28. HR-ESI-MS: 378.2379 ([M+H]$^+$, C$_{16}$H$_{28}$N$_9$O$_2$; calcd: 378.2366). Purity (HPLC): ≥96%, RT=6.95 min.

Example 2.0—Experimental Methods

The bifunctional molecules were characterized by four different methods. First, they were screened by nanopore analysis which has been shown to be a useful technique for studying conformational changes in intrinsically disordered proteins.[41-43] In this technique, alpha-synuclein is electrophoretically driven towards a pore which is monitored by a patch-clamp apparatus. There is a large change in the blockade current if alpha-synuclein translocates through the pore but if a compound causes a loop conformation the blockade current is significantly smaller. If the compound causes a more compact conformation, then the alpha-synuclein can no longer translocate and it simply bumps into the pore giving rise to a very small change in the blockade current.[44-46]

Second, the binding constants were measured by isothermal titration calorimetry (ITC) in order to demonstrate that the dimer drugs had an increased binding constant compared to the monomers.

Third, the drugs were assayed in a yeast model of Parkinson's Disease, which expresses an alpha-synuclein-Green Fluorescent Protein (AS-GFP) construct under the control of a galactose promoter. This yeast strain has previously been shown to provide a druggable target for studying the toxicity of alpha-synuclein.[47-49] In the presence of galactose the cells die due to the build up of alpha-synuclein-GFP, which can be visualized as large foci by fluorescent microscopy. For example, it was recently shown that an N-aryl benzimidazole (NAB) could reverse the accumulation of vesicular alpha-synuclein foci.[48]

Fourth, the bifunctional compound $C_8$-6-I (3) was evaluated at two different doses in a rat model having increased expression of alpha-synuclein.

Nanopore analysis and isothermal titration calorimetry were performed as described previously.[21,54]

Yeast Growth Curves:

Construction of the 1AS and 2AS strains has been described in detail previously.[55] Strains were grown in YPD supplemented with 30 μg/ml of all amino acids. The $OD_{600}$ was adjusted to 0.05 in drop-out media (no uracil) at 30° C. Drugs were dissolved in methanol at 0.01 micromolar, 0.1 micromolar, 1 micromolar or 10 micromolar followed by addition of 100 micromolar or 5 mM galactose to a final volume of 10 mL. The $OD_{600}$ was taken every two hours for 24 hours in triplicate.

Fluorescence Microscopy:

For Analysis of AS-GFP distribution, the 2AS strain was grown overnight in drop-out media. After normalization of culture density, galactose was administered to a final concentration of 5 mM. Fluorescence images were obtained at zero time, 3 hours, 6 hours, 9 hours and 12 hours. For the yeast recovery assay, yeast cells were obtained after 6 hours induction with 5 mM galactose concentration, washed in galactose free media and the compounds were added to a final concentration of 1 micromolar in a 2 mL reaction mixture. The culture was incubated at 30° C. for 3, 6, and 9 hour intervals. Images were obtained at each interval using an Olympus Infinity (BX51) fluorescence microscope at 100× magnification.

Studies in Rat Model Having Increased Alpha-Synuclein Expression:

male Sprague-Dawley rats are used (200 g-300 g). All animals are handled ethically following approved protocols. For the first round of studies, rats are divided into five treatment groups:

(a) DMSO/Saline (Control)
(b) Alpha-synuclein inducing agent (ASIA)
(c) Alpha-synuclein inducing agent (ASIA) plus selective ASIA antagonist
(d) Alpha-synuclein inducing agent (ASIA) plus 1-aminoindan
(e) Alpha-synuclein inducing agent (ASIA) plus 2-aminoindan Rats are subjected to 7-day chronic injection of 3 mg/kg of each test compound, and a forced swim test is conducted after the seventh day to measure motor deficits. 1-aminoindan is tested as a monomer that binds to alpha-synuclein and is neuroprotective, while 2-aminoindan is tested as a molecule that binds to alpha-synuclein but does not prevent its aggregation, and is predicted to be neurotoxic. For a second round of studies, rats are divided into four treatment groups, and the same experiments are repeated:

(a) DMSO/Saline (Control)
(b) Alpha-synuclein inducing agent (ASIA)
(c) Alpha-synuclein inducing agent (ASIA) plus $C_8$-6-I (3) (3 mg/kg (3))
(d) Alpha-synuclein inducing agent (ASIA) plus $C_8$-6-I (3) (5 mg/kg (3))

Immunohistochemistry:

Tissue sections of substantia nigra from each of the treatment groups in the rat studies were evaluated for the presence of tyrosine hydroxylase, DNA (using the nuclear stain DAPI) and alpha-synuclein using immunohistochemistry. After behavioural tests were completed, the rats were euthanized, perfused and fixed in 4% paraformaldehyde. 40 μm brain slices were utilized for the immunohistochemistry procedure. Anti-Tyrosine Hydroxylase—a primary antibody for tyrosine positive neurons, host species rabbit, Millipore, Sigma Aldrich. DAPI—nuclear stain already pre-conjugated (NucBlue Fixed Cell Stain ReadyProbe reagent, Thermo Fisher Scientific). Anti-Alpha Synuclein—primary antibody for Anti-Synuclein, host species mouse, Abcam. Primary antibodies were diluted 1:500. Alexa Fluoro 488 Donkey anti-rabbit IgG—secondary antibody with fluorescent tag, Invitrogen, Thermo Fisher Scientific. Alexa Fluoro 594 Goat anti-mouse IgG—secondary antibody with fluorescent tag, Life Technologies, Thermo Fisher Scientific. Secondary antibodies were diluted 1:1000. Thioflavin S—stain for alpha-synuclein aggregates, Sigma Aldrich. Thioflavin S stock concentration at 5 mg/ml. Final dilution 1:100.

Tyrosine hydroxylase is a marker for dopaminergic neurons and is used to confirm that the desired cells are being imaged. DAPI (4',6-diamidino-2-phenylindole) is a stain that binds to A-T rich regions in DNA, and is used to identify cell nuclei. Thioflavin S is used to stain aggregated proteins such as amyloid plaques. A higher level of staining with thioflavin S is indicative of a higher degree of protein aggregation.

Forced Swim Test:

The forced swim test is carried out by immersing the rat in water that is sufficiently deep to force the rat to swim. The forced swim test is scored based on the following criteria:

| Vigor | Success |
|---|---|
| 3—swim with four limbs | 3—entire head above water |
| 2.5—occasionally float | 2.5—ears below water |
| 2—floating more than swimming | 2—eyes below water |
| 1.5—occasionally swimming | 1.5—entire head below water 3 sec |
| 1—occasionally swimming with hind limbs | 1—entire head below water 6 sec |
| 0—no use of limbs | 0—in bottom of tank more than 10 sec |

Vigor and success are measures of motor function. Immobility is thought to be a measure of depression.[59] Based on videos of the forced swim test, the amount of time that each rat was motionless was calculated as a form of scoring depression for each treatment. Statistical analysis was carried out using an ordinary one-way ANOVA and Tukey multiple comparisons test.

Example 3.0—Characterization of Compounds

Figure 2:
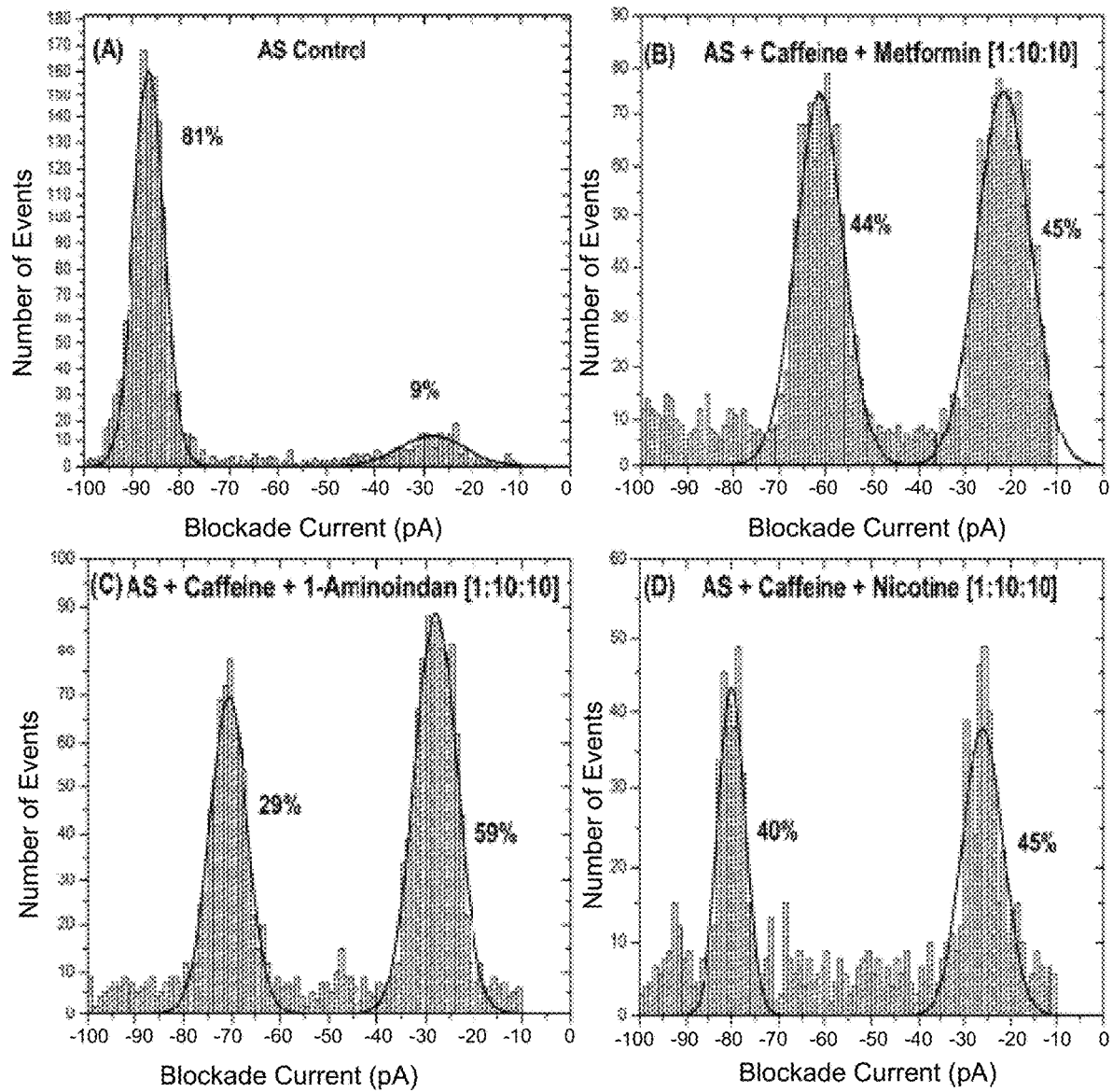
FIG. 2 shows nanopore analysis blockade current histograms of alpha-synuclein (AS). Panel (A) shows control (no treatment). Panel (B) shows caffeine+metformin. Panel (C) shows caffeine+(R,S)-1-aminoindan. Panel (D) shows caffeine+(R,S)-nicotine.

Example 3.1—Characterization of Compound Binding to Alpha-Synuclein by Nanopore Analysis and ITC In the absence of any compound, the control blockade current histogram for alpha-synuclein at 1 micromolar gives a major translocation peak at −86 pA and a minor bumping peak about −27 pA (FIG. 2, panel A).

The effect of adding two compounds in combination at 10 micromolar each is shown in FIG. 2, panels B, C and D. It was shown previously that at this concentration caffeine alone gives a major peak at about −76 pA and for metformin alone the major peak is at about −65 pA.[21,40] The combination of caffeine and metformin gives a different profile with a translocation peak at −60 pA and a large bumping peak at about −20 pA, neither of which is seen in the presence of a single compound. Since each peak represents a different conformation, without being bound by theory, the two compounds probably have non-overlapping binding sites. Similarly, combinations of caffeine with either (R,S)-1-aminoindan or (R,S)-nicotine (FIG. 2, panels C and D) give new profiles, again suggesting that the two compounds can bind simultaneously to alpha-synuclein.

Figure 3:
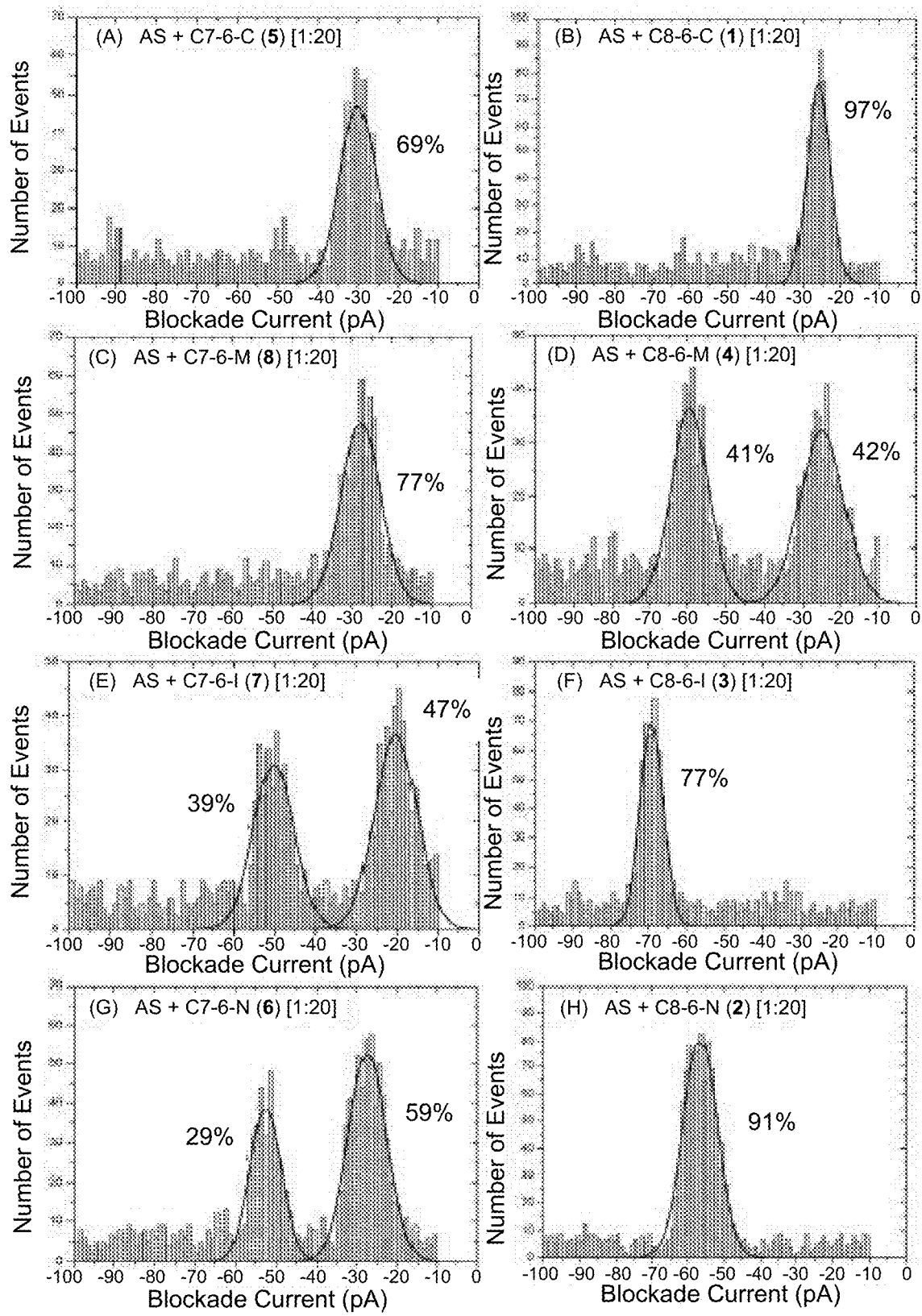
FIG. 3 shows blockade current histograms for 1 micromolar alpha-synuclein with 20 micromolar compound. Panel (A) $C_7$-6-$C_7$ (5), panel (B) $C_8$-6-$C_8$ (1), panel (C) $C_7$-6-M (8), panel (D) $C_8$-6-M (4), panel (E) $C_7$-6-I (7), panel (F) $C_8$-6-I (3), panel (G) $C_7$-6-N (6), and panel (H) $C_8$-6-N (2).

Nanopore analyses of eight exemplary bifunctional molecules are shown in FIG. 3 with a concentration of 20 micromolar (with 1 micromolar alpha-synuclein). It is clear that all of the bifunctional molecules bind well since the translocation peak at −86 pA given by alpha-synuclein alone is absent in every case and most of the profiles are significantly different. $C_7$-6-$C_7$ (5), $C_8$-6-$C_8$ (1) and $C_7$-6-M (8) (FIG. 3, panels A, B and C) give predominantly bumping peaks with the majority of events having blockade currents <−30 pA. Only $C_8$-6-I (3) and $C_8$-6-N (2) (FIG. 3, panels F and H) do not have a significant bumping peak although the conformations of the compound/alpha-synuclein complexes are different since the major peaks are at −68 pA and −55 pA respectively. Based on these results, it is predicted that $C_8$-6-I (3) and $C_8$-6-N (2) may be neuroprotective since even at high concentrations they do not cause alpha-synuclein to adopt a compact conformation.

The binding constants (Ka) for the interaction with alpha-synuclein were measured by ITC and the results are summarized in Table 1 together with those for the monomers of caffeine, 1-aminoindan, nicotine and metformin. The best-fit values of n, the number of binding sites, is also included in Table 1. Only one of the bifunctional molecules has a higher binding constant (Ka) than the parent monomer. The $C_8$-6-$C_8$ (1) dimer has a Ka=$2 \times 10^8$ M$^{-1}$ which is two orders of magnitude larger than the Ka for caffeine alone ($7 \times 10^5$ M$^{-1}$). The Ka for $C_7$-6-$C_7$ (5) is identical to caffeine, whereas for other bifunctional molecules, such as $C_7$-6-M (8), $C_8$-6-M (4), $C_8$-6-I (3) and $C_8$-6-N (2), the Ka for the bifunctional molecule is lower than for either monomer. Without being bound by theory, this suggests that there may be interference between one monomer and the other when they are linked in some constructs.

Without being bound by theory, the inventors postulate that it is unlikely that the 6 carbon linker is interfering with the caffeine binding site because of the large increase in Ka for $C_8$-6-$C_8$ (1) as compared with caffeine monomers, but it may not be sterically tolerated when linked to other monomers.

The number of binding sites for caffeine homodimers or for caffeine linked to metformin was not unity. For $C_7$-6-$C_7$ (5) the value of n was 2, i.e. 2 bifunctional molecules to 1 alpha-synuclein molecule. In contrast, for $C_8$-6-$C_8$ (1), n=0.25, or 1 bifunctional molecule to 4 alpha-synuclein molecules, and for $C_7$-6-M (8) and $C_8$-6-M (4) n=0.5 corresponding to 1 bifunctional molecule to 2 alpha-synuclein molecules. The latter might be expected if both halves of the bifunctional molecule bound to different alpha-synuclein molecules. In all other cases n=1, which would be expected if 1 bifunctional molecule bound simultaneously to the N- and C-terminus of alpha-synuclein causing a loop conformation. $C_8$-6-I (3) and $C_8$-6-N (2) were also analysed at lower ionic strength (100 mM KCl) and the Ka's increased approximately 10-fold for a 10-fold decrease in ionic strength (Table 1). Thus, without being bound by theory, the charged I and N moieties are probably involved in ionic interactions with alpha-synuclein. As expected, the binding constant of $C_8$-6-$C_8$ (1) does not increase as the ionic strength is decreased because this bifunctional molecule is not charged.

TABLE 1

Binding constants. Ka was measured by ITC in 1.0M KCl unless otherwise stated. The number of binding sites is the number of bifunctional molecules (or monomers, as applicable) per alpha-synuclein molecule which gave the best fit to the binding isotherm.

| Compound # | Compound | Ka M$^{-1}$ | # of Binding sites |
|---|---|---|---|
| (1) | $C_8$-6-$C_8$ | $2.8 \times 10^5$ | 0.25 |
| (2) | $C_8$-6-N | $4.3 \times 10^4$ | 1 |
| (3) | $C_8$-6-I | $5.3 \times 10^4$ | 1 |
| (4) | $C_8$-6-M | $4.1 \times 10^4$ | 0.5 |
| (5) | $C_7$-6-$C_7$ | $7.2 \times 10^5$ | 2 |
| (6) | $C_7$-6-N | $5.1 \times 10^6$ | 1 |
| (7) | $C_7$-6-I | $2.6 \times 10^6$ | 1 |
| (8) | $C_7$-6-M | $2.5 \times 10^4$ | 0.5 |
| (102) | Caffeine | $7.6 \times 10^5$ | 1 |
| (107) | Metformin | $9.2 \times 10^6$ | 1 |
|  | R-Aminoindan | $1.0 \times 10^6$ | 1 |
|  | S-Aminoindan | $3.1 \times 10^6$ | 1 |
|  | R-Nicotine | $1.4 \times 10^6$ | 1 |
|  | S-Nicotine | $4.0 \times 10^5$ | 1 |
| (2) | $C_8$-6-Nin 100 mM KCl | $4.8 \times 10^5$ | 1 |
| (3) | $C_8$-6-I in 100 mM KCl | $5.6 \times 10^5$ | 1 |
| (1) | $C_8$-6-$C_8$ in 100 mM KCl | $1.8 \times 10^8$ | 0.25 |

Figure 4A:
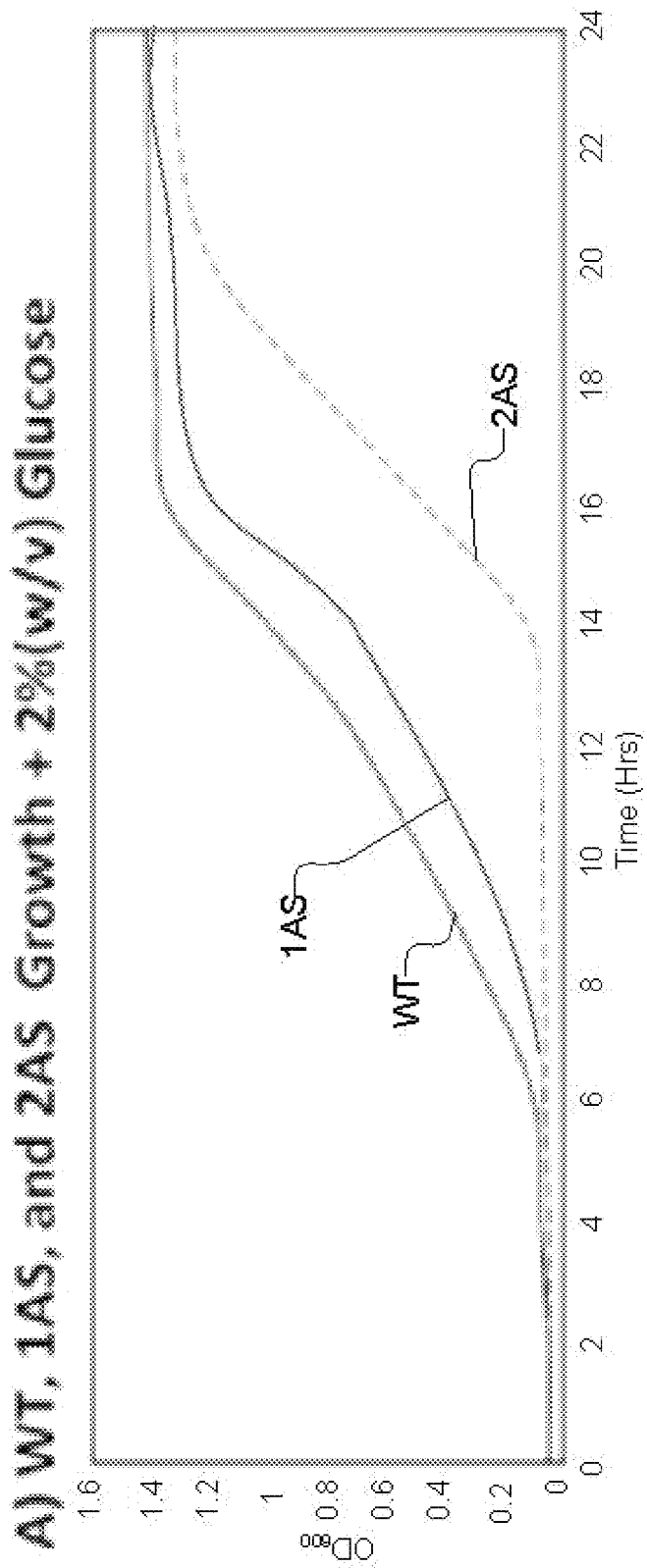
FIGS. 4A, 4B and 4C show yeast growth monitored at $OD_{600}$ over 24 hours.

Example 3.2—Characterization of Compounds in a Yeast Model for Parkinson's Disease—Growth The effect of the bifunctional molecules on three strains of yeast were investigated: WT (wild type), 1AS which has 1 copy of the AS-GFP gene, and 2AS which has 2 copies of the AS-GFP gene under control of the galactose promoter.[47] Standard growth curves in the absence of drug or galactose are shown in FIG. 4A. It is clear that both 1AS and 2AS have growth deficits compared to the WT, presumably because some AS-GFP is made even in the absence of galactose.[47,52]

Figure 4B:
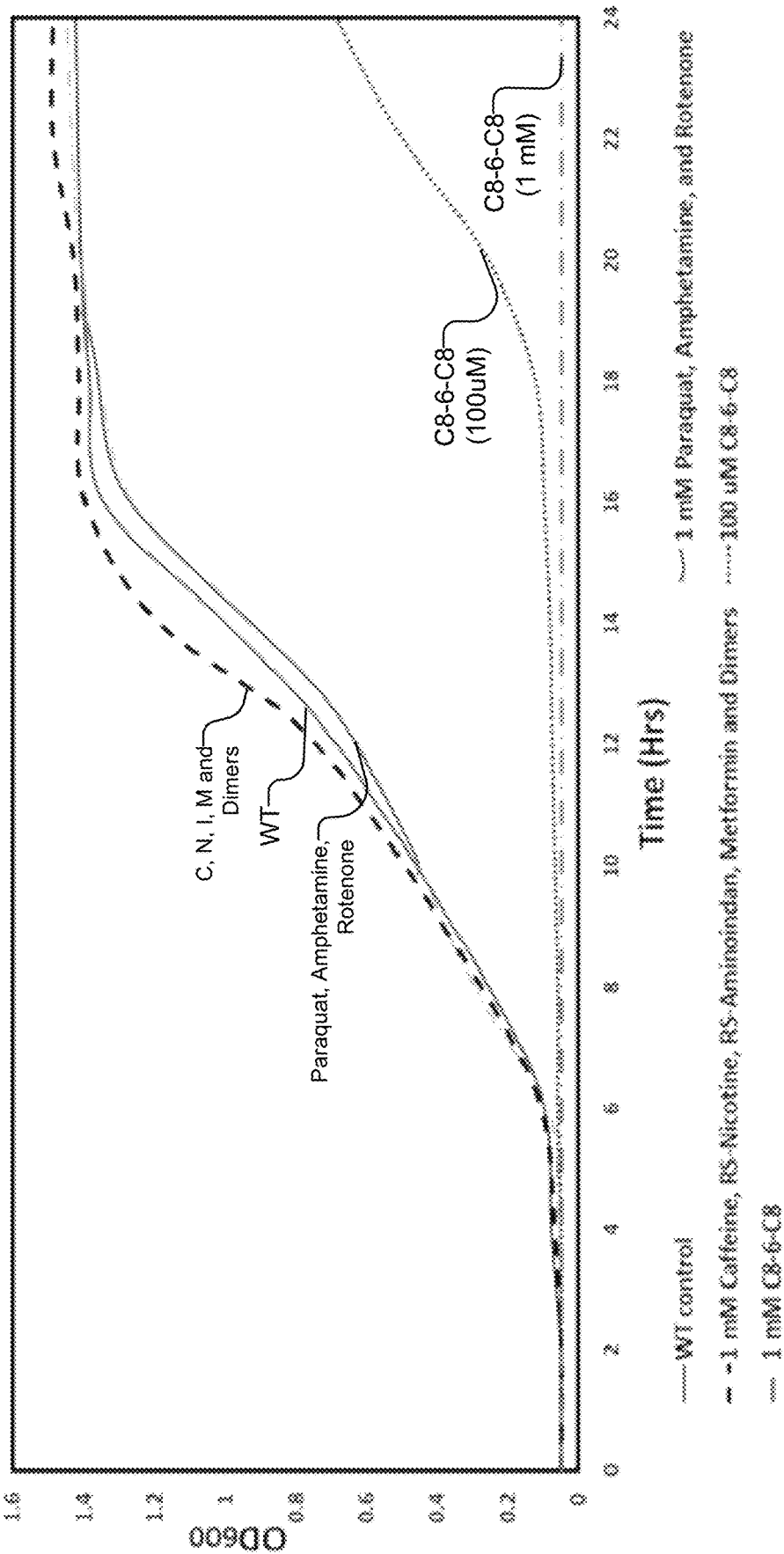

Except for $C_8$-6-$C_8$ (1), addition of 1 mM of the dimers to the WT has no significant effect on growth (FIG. 4B). However, $C_8$-6-$C_8$ (1) is toxic even at 100 micromolar. Paraquat, rotenone and amphetamine were also included in this study because their binding to alpha-synuclein has been linked to neurotoxicity and an increased incidence of Parkinson's Disease.[22-24] However, in the absence of alpha-synuclein there is no evidence of toxicity for these three compounds at 1 mM (FIG. 4B).

Figure 4C:
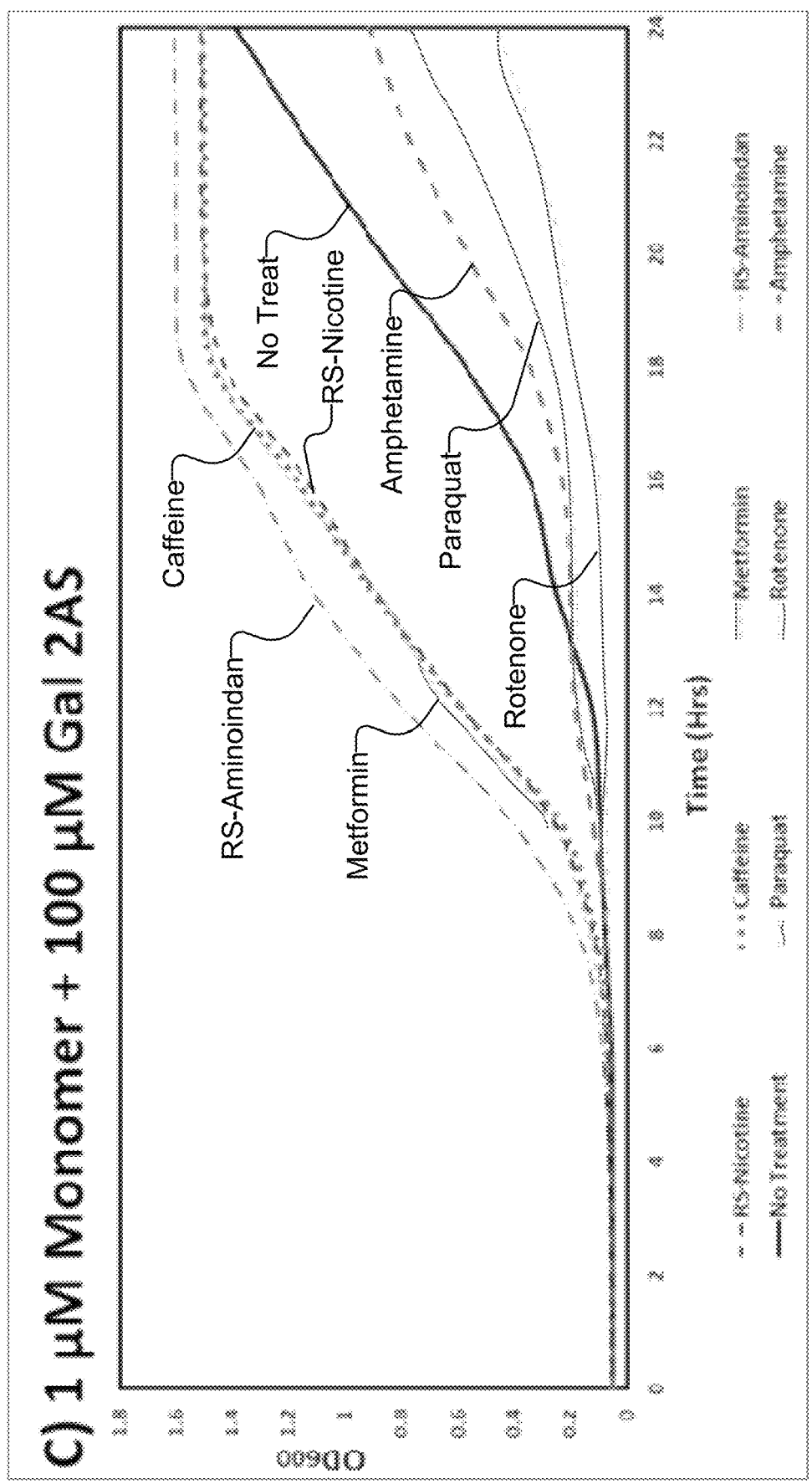

Induction of AS-GFP in the 1AS strain with 100 micromolar galactose caused only small changes in growth rates but large changes were observed with the 2AS strain (results shown in FIG. 4C). First, growth of 2AS is reduced compared to 2AS without galactose (compare FIG. 4A vs. FIG. 4C) confirming that, at these levels, alpha-synuclein is toxic. Second, paraquat, rotenone and amphetamine cause significant reduction of growth even at 1 micromolar concentration, demonstrating that the induction of alpha-synuclein is clearly linked to their toxicity. Third the addition of caffeine, (R,S)-1-aminoindan, (R,S)-nicotine or metformin (monomeric compounds) at 1 micromolar results in a rate of growth which is similar to that shown by the WT strain. Without being bound by theory, the inventors hypothesize that these compounds, which are known to be neuroprotective, are binding to alpha-synuclein and rescuing the yeast cells from alpha-synuclein-mediated toxicity.

Figure 5A:
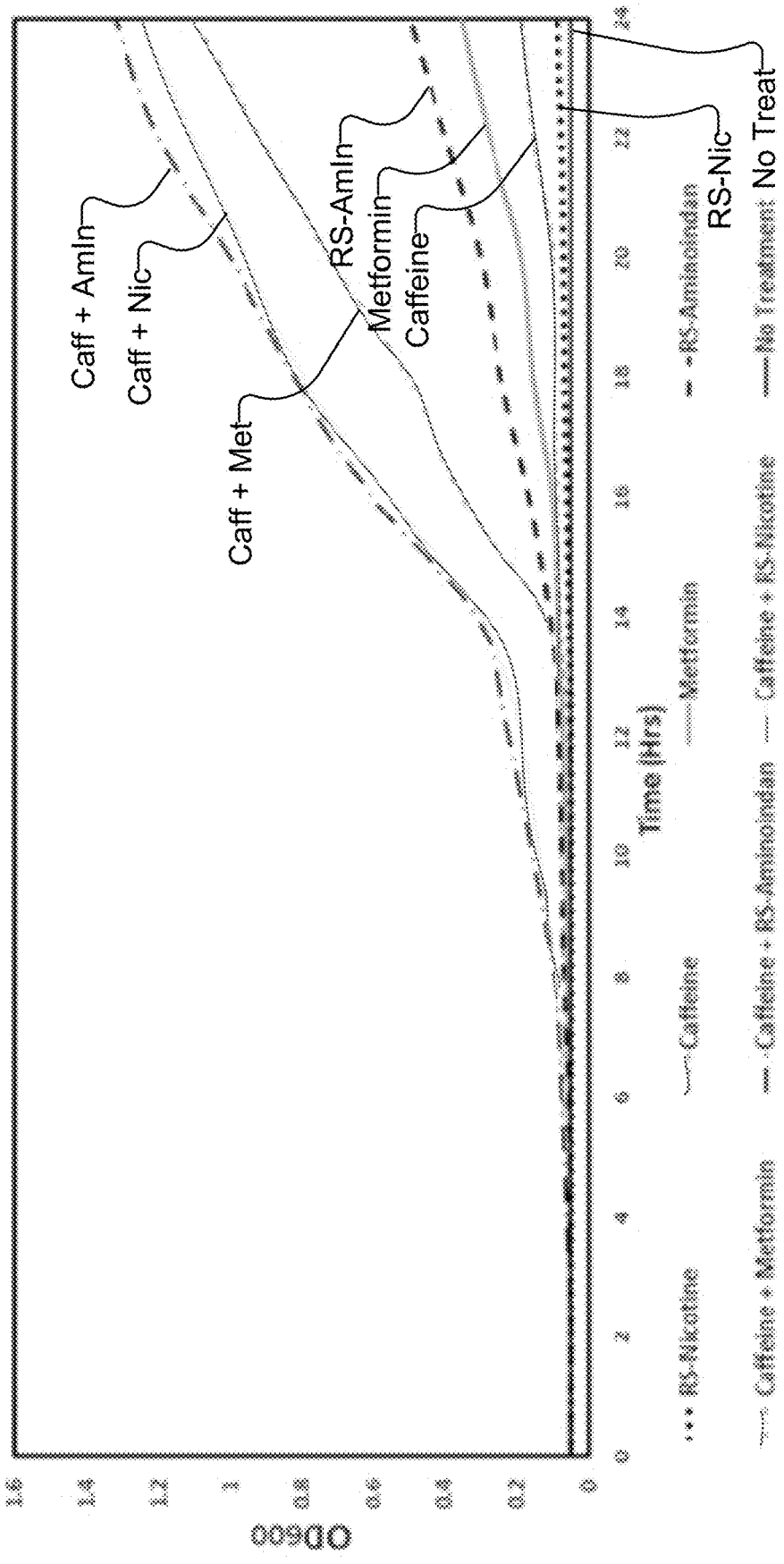
FIGS. 5A, 5B, 5C and 5D show growth of yeast strain 2AS monitored at $OD_{600}$ over 24 hours.
Figure 5B:
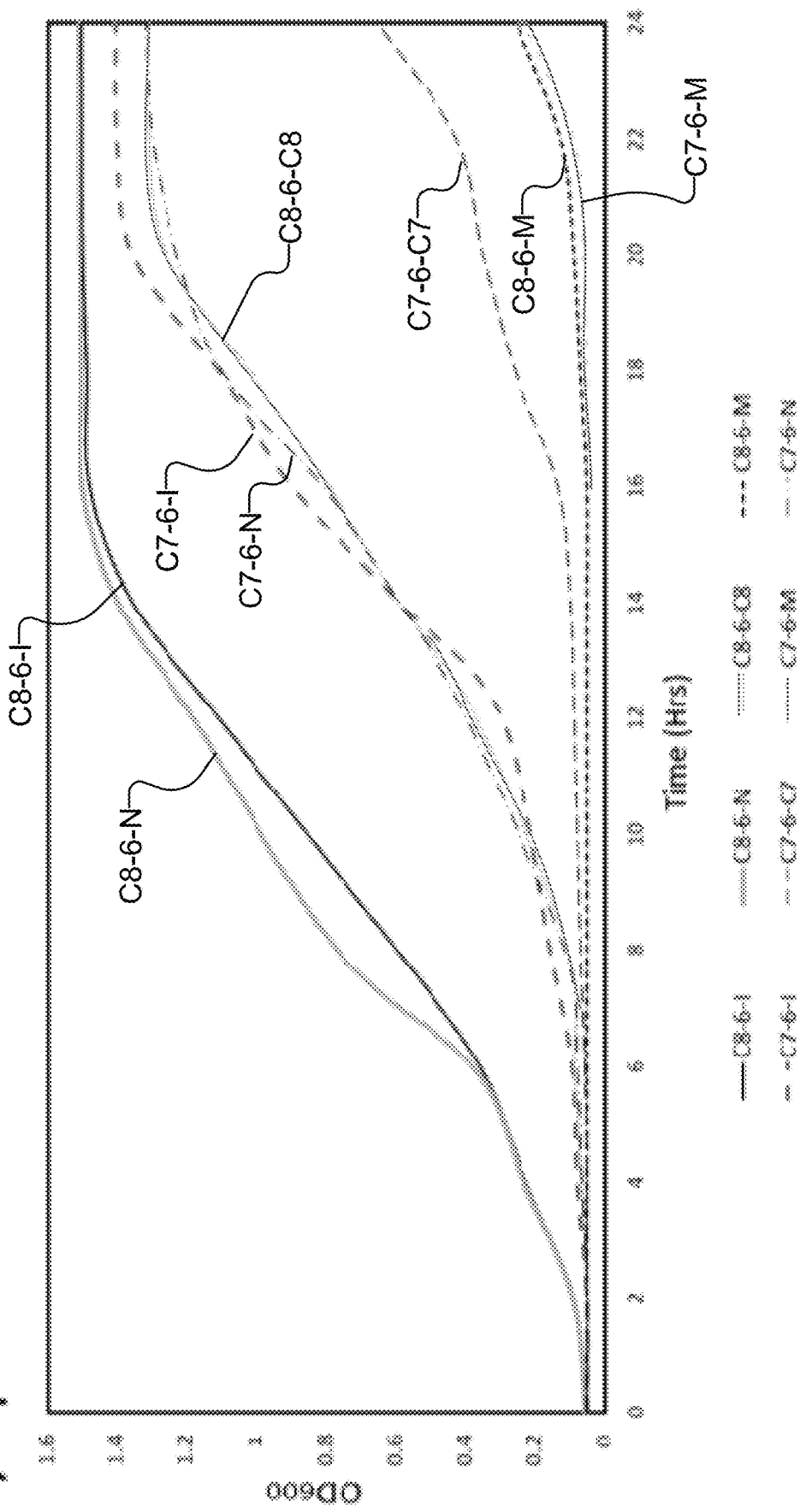

Preliminary results at 1 micromolar and 100 micromolar galactose showed that all of the exemplary bifunctional molecules tested allowed normal growth of the 2AS strain and, therefore, the concentration of galactose was increased to 5 mM to give maximum expression of AS-GFP. As shown in FIG. 5A and FIG. 5B, increasing AS-GFP expression allowed the tested compounds to be distinguished as a large variation in growth rate between the different treatments was observed. In the absence of compound, no growth was observed demonstrating that the toxicity of alpha-synuclein is concentration dependent and the addition of the monomeric compounds showed only small improvements.

To assess whether a combination of monomers could produce a more than summative effect, the inventors treated the yeast cells with caffeine together with metformin, (R,S)-Nicotine or (R,S)-1-aminoindan at 1 micromolar (FIG. 5A). All of the treatments involving combinations of monomers were able to rescue growth, although lag phases for growth rescue were greater than 6 hours. For the bifunctional molecules (FIG. 5B), $C_7$-6-$C_7$ (5), $C_7$-6-M (8) and $C_8$-6-M (4) showed marginal growth rescue even after 24 hours, while $C_7$-6-I (7), $C_7$-6-N (6) and $C_8$-6-$C_8$ (1) showed a lag of about 6 hours before reaching the growth plateau. In contrast, the growth of $C_8$-6-I (3) and $C_8$-6-N (2) was essentially normal.

These results support that some of the bifunctional molecules are much more effective at rescuing the growth of the 2AS yeast model of Parkinson's Disease compared to the corresponding monomeric compounds or combinations of monomeric compounds.

Figure 5C:
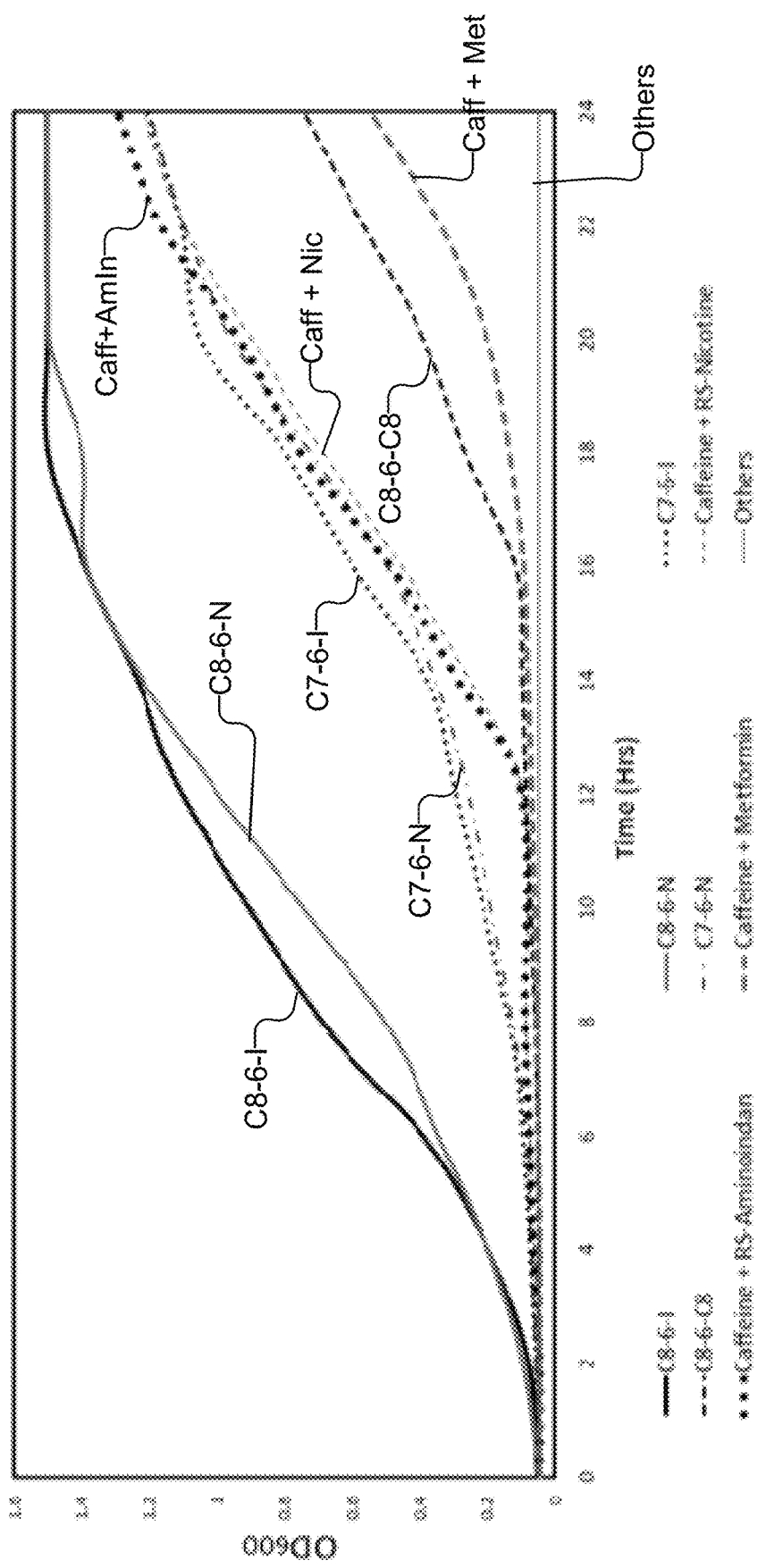
Figure 5D:
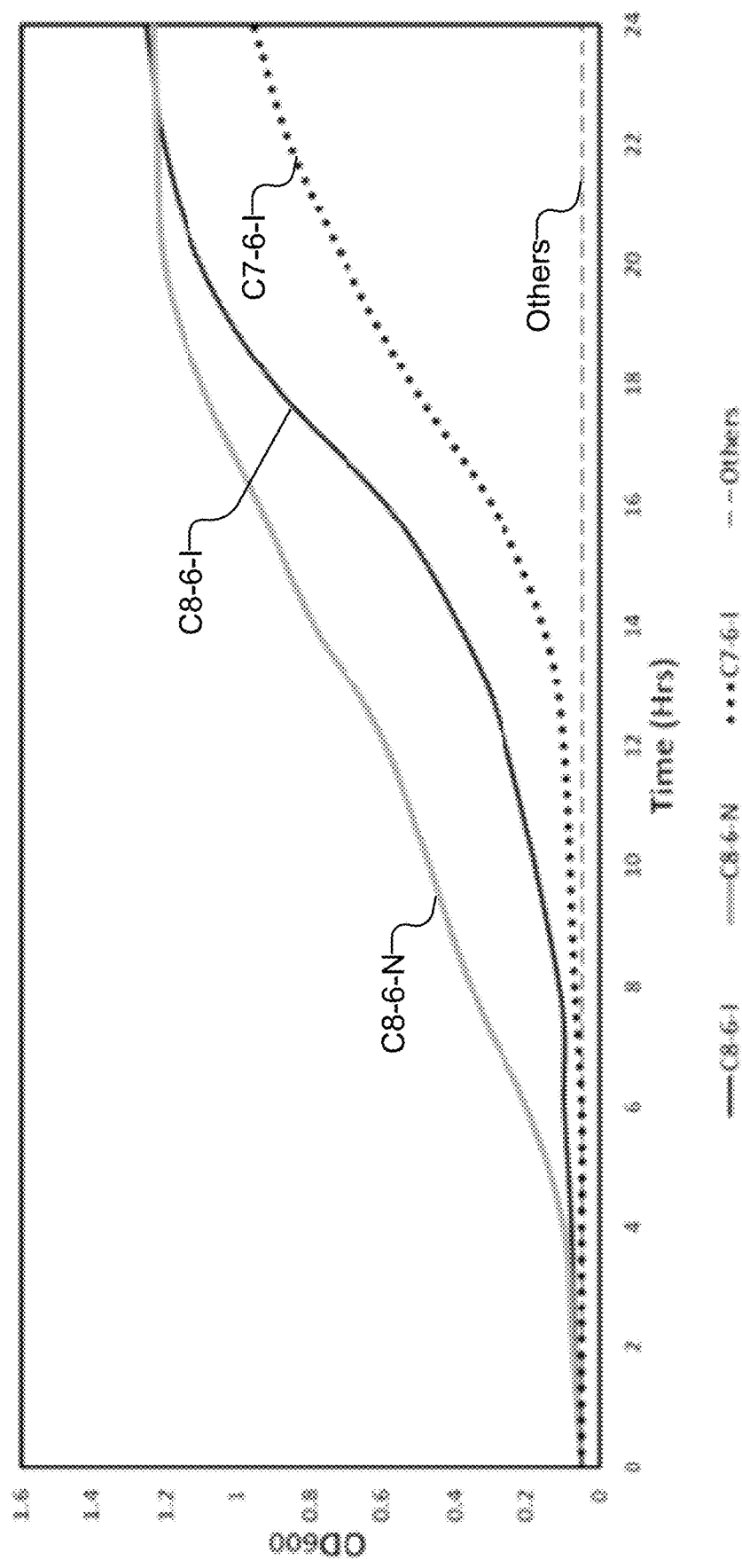

To more clearly distinguish between the effectiveness of the different bifunctional molecules, the inventors treated the yeast cells with lower concentrations of compound, specifically 0.1 micromolar and 0.01 micromolar. At these lower concentrations the same trends are evident (FIG. 5C) and at 0.01 μM (FIG. 5D) only $C_8$-6-I (3), $C_8$-6-N (2) and $C_7$-6-I (7) allowed any growth.

Figure 6:
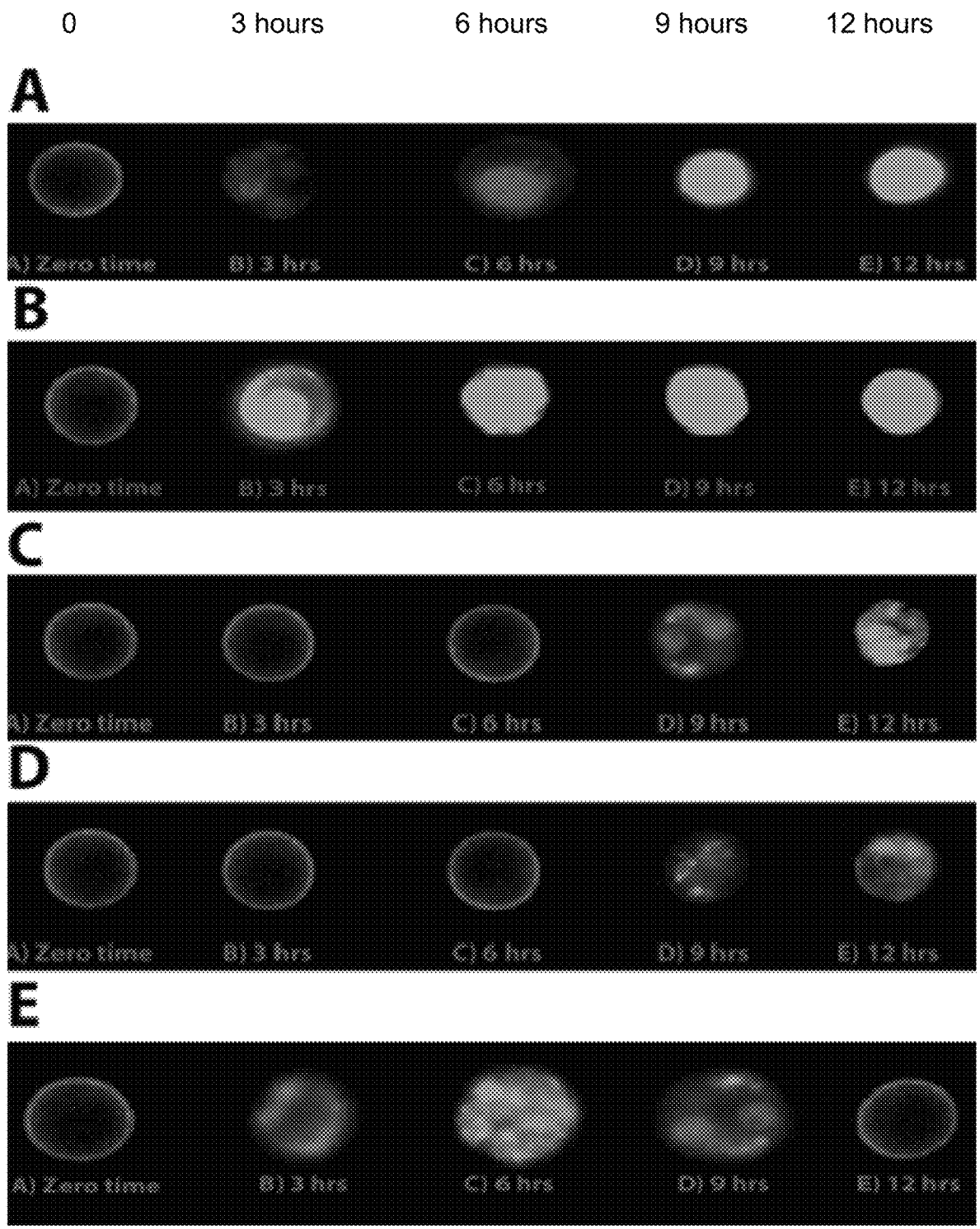
FIG. 6 shows fluorescence microscopy of yeast strain 2AS after induction with 5 mM galactose. Panel (A) shows control, with no compound. Panel (B) shows representative images for 1 micromolar amphetamine. Panel (C) shows representative images for the monomers caffeine, metformin, (R,S)-nicotine, and (R,S)-1-aminoindan at 1 micromolar and the bifunctional molecules $C_7$-6-$C_7$ (5), $C_7$-6-M (8) and $C_8$-6-M (4). Panel (D) shows $C_7$-6-I (7) at 1 micromolar. Panel (E) shows representative images for $C_8$-6-I (3) and $C_8$-6-N (2) at 1 micromolar.

Example 3.3—Characterization of Compounds in a Yeast Model for Parkinson's Disease—Visual Inspection of Protein Aggregation In order to visualize the aggregation status of the alpha-synuclein-GFP, the inventors examined the yeast cells using fluorescence microscopy. FIG. 6, panel A follows the aggregation of AS-GFP in the 2AS strain after induction with 5 mM galactose. Initially the fluorescence is localized to the periphery of the cell to give a halo effect as has been observed by others.[47,49] After 3 hours large foci appear as distinct features and the halo disappears. After 6 hours the individual foci have coalesced into a single entity, which without being bound by theory probably represents a single vacuolar inclusion.[53] At 9 hours, the entire cell appears to be filled with alpha-synuclein-GFP. Once the cells have reached this stage growth cannot be rescued by resuspending in galactose-free media (data not shown). The effect of adding 1 micromolar amphetamine is shown in FIG. 6, panel B. It is clear that larger foci appear at earlier times and complete filling of the cell occurs at 6 hours. At this stage the cells cannot be rescued by resuspending in galactose free-media. Similar results were found for the other neurotoxins, paraquat and rotenone (data not shown).

In contrast, the monomer compounds (FIG. 6, panel C) caffeine, metformin, (R,S)-nicotine, and (R,S)-1-aminoindan at 1 micromolar delayed the formation of foci until 9 hours after induction and the foci remain small compared to the control. The cells grow very slowly (FIG. 5A) and remain viable. The bifunctional molecules, including $C_7$-6-$C_7$ (5), $C_7$-6-M (8) and $C_8$-6-M (4) also give a similar pattern (FIG. 6, panel C) although some such as $C_7$-6-I (7), which allows moderate growth (FIG. 5B), show a more diffuse area of fluorescence especially at 12 h (FIG. 6, panel D).

Thus there appears to be a good correlation between the aggregation status of the alpha-synuclein-GFP in the presence of a compound and the ability of the compound to allow cell growth. Without being bound by theory, one possible way to explain these results is that initially the compounds prevent the aggregation of alpha-synuclein-GFP so that the proteasome and autophagic clearance mechanisms continue to function. Eventually, however, they become overwhelmed and the alpha-synuclein-GFP begins to accumulate, causing severe stress and a reduction in cell growth.

Finally, the behaviour of $C_8$-6-I (3) and $C_8$-6-N (2), which allow normal growth even at 0.1 micromolar (FIG. 5C) is very different from the other tested compounds (FIG. 6, panel E for $C_8$-6-I (3); the images for $C_8$-6-N (2) are similar). At 3 hours, the halo disappears and a diffuse pattern of fluorescence is observed which is distinct from the control at 3 hours (FIG. 6, panel A). At 6 hours, distinct foci can be seen which become more diffuse at 9 hours and by 12 hours the peripheral halo is restored.

This very complex behaviour suggests that several factors may be involved. Without being bound by theory, one possibility is that $C_8$-6-I (3) and $C_8$-6-N (2), which bind more weakly compared to many of the monomers and bifunctional molecules (see binding constants of Table 1) induce the formation of small perhaps soluble aggregates which then stimulate the protein clearance machinery, allowing normal growth. The nanopore results also suggest that these are the only ones of the tested bifunctional molecules that do not cause alpha-synuclein to adopt a compact conformation. Thus, without being bound by theory, the conformation of the drug/alpha-synuclein complex may be more important for rescuing yeast from alpha-synuclein-induced toxicity than the absolute binding constant, although it is predicted that bifunctional molecules that cause alpha-synuclein to adopt a loop-like configuration but have a higher binding affinity may perform better in vivo.

Figure 7:
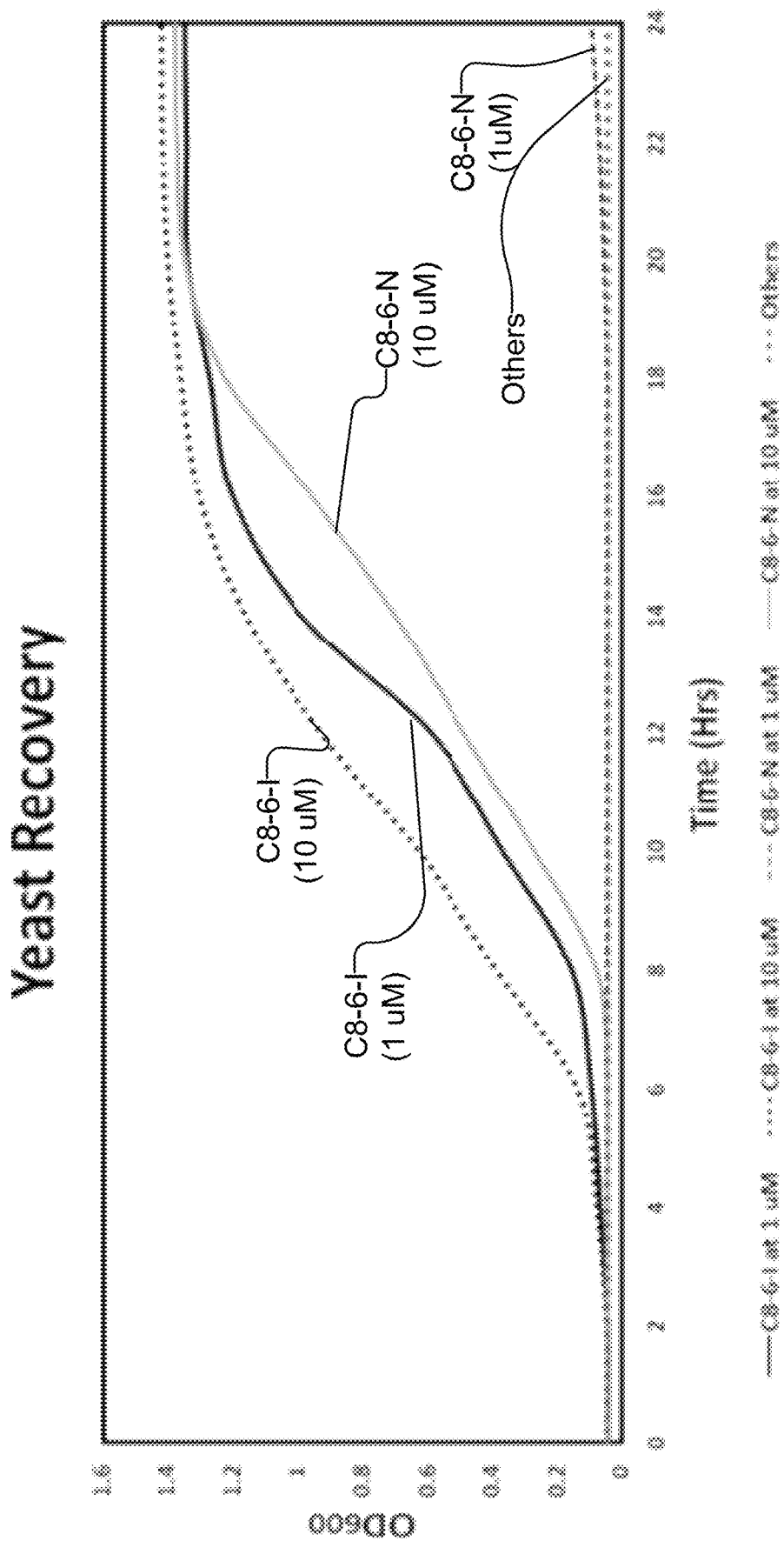
FIG. 7 shows the growth recovery of yeast 2AS strain. The cells were treated with 5 mM galactose for 6 hours, then washed and the indicated compounds were added at time 0 hours.
Figure 8:
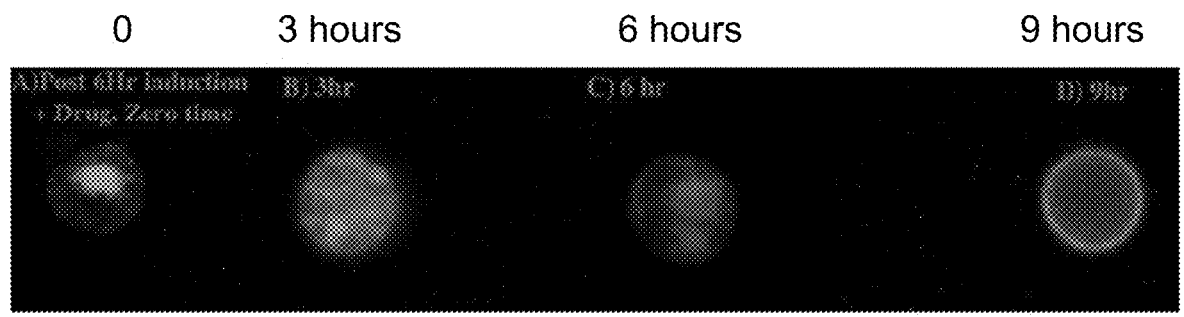
FIG. 8 shows fluorescence microscopy of yeast 2AS strain. The cells were treated with 5 mM galactose for 6 hours, then washed and 1 micromolar $C_8$-6-I (3) was added.
Figure 9A:
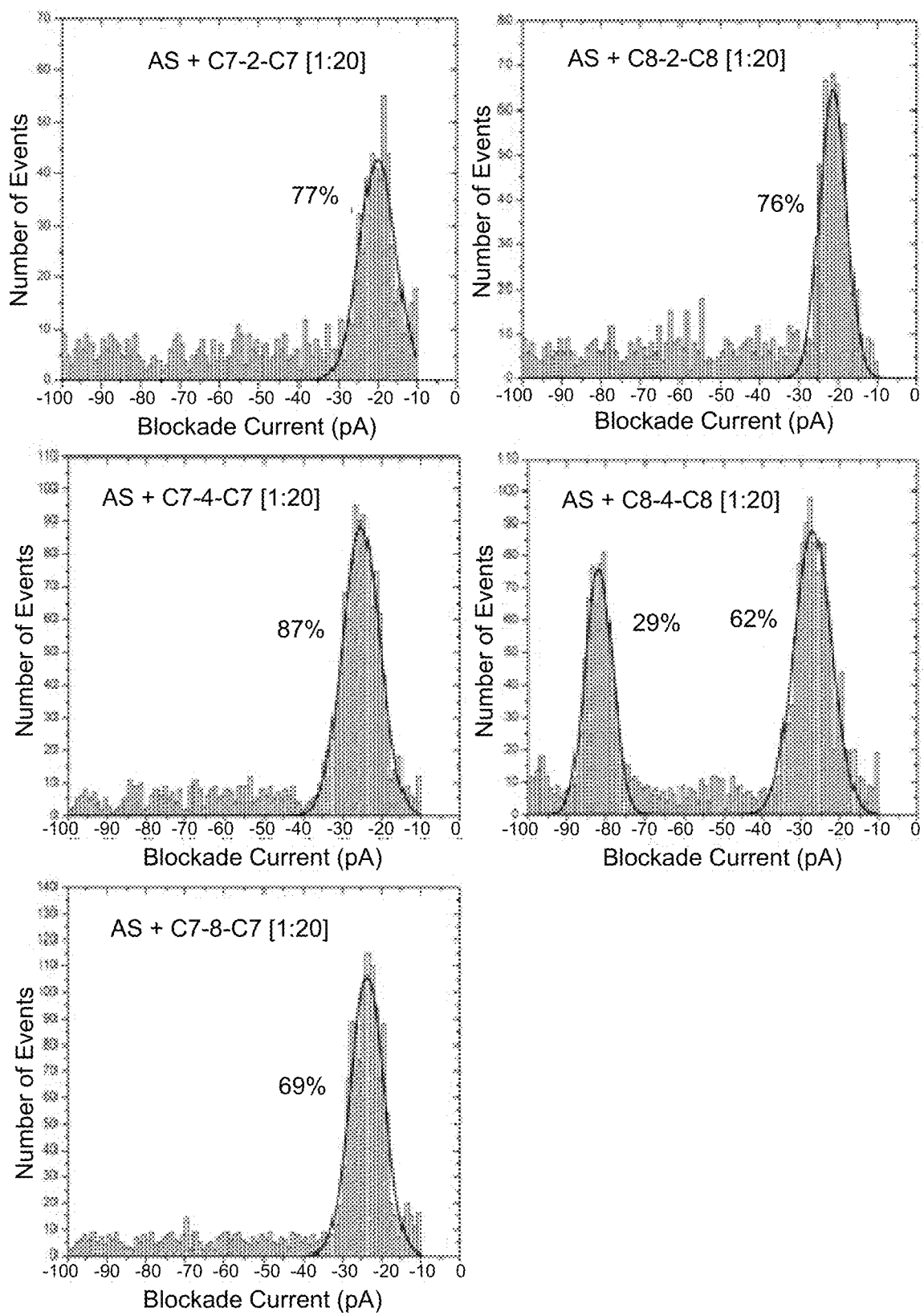
FIGS. 9A, 9B, 9C and 9D show nanopore analysis blockade current histograms of alpha-synuclein (AS) for the compounds identified in each panel.
Figure 9B:
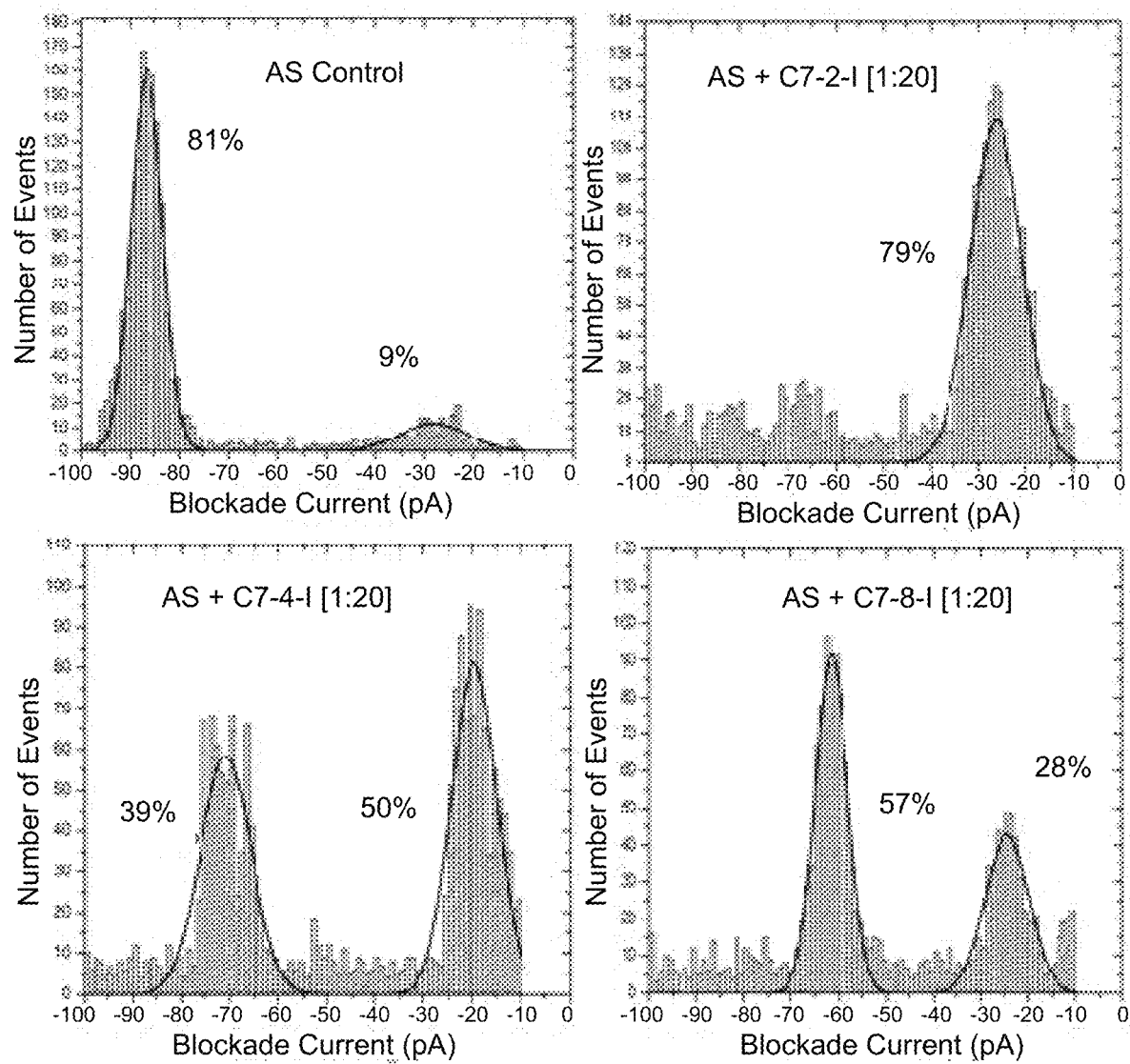
Figure 9C:
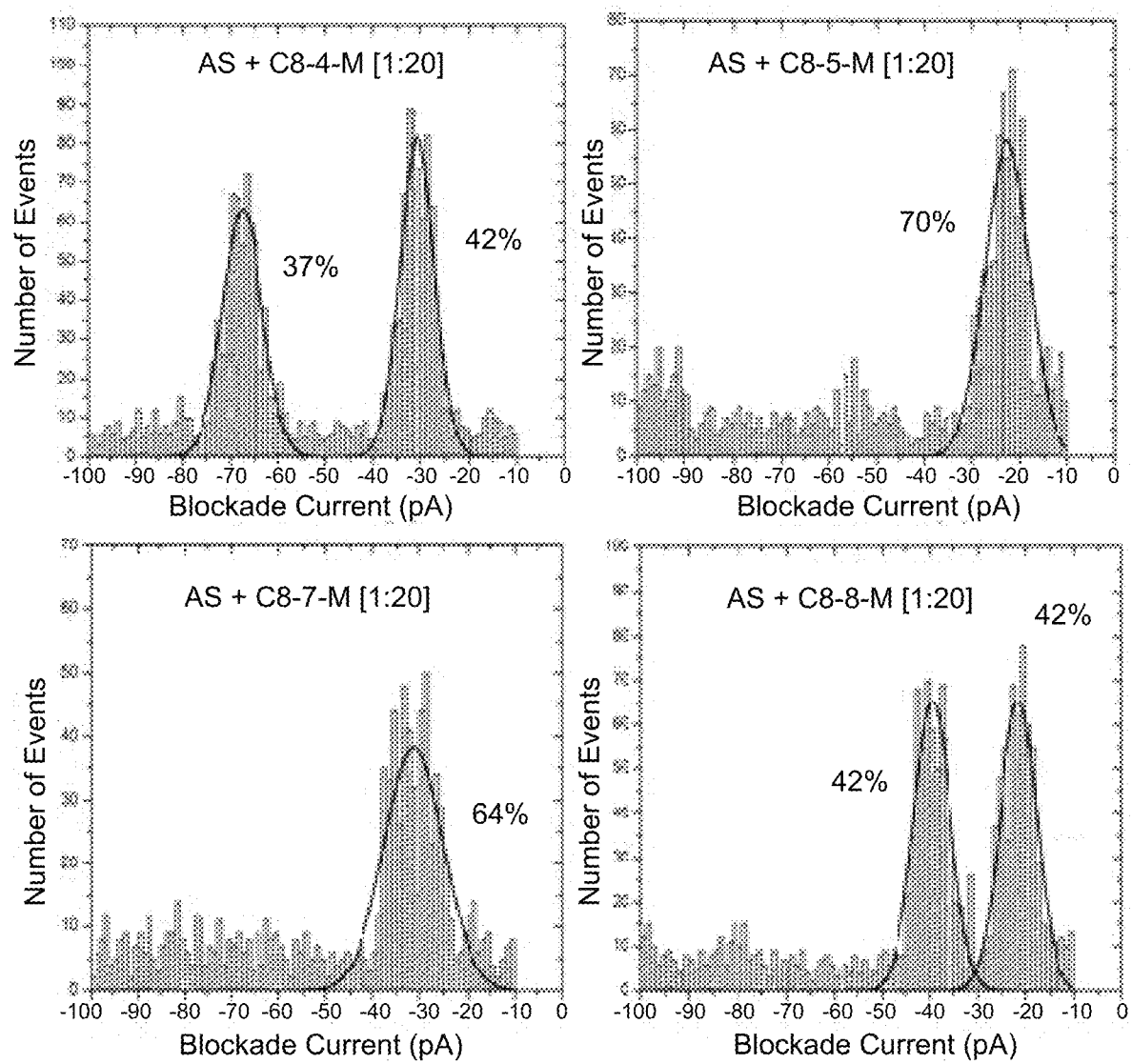
Figure 9D:
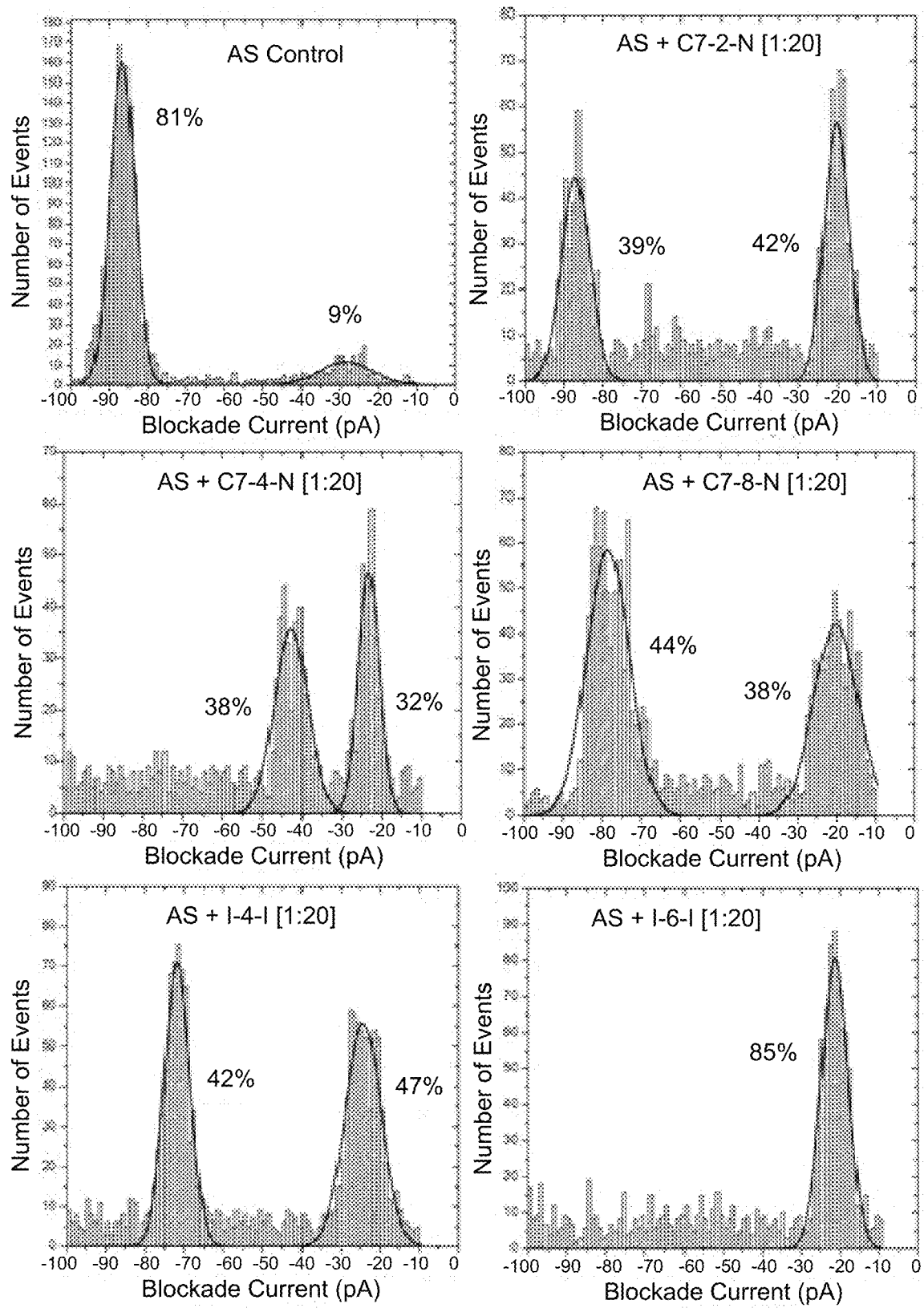

The ability of $C_8$-6-I (3) and $C_8$-6-N (2) to allow the recovery of the yeast cells even when the bifunctional molecules were added 6 hours after the induction of alpha-synuclein-GFP with 5 mM galactose was examined. As shown in FIG. 7, addition of $C_8$-6-I (3) at 10 micromolar or $C_8$-6-I (3) at 1 micromolar allows resumption of growth at about 6 hours or 8 hours respectively. For $C_8$-6-N (2) resumption of growth is only observed at 10 micromolar. The corresponding fluorescent images are shown in FIG. 8 for $C_8$-6-I (3) at 1 micromolar. After 3 hours, the single large foci is beginning to disperse and becomes more diffuse at 6 hours. By 9 hours, the peripheral location is restored and the halo reappears. These results support that $C_8$-6-I (3) and $C_8$-6-N (2) can cause preformed large foci of alpha-synuclein to dissipate and be cleared from the cell.

Example 4.0—Characterization of Additional Bifunctional Molecules

Example 4.1—Synthesis of Additional Bifunctional Molecules

Additional bifunctional molecules were synthesized for characterization using synthetic techniques generally similar to those set forth in Example 1.0. Generally, the synthetic method for each class of compounds is similar, and the length of the linker n is varied by using an appropriate starting material.

Scheme 9: General synthetic scheme for synthesis of $C_8$-n-$C_8$.
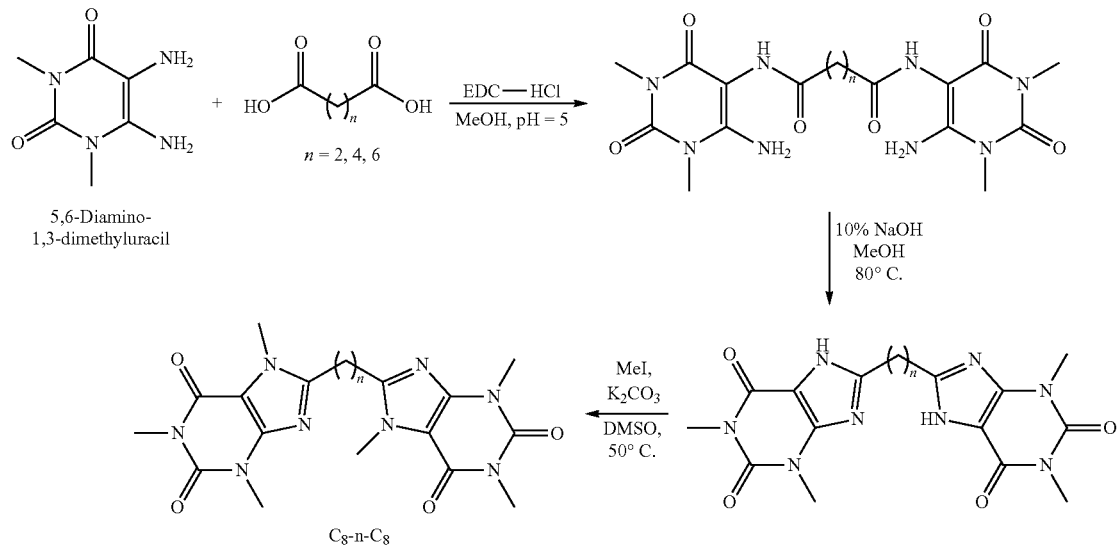
Scheme 10: General synthetic scheme of $C_8$-n-I.
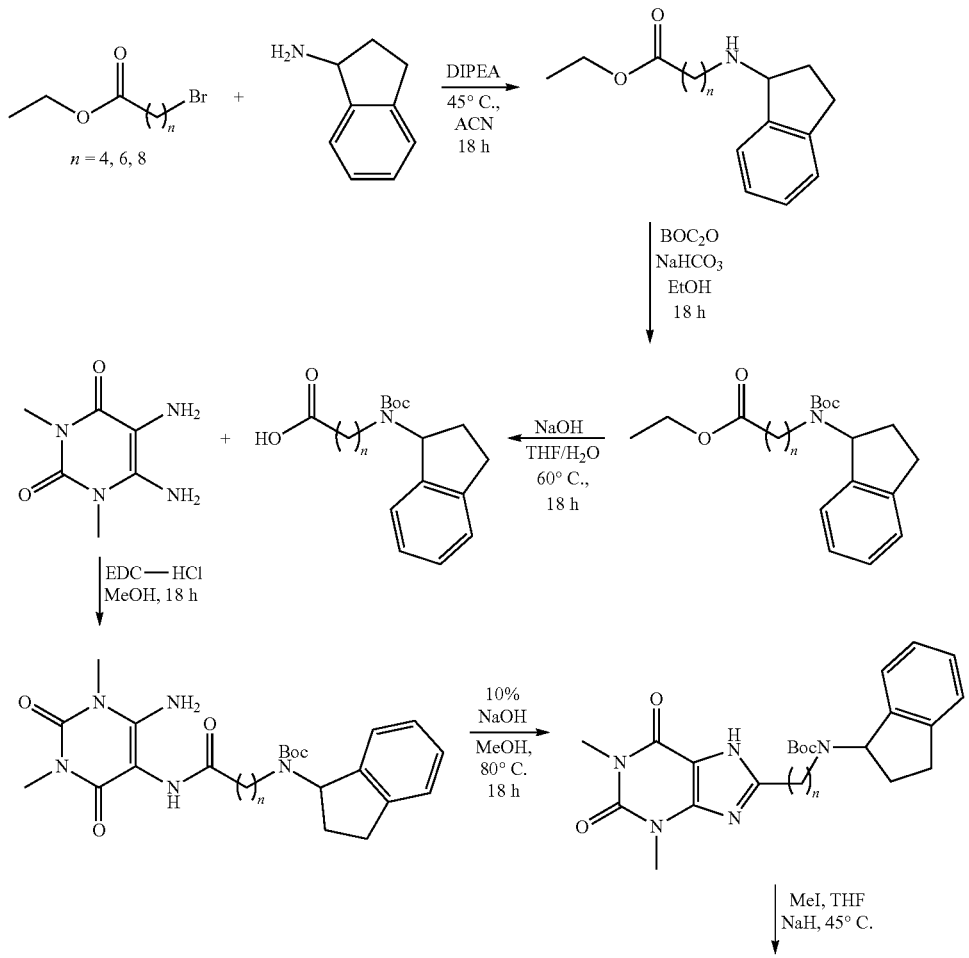

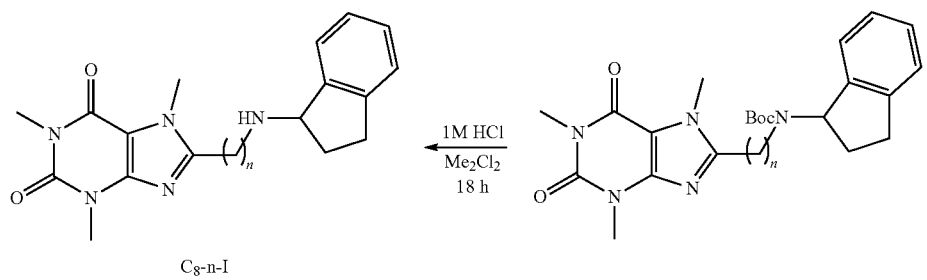
Scheme 11: General synthetic scheme of C$_7$-n-I, C$_7$-n-N and C$_7$-n-C$_7$.
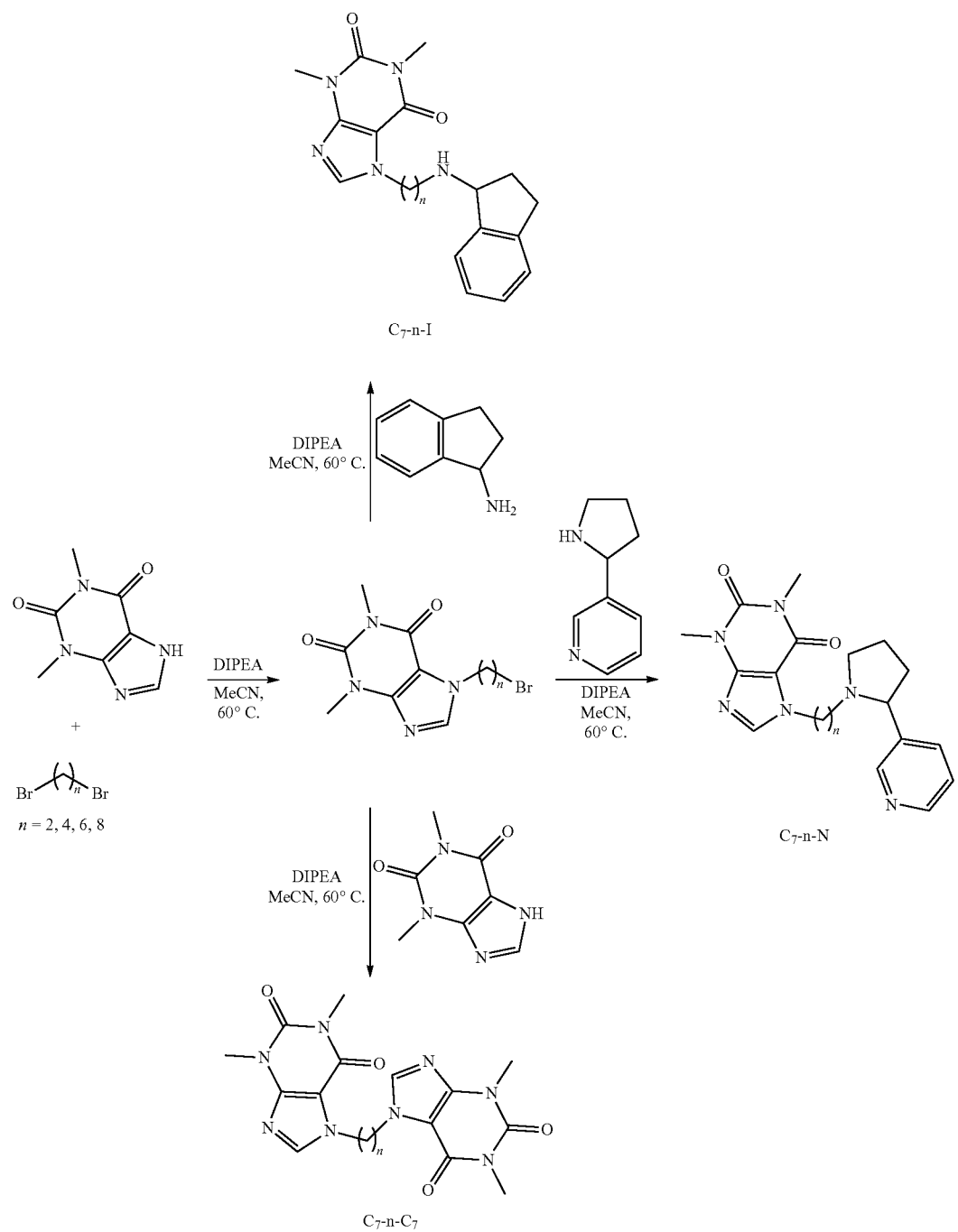

Scheme 12: General synthetic scheme of $C_8$-n-N.
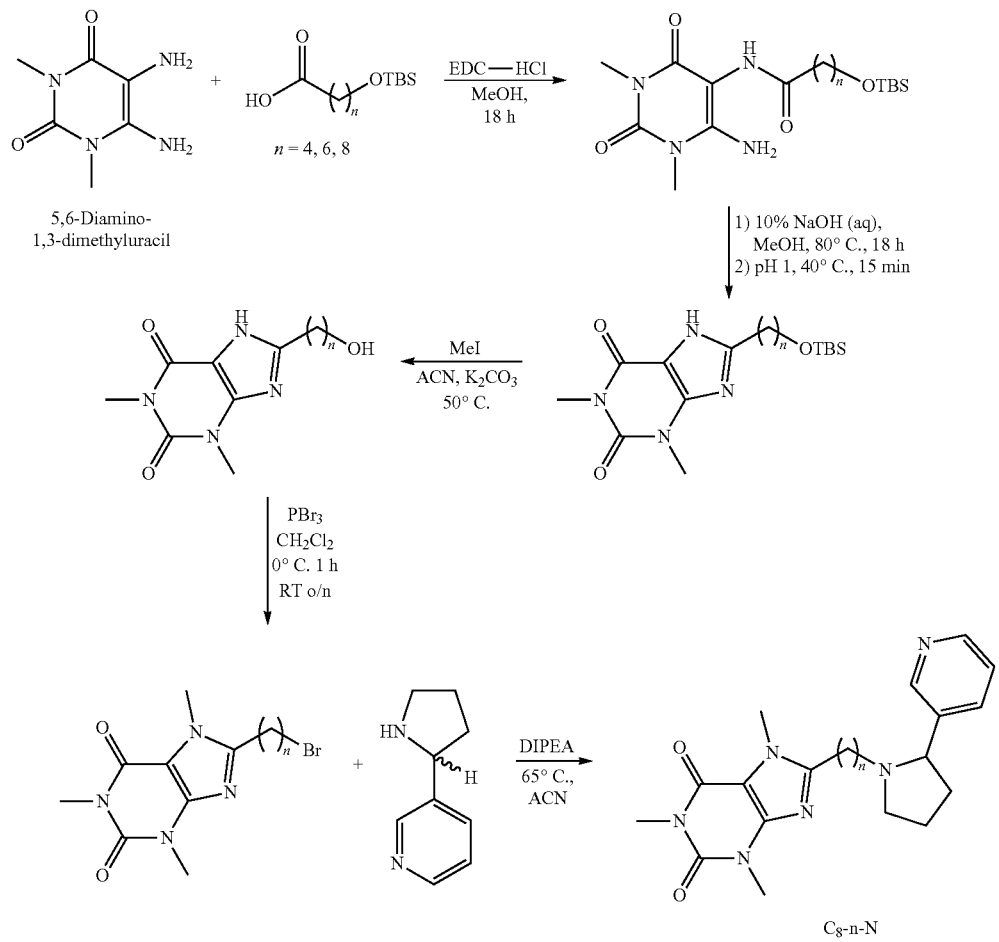
Scheme 13: General synthetic scheme of $C_8$-n-M.
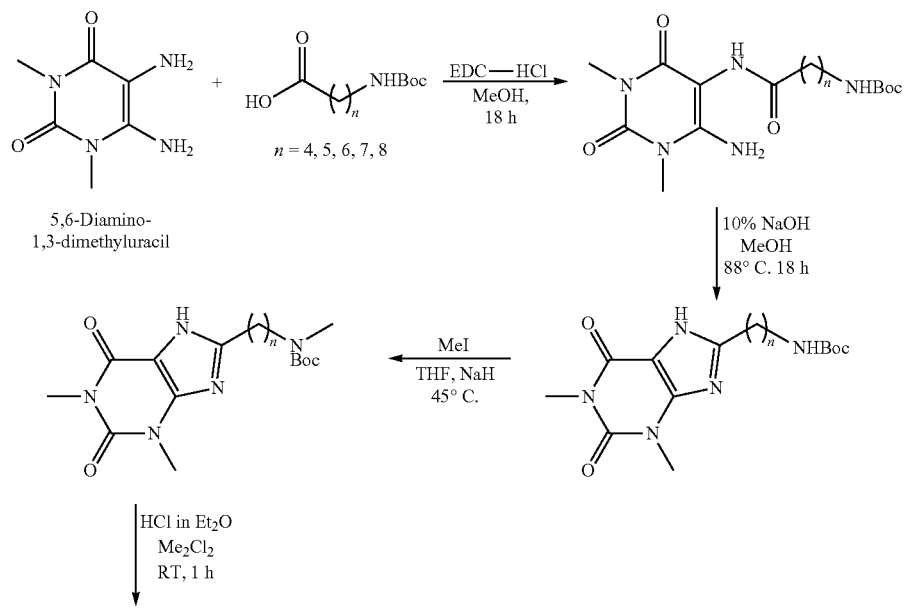

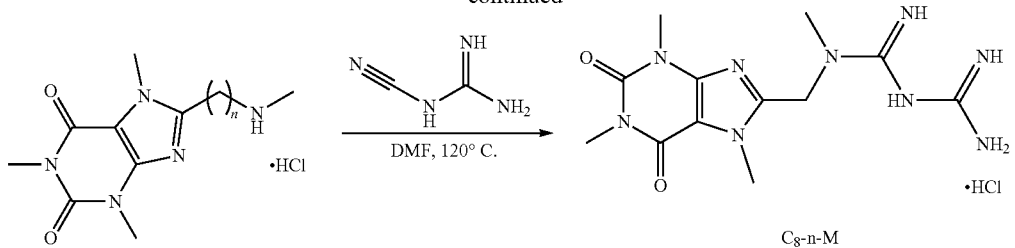

Scheme 14: General synthetic scheme of C₇-n-M.

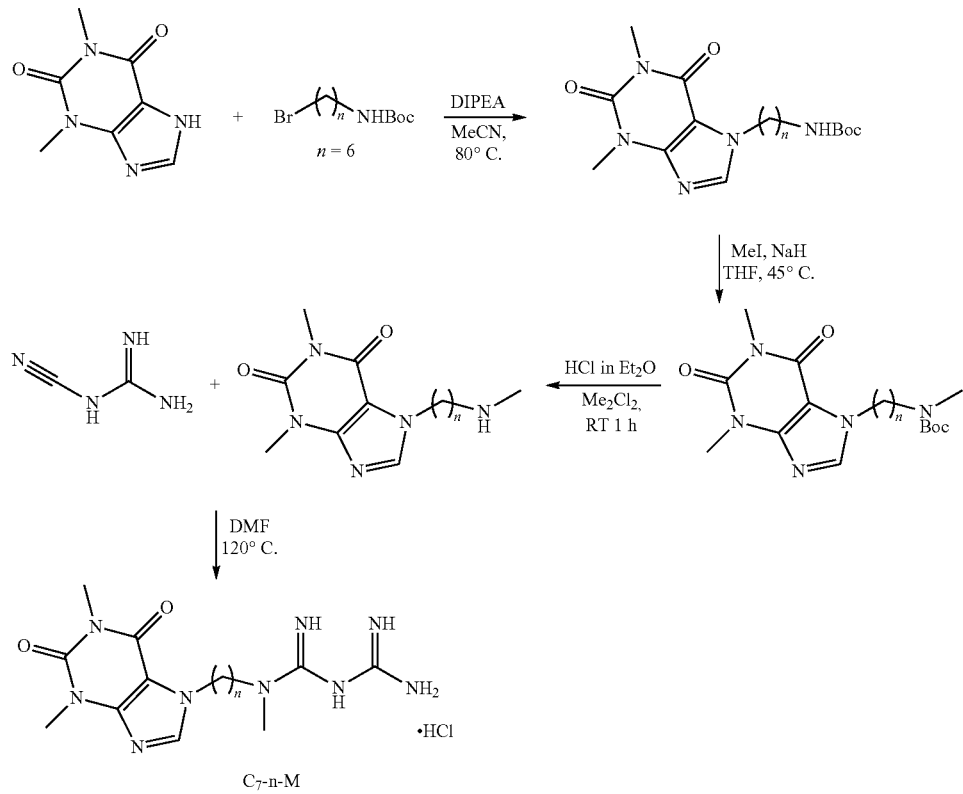

Scheme 15:
General synthetic scheme for I-4-1 (amide) (28) and I-6-I (amide) (29).

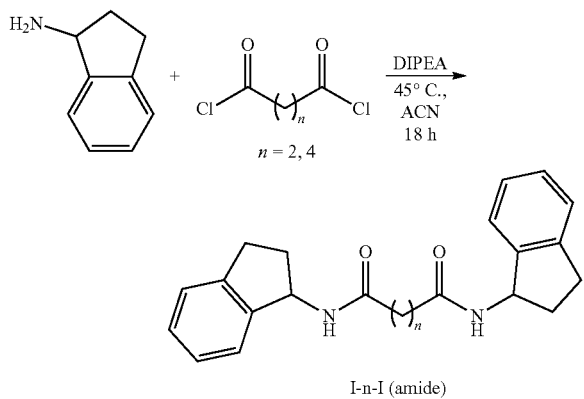

Example 4.2—Characterization of Binding to Alpha-Synuclein by Nanopore Analysis and ITC The additional synthesized bifunctional molecules were analyzed by nanopore analysis, and the results are shown in FIGS. 9A-9D. The test results show that all of the synthesized bifunctional molecules bind to alpha-synuclein. Additionally, the inventors have synthesized $C_8$-4-I (11), $C_8$-8-I (12) and $C_8$-8-N (23) and determined that all three compounds also bind to alpha-synuclein.

With respect to the data shown in FIGS. 9A-9D, $C_7$-2-$C_7$ (19), $C_8$-2-$C_8$ (9), $C_7$-4-$C_7$ (20), $C_7$-8-$C_7$ (21), $C_7$-2-I (13), $C_8$-5-M (25), $C_8$-7-M (26) and 1-6-I (29) all appear to cause alpha-synuclein to adopt a more compact configuration, as shown by the presence of significant bumping peaks. $C_8$-4-$C_8$ (10), $C_7$-4-I (14), $C_7$-8-I (15), $C_8$-4-M (24), $C_8$-8-M (27), $C_7$-2-N (16), $C_7$-4-N (17), $C_7$-8-N (18), and 1-4-I (28) also show bumping peaks, but have a shifted translocation peak visible as well.

The binding constants (Ka) of the various bifunctional molecules for interaction with alpha-synuclein were measured by ITC, and the results are presented in Table 2, together with results for select monomers, as well as the eight six-carbon linker bifunctional molecules characterized in Example 3.0. Table 2 also includes data confirming whether the compounds bind to both the N and C portions of alpha-synuclein (Bind to N and C, Y indicates yes, N indicates no), the number of binding sites for the compound on alpha-synuclein, and the results of the compound's ability to reduce aggregation of alpha-synuclein in a yeast model of Parkinson's Disease as evaluated by fluorescence microscopy, as discussed in Example 4.4 below. Based on the Ka values determined for the C-M series of compounds, the inventors predict that $C_8$-3-M and $C_8$-2-M may have a high binding affinity for alpha-synuclein.

TABLE 2

Binding constants for all tested compounds, mode of binding, number of binding sites.

| Compound | Number | Ka (M$^{-1}$) | Molecular Weight | Bind to N and C? | # Binding sites | Stage at 12 hrs |
|---|---|---|---|---|---|---|
| $C_8$6N | (2) | $4.3 \times 10^4$ | | Y | 1 | E |
| $C_7$8N | (18) | $4 \times 10^6$ | 438.06 | Y | 1 | C |
| $C_7$6N | (6) | $5 \times 10^6$ | 410.24 | Y | 1 | C |
| $C_7$4N | (17) | $3 \times 10^6$ | 382.46 | Y | 1 | C |
| $C_7$2N | (16) | $5 \times 10^4$ | 354.18 | Y | 1 | C |
| $C_8$6I | (3) | $5.3 \times 10^4$ | | Y | 1 | E |
| $C_7$8I | (15) | $2 \times 10^7$ | 423.24 | Y | 0.5 | D |
| $C_7$6I | (7) | $2 \times 10^6$ | 395.23 | Y | 1 | D |
| $C_7$4I | (14) | $5 \times 10^6$ | 367.20 | Y | 1 | D |
| $C_7$2I | (13) | $9 \times 10^4$ | 339.39 | Y | 1 | C |
| $C_7$8$C_7$ | (21) | $4 \times 10^5$ | 470.24 | Y | 0.5 | B |
| $C_7$6$C_7$ | (5) | $7 \times 10^5$ | 432.95 | Y | 2 | C |
| $C_7$4$C_7$ | (20) | $1 \times 10^7$ | 414.18 | Y | 0.5 | A |
| $C_8$7M | (26) | $6.4 \times 10^5$ | | Y | 2 | B |
| $C_8$-2-$C_8$ | (9) | $9 \times 10^5$ | | Y | 1 | B |
| $C_8$-4-$C_8$ | (10) | $4 \times 10^7$ | 428.21 | Y | 0.25 | C/D |
| $C_8$-6-$C_8$ | (1) | $2 \times 10^8$ | | Y | 0.25 | B |
| $C_7$-2-$C_7$ | (19) | $3 \times 10^4$ | 388.21 | Y | 1 | B |
| $C_8$-4-M | (24) | $4 \times 10^7$ | | Y | 0.5 | D |
| $C_8$-5-M | (25) | $2.01 \times 10^5$ | | Y | 1 | A/C |
| $C_7$-6-M | (8) | $2.5 \times 10^4$ | | Y | 0.5 | C |
| $C_8$-8-M | (27) | $4.3 \times 10^4$ | | Y | 1 | A/C |
| $C_8$-6-M | (4) | $5.7 \times 10^5$ | | Y | 0.5 | C/D |
| I-diamide-6-I | (29) | $5 \times 10^5$ | 390.18 | Y | 0.5 | A/B |
| I-diamide-4-I | (28) | $3 \times 10^7$ | 362.47 | Y | 0.5 | A/B |
| Caffeine | (102) | $7 \times 10^5$ | 194.19 | Y | 1 | C |
| Indan-amide-methyl | | $4 \times 10^5$ | 178.20 | Y | 0.5 | N/A |
| Nicotine | (104) | $1 \times 10^6$ | 162.23 | Y | 1 | C |
| S-Indan | | $3 \times 10^6$ | 133.19 | Y | 1 | C |
| R-Indan | | $1 \times 10^6$ | 133.19 | Y | 1 | C |
| Metformin | (107) | $9 \times 10^6$ | | N | 3 | C |
| 4-Fluoro-indan-1-yl-amine | (114) | $3.0 \times 10^6$ | | Y | 0.5 | N/A |

Figure 10A:
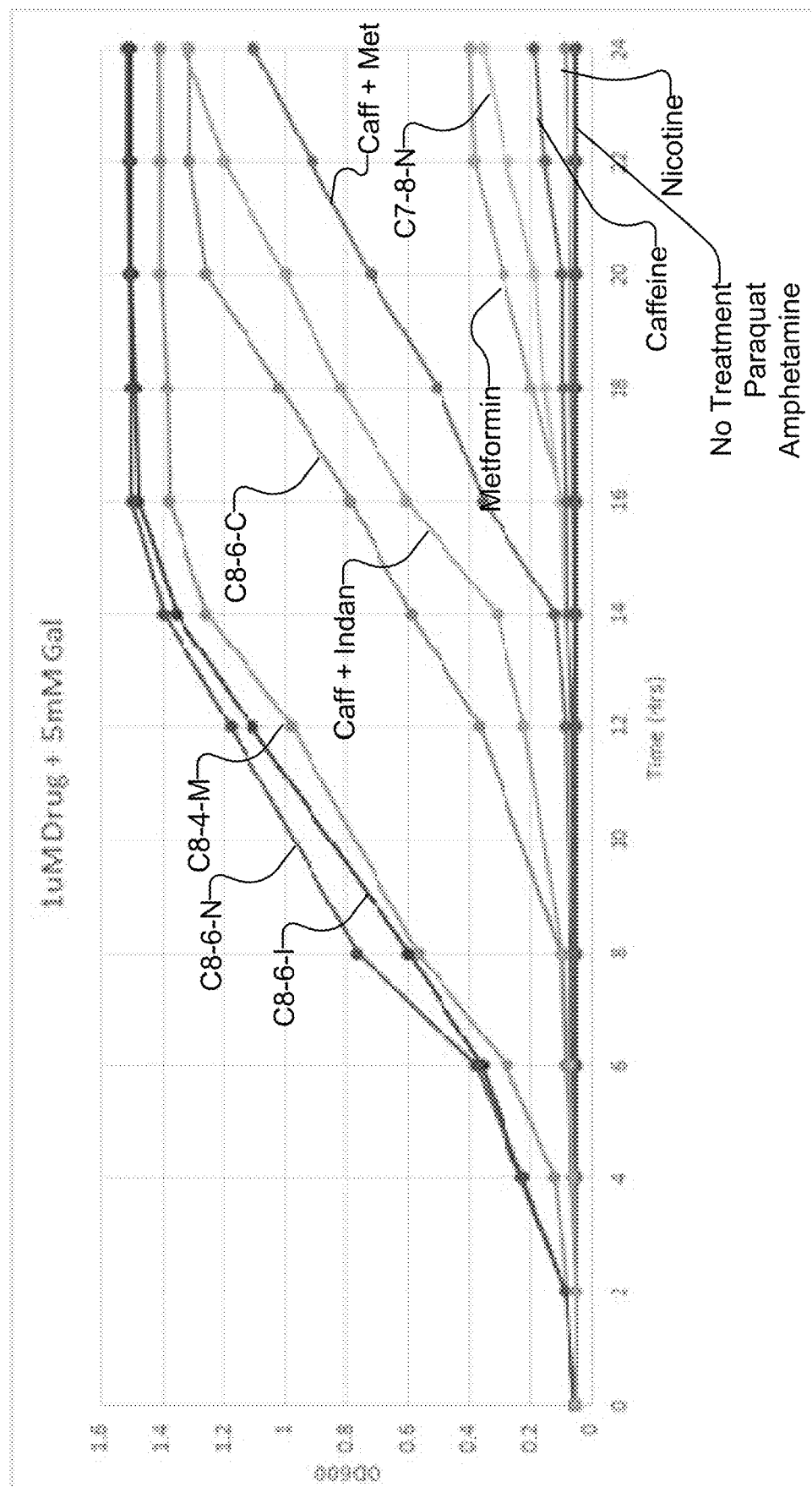
FIGS. 10A and 10B show growth of yeast strain 2AS monitored at $OD_{600}$ over 24 hours with 5 mM galactose and 1 micromolar of the indicated compounds.
Figure 10B:
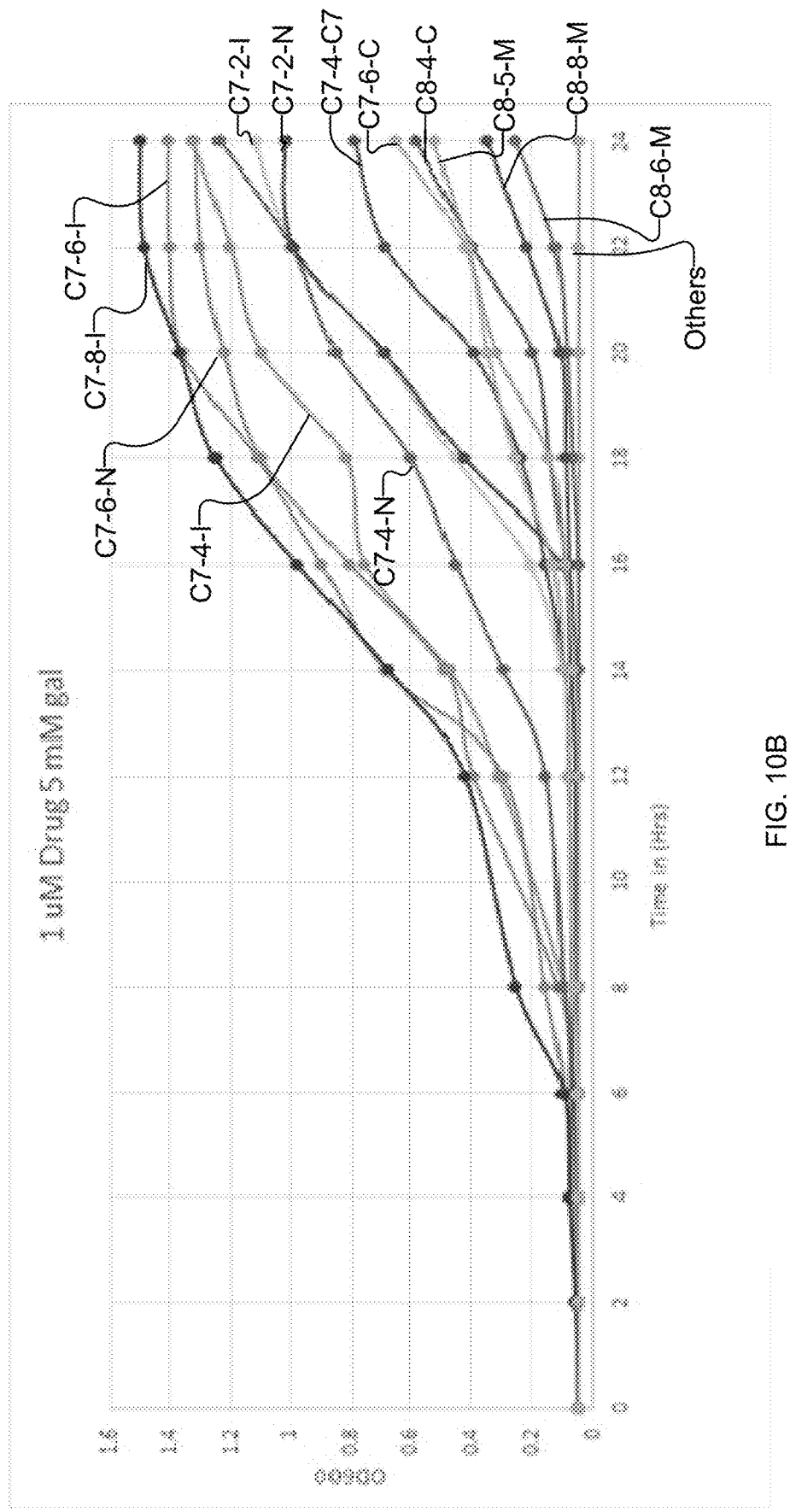

Example 4.3—Characterization of Compounds in a Yeast Model for Parkinson's Disease—Growth FIGS. 10A and 10B show the growth of yeast strain 2AS in the presence of 5 mM galactose and 1 micromolar of the indicated compound, either monomer, combination of monomers, or bifunctional molecule. $C_8$-4-M (24) was able to rescue yeast growth to a reasonable extent at 1 micromolar concentration, nearly as well as $C_8$-6-I (3) and $C_8$-6-N (2). However, tests of $C_8$-4-M (24) at 0.1 micromolar showed that it did not rescue yeast growth at that lower concentration, while $C_8$-6-I (3) and $C_8$-6-N (2) did.

Example 4.4—Characterization of Compounds in a Yeast Model for Parkinson's Disease—Visual Inspection of Protein Aggregation The additional compounds were evaluated using fluorescence microscopy to monitor the aggregation of AS-GFP in yeast strain 2AS as in Example 3.3. The results of this characterization are presented in Table 2, in which the general trend of the status of protein aggregation after 12 hours is indexed as A, B, C, D or E to indicate that the visual evaluation of protein aggregation after 12 hours was most similar to the images shown in panels A, B, C, D or E of FIG. 6.

Example 5.0—In Vivo Studies in Rats with Elevated Levels of Alpha-Synuclein

Results of the first round of studies evaluating the effects of increased alpha-synuclein expression in vivo in a rat model are shown in FIGS. 11 and 12A-12E. Test groups of rats were also administered the neuroprotective monomer 1-aminoindan which binds to alpha synuclein and inhibits its aggregation, or 2-aminoindan, which binds to alpha-synuclein but does not prevent its aggregation and is predicted to be neurotoxic.

Figure 11:
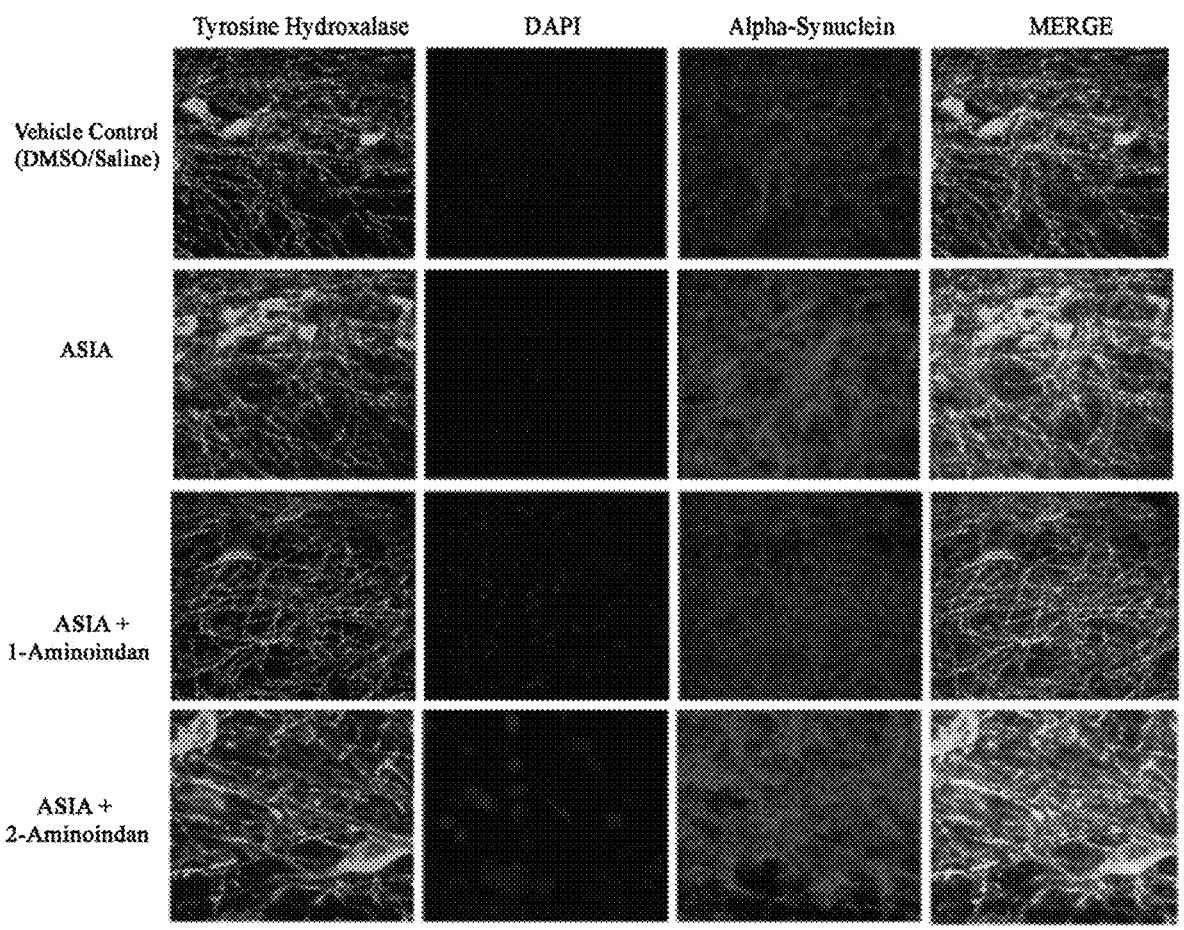
FIG. 11 shows the results of immunohistochemistry carried out on the substantia nigra of a first group of rats treated with an alpha-synuclein inducing agent (ASIA).

As can be seen in FIG. 11, immunohistochemistry of the substantia nigra after seven days of chronic injections was carried out. Tyrosine hydroxylase expression (first column) shows the location of dopaminergic neurons, while DAPI staining (second column) indicates the location of cell nuclei. The level of alpha-synuclein observable in both the groups treated with alpha-synuclein inducing agent (ASIA) and ASIA+2-aminoindan (which is predicted to be neurotoxic) is considerably increased over both control rats (injected with DMSO and saline) and rats administered ASIA together with 1-aminoindan, which is predicted to be neuroprotective.

Figure 12A:
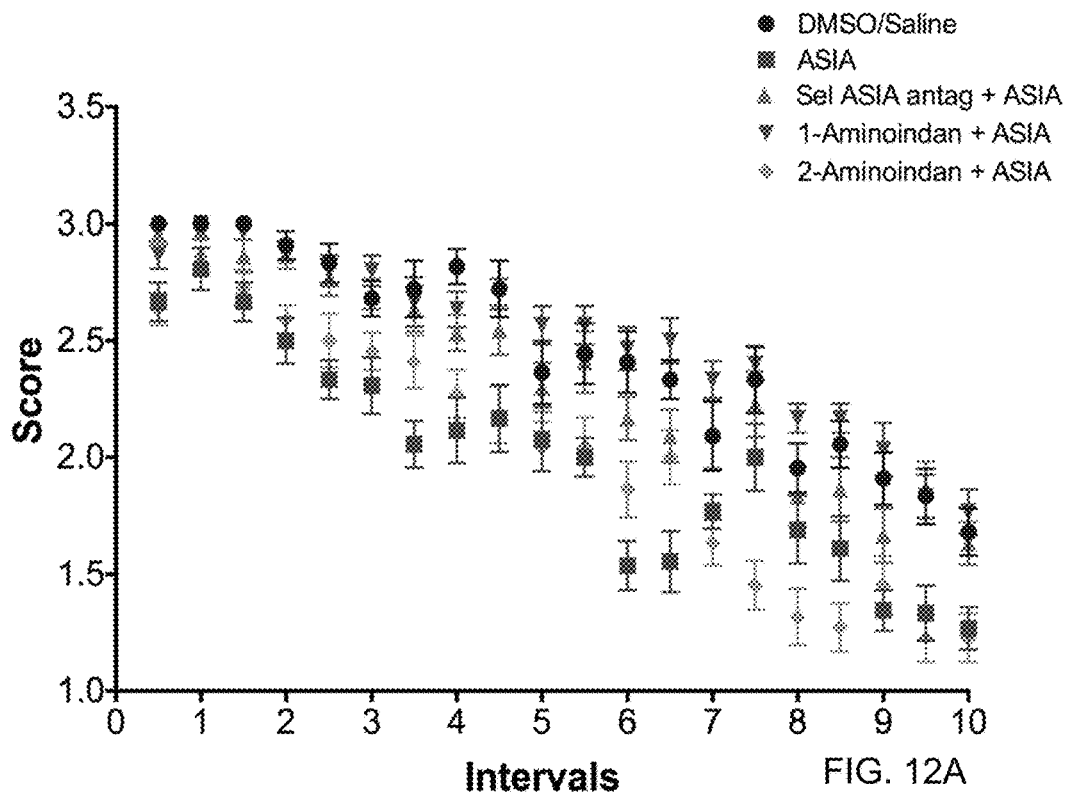
FIGS. 12A, 12B, 12C, 12D and 12E show the results of a forced swim test for the first group of rats.
Figure 12B:
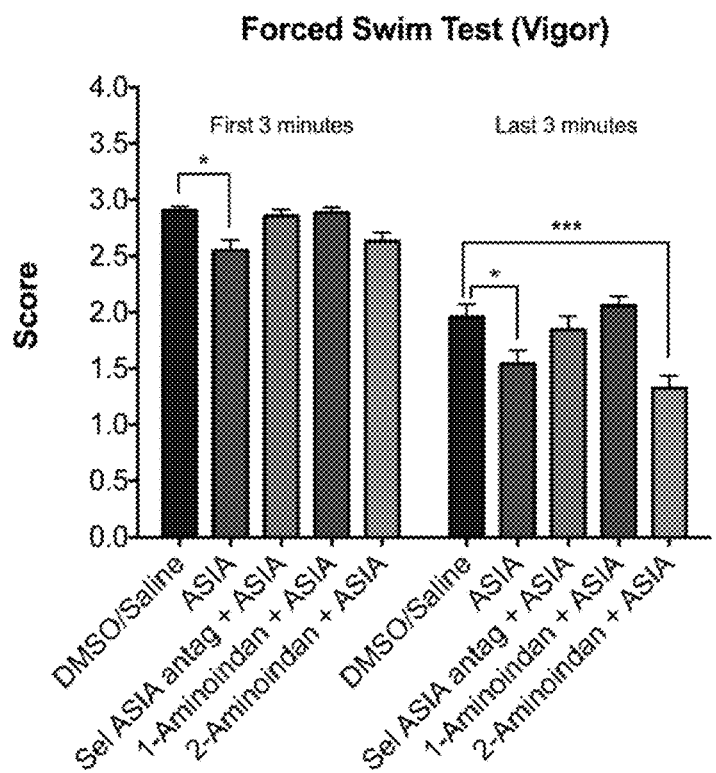

With reference to FIGS. 12A and 12B, assessing the vigor of the treated rats in a forced swim test, in the last three minutes of the test, the rats in the ASIA treated group and the group treated with ASIA+2-aminoindan (predicted to be neurotoxic) show decreased vigor compared to the control animals. Animals treated with ASIA in conjunction with either 1-aminoindan (neuroprotective) or a selective ASIA antagonist show some improvement, with vigor more similar to control animals injected with DMSO and saline, showing that the neuroprotective alpha-synuclein binding compound 1-aminoindan can protect against the effects of alpha-synuclein overexpression.

Figure 12C:
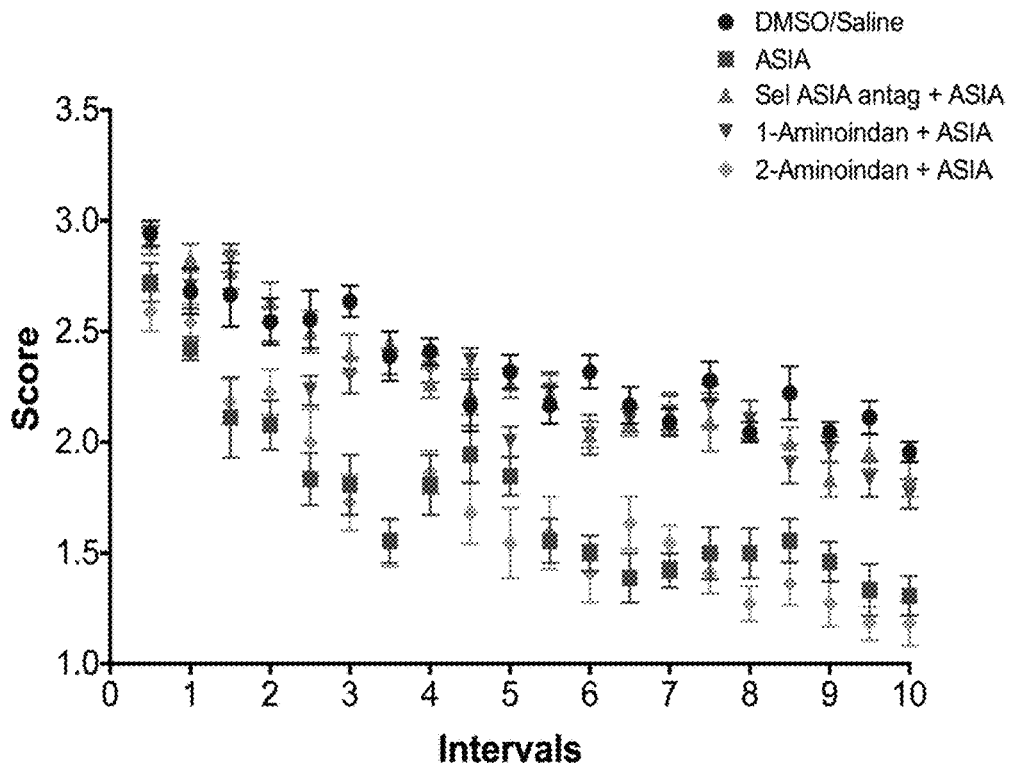
Figure 12D:
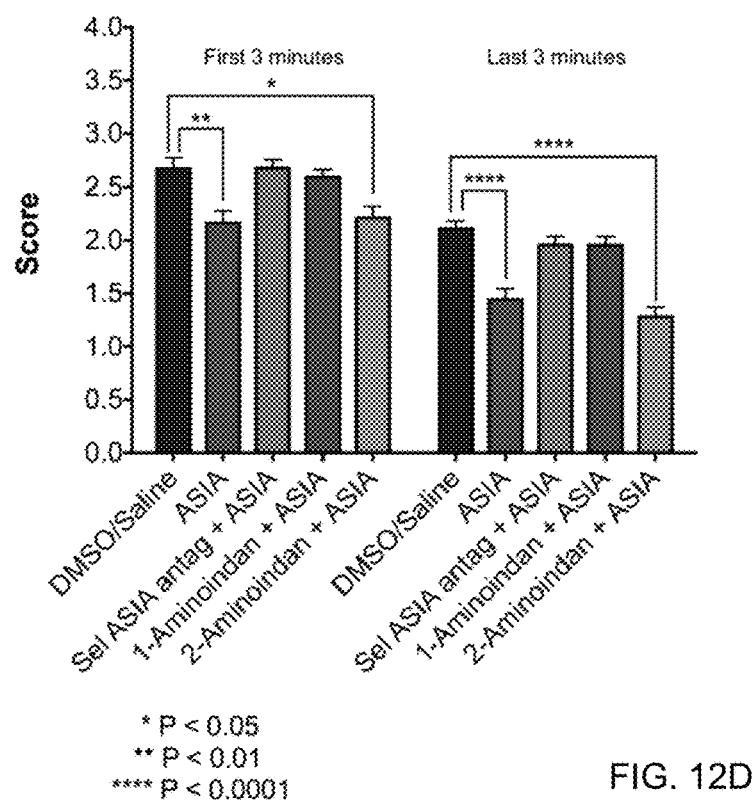

With reference to FIGS. 12C and 12D, assessing the success of the treated rats in a forced swim test, results are similar but effects observed are even more significant. In the last three minutes of the test, the rats in the ASIA treated group and the group treated with ASIA+2-aminoindan (predicted to be neurotoxic) show decreased success compared to the control animals. Animals treated with ASIA in conjunction with either 1-aminoindan (neuroprotective) or a selective ASIA antagonist show some improvement, with vigor more similar to control animals injected with DMSO and saline.

Figure 12E:
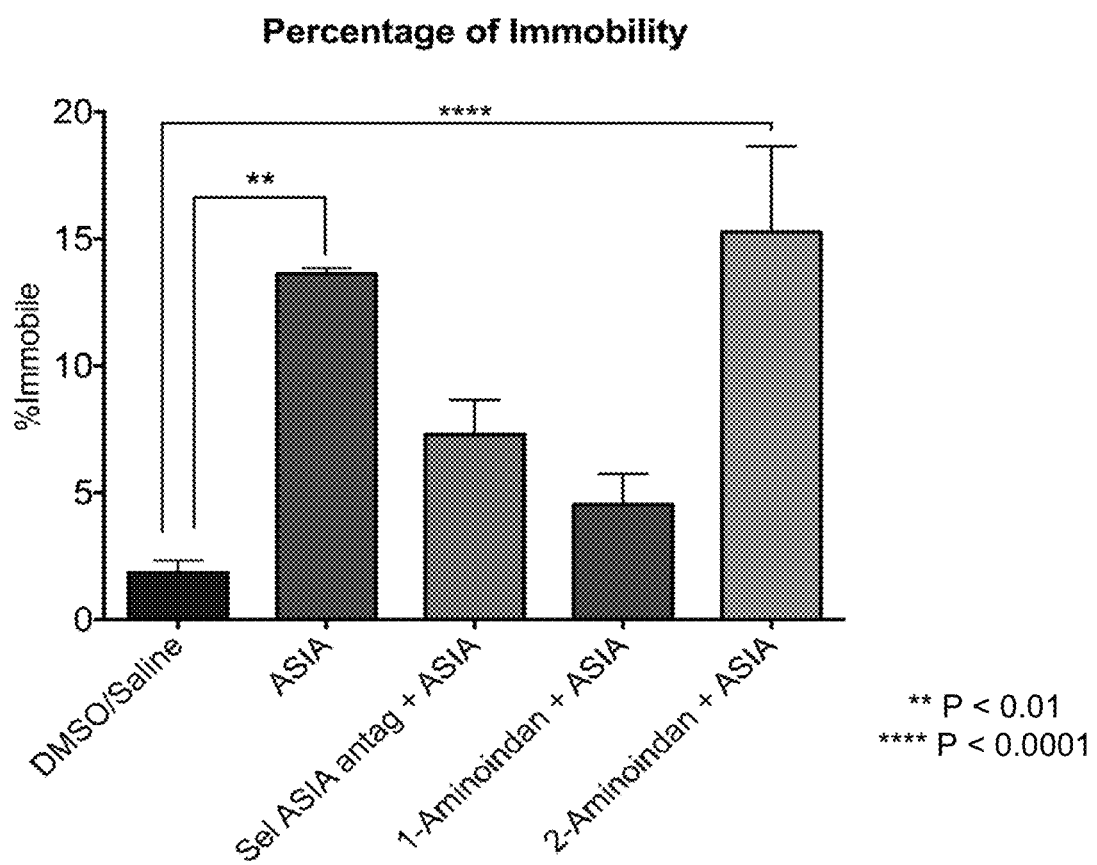

With reference to FIG. 12E, based on videos of the forced swim test, the amount of time that each rat was motionless was calculated as a form of scoring depression for each treatment. The results demonstrate that chronic administration of an alpha-synuclein inducing agent (ASIA), with or without 2-aminoindan (predicted to be neurotoxic) significantly increases immobility. These effects are partially reversed by co-administration of either a selective antagonist of the alpha-synuclein inducing agent (ASIA) or the neuroprotective alpha-synuclein binding agent 1-aminoindan.

Figure 13A:
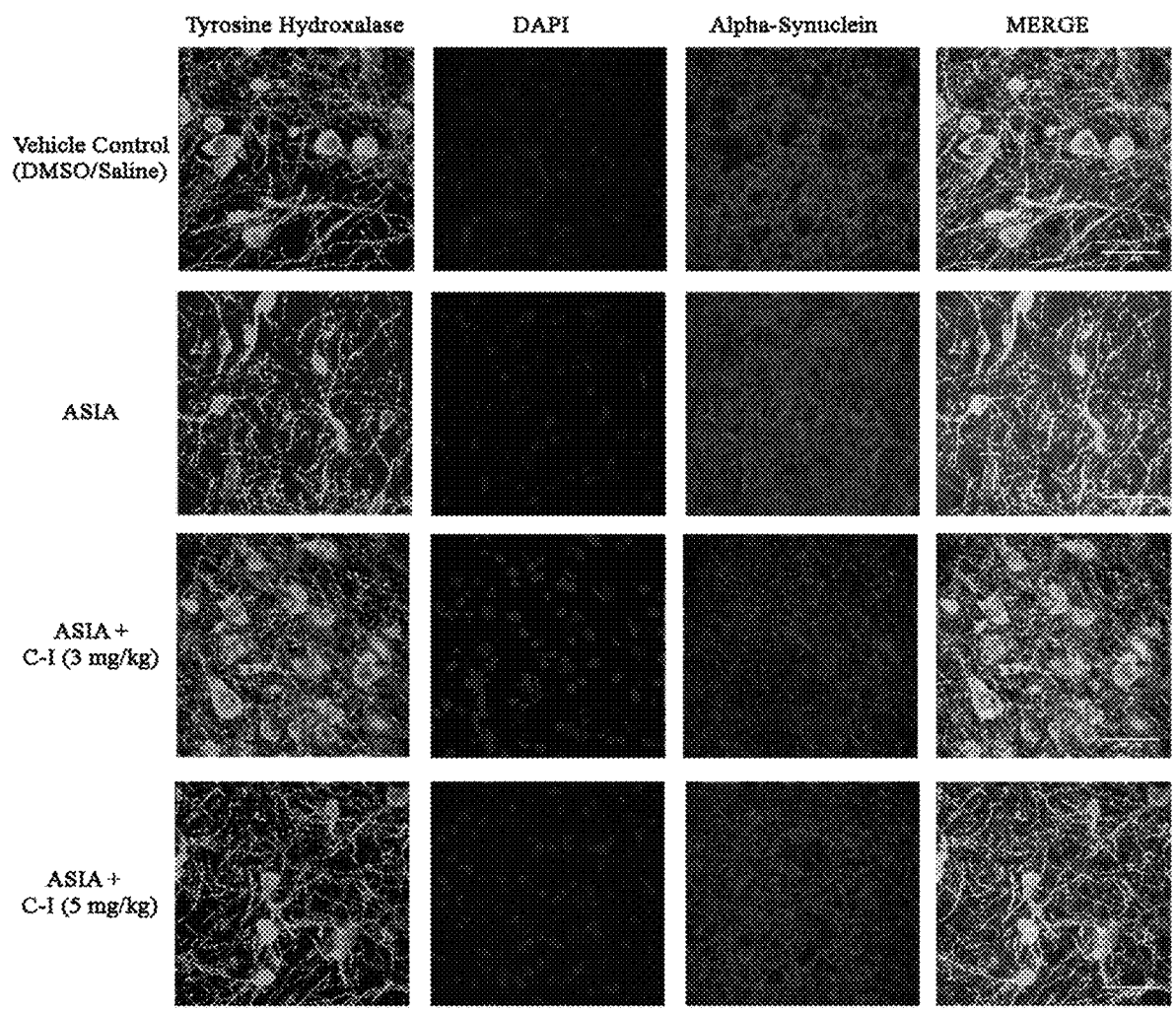
FIG. 13A shows the results of immunohistochemistry carried out on the substantia nigra of a second group of rats treated with an alpha-synuclein inducing agent (ASIA), some of which were treated with the bifunctional molecule $C_8$-6-I (3). Scale bar=50 μm.

A second round of studies in rats was conducted to evaluate the in vivo efficacy of the bifunctional molecule $C_8$-6-I (3) at two different dosages, 3 mg/kg and 5 mg/kg in rats overexpressing alpha-synuclein. With reference to FIG. 13A, immunohistochemistry of the substantia nigra after 7 days of chronic injections shows increased alpha-synuclein staining in animals administered the alpha-synuclein inducing agent (ASIA) (third column, second row). The level of alpha-synuclein observed is reduced in animals receiving $C_8$-6-I (3) at a dose of either 3 mg/kg or 5 mg/kg (third column, penultimate and bottom rows). Thus, the level of alpha-synuclein staining is reduced at both tested doses by the administration of $C_8$-6-I (3).

Figure 13B:
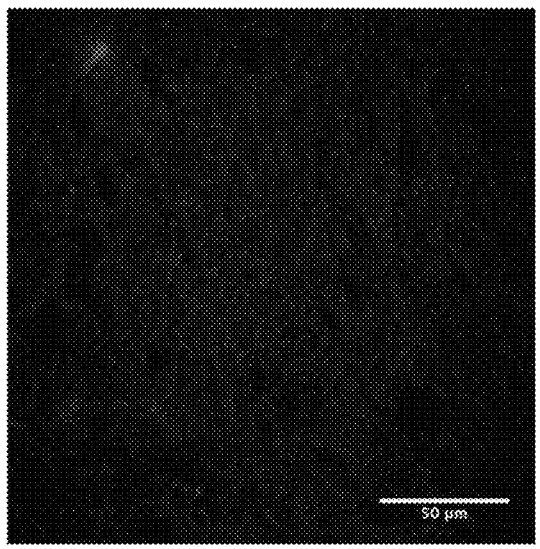
FIG. 13B shows the results of Thioflavin S staining in the substantia nigra for the second group of rats.
Figure 13B:
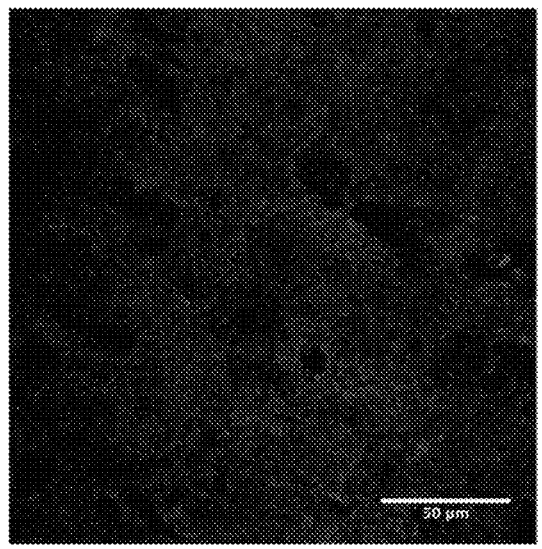
Figure 13B:
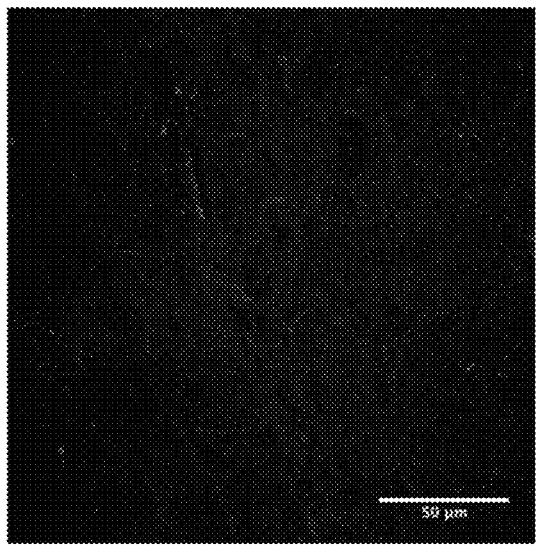
Figure 13B:
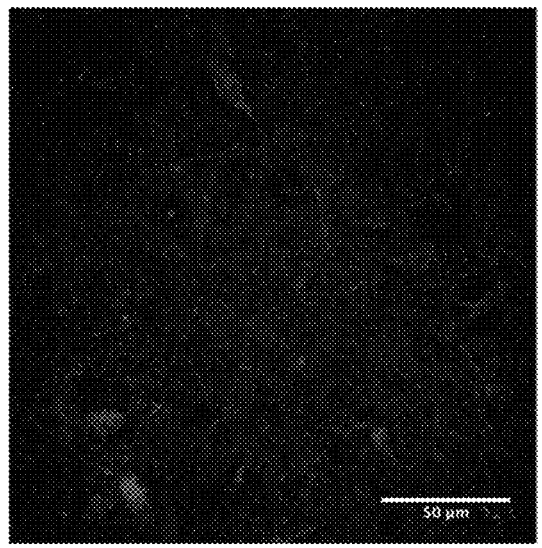

As can be seen from FIG. 13B, staining with thioflavin S to evaluate the degree of protein aggregation observed, administration of ASIA produces an increased level of staining as compared with the control (upper right versus upper left panels). Administration of $C_8$-6-I (3) decreases the degree of protein aggregation at both doses tested, i.e. 3 mg/kg and 5 mg/kg (lower panels).

Figure 14A:
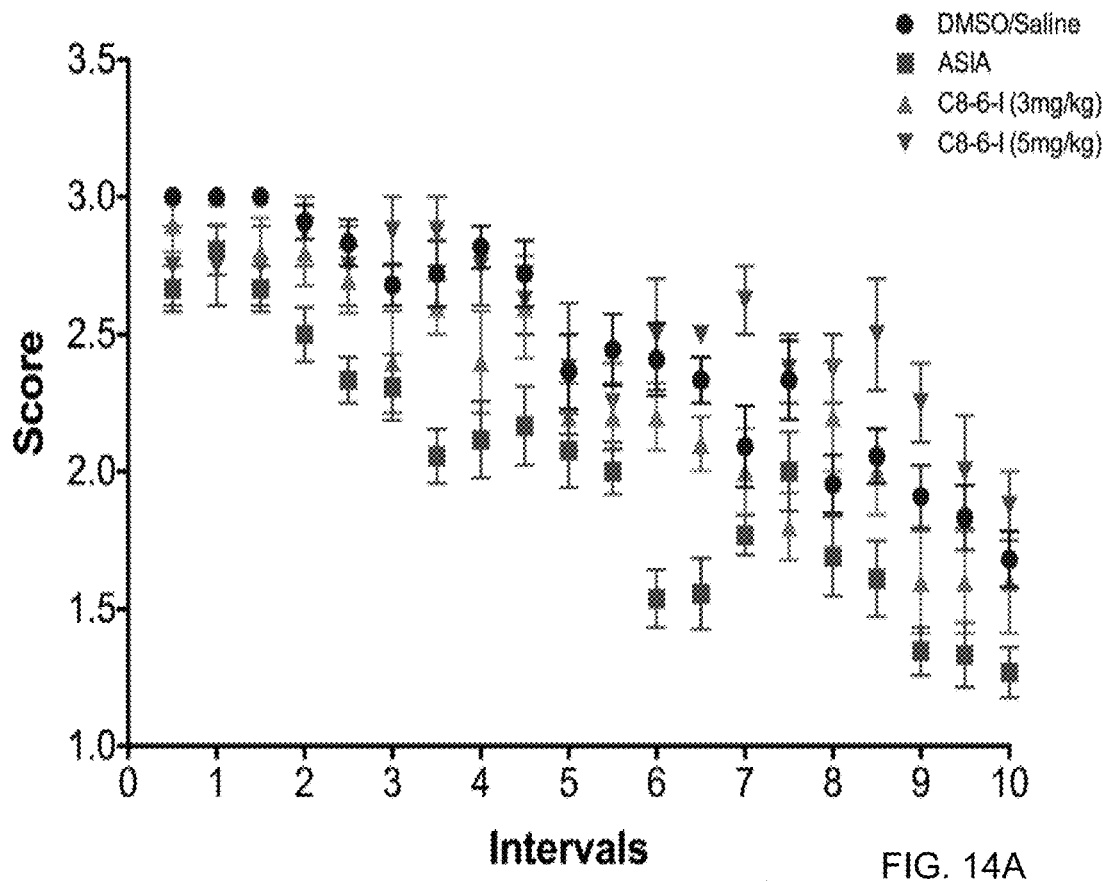
FIGS. 14A, 14B, 14C, 14D and 14E show the results of a forced swim test for the second tested group of rats.
Figure 14B:
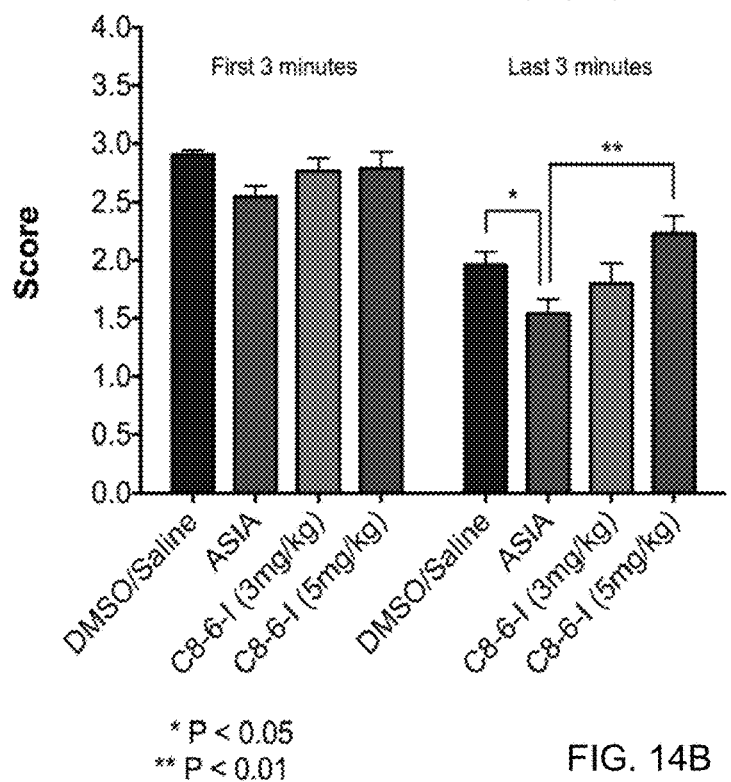

With reference to FIGS. 14A and 14B, assessing the vigor of the treated rats in a forced swim test, in the last three minutes of the test, the rats in the ASIA treated group show decreased vigor compared to the control animals treated with DMSO and saline. Animals treated with ASIA in conjunction with $C_8$-6-I (3) at 3 mg/kg show improved vigor, while animals treated with ASIA in conjunction with $C_8$-6-I (3) at 5 mg/kg show further improved vigor more similar to control animals injected with DMSO and saline.

Figure 14C:
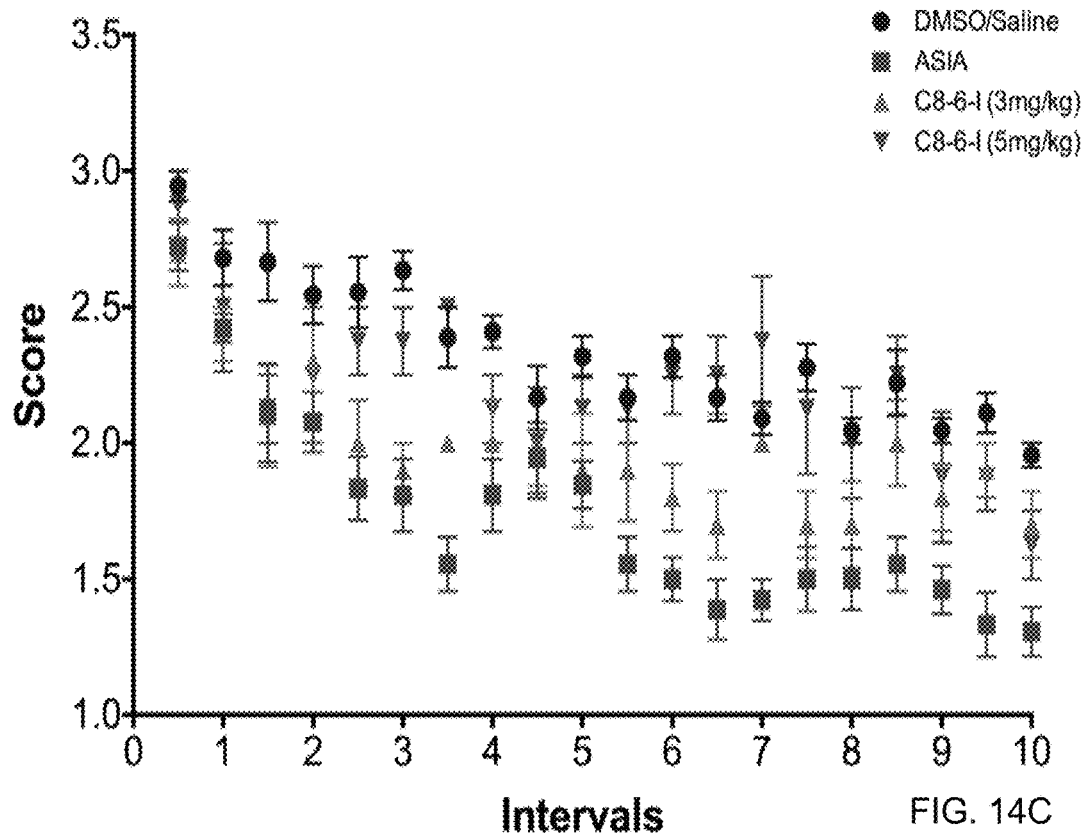
Figure 14D:
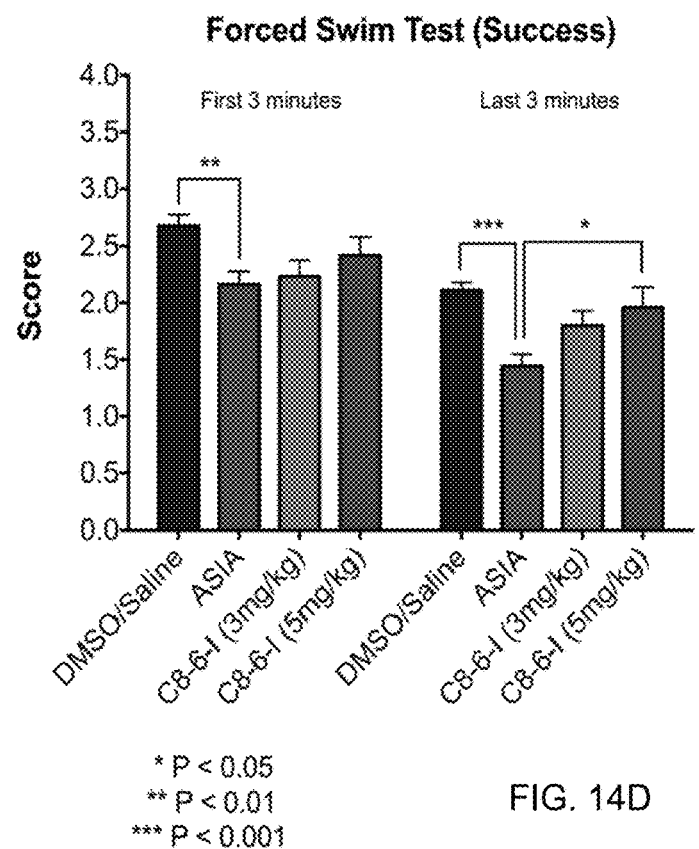

With reference to FIGS. 14C and 14D, assessing the success of the treated rats in a forced swim test, results are similar and again the effects observed are even more significant. In the last three minutes of the test, the rats in the ASIA treated group show decreased success compared to the control animals. Animals treated with ASIA in conjunction with $C_8$-6-I (3) at 3 mg/kg show improved success, while animals treated with ASIA in conjunction with $C_8$-6-I (3) at 5 mg/kg show further improved success more similar to control animals injected with DMSO and saline.

Figure 14E:
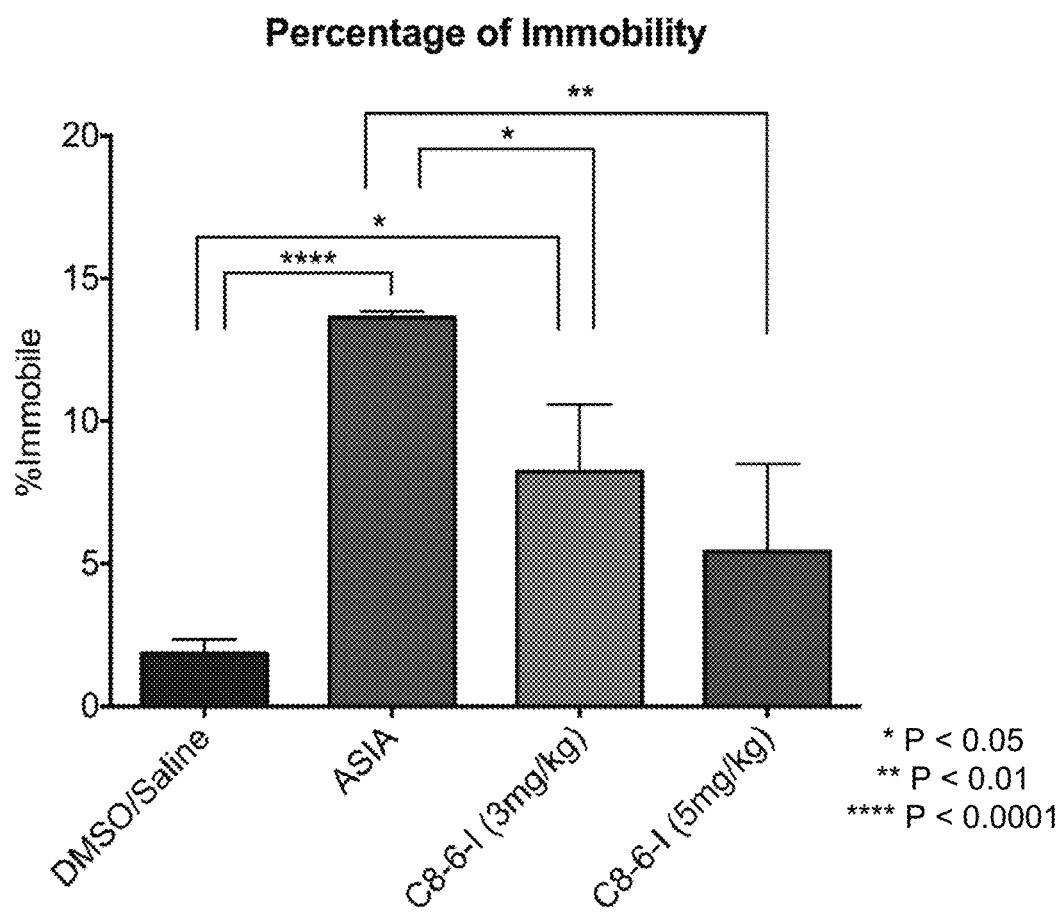

With reference to FIG. 14E, based on videos of the forced swim test, the amount of time that each rat was motionless was calculated as a form of scoring depression for each treatment. Chronic administration of an alpha-synuclein inducing agent (ASIA) significantly increased immobility. The level of immobility was improved by administration of $C_8$-6-I (3) at a dose of 3 mg/kg, and further improved in a dose-dependent manner by administration of $C_8$-6-I (3) at a dose of 5 mg/kg.

The results of this Example demonstrate that the exemplary bifunctional molecule $C_8$-6-I (3) prevents accumulation and/or aggregation of alpha-synuclein in vivo in the substantia nigra of rats in which overexpression of alpha-synuclein has been induced, and improves the motor function of such rats in a dose-dependent manner.

Example 6.0—Conclusions Drawn from Experimental Examples

The inventors have demonstrated that nanopore analysis of binding to alpha-synuclein provides a useful initial screen for studying drug design for Parkinson's Disease. Bifunctional molecules that cause alpha-synuclein to adopt a loop-like conformation (i.e. bifunctional molecules for which alpha-synuclein exhibits a high degree of translocation events when nanopore analysis is carried out) have been shown to be more effective in rescuing yeast from alpha-synuclein induced toxicity in a yeast model for Parkinson's Disease. The inventors have also established that some embodiments of bifunctional molecules are much more effective at preventing alpha-synuclein-induced toxicity in a yeast model for Parkinson's Disease compared to their constituent monomers, administered either alone or in combination. The inventors also determined that for the tested compounds, the binding constants as measured by ITC did not correlate well with the results from the yeast model, which, without being bound by theory, suggests that other factors such as cell permeability or drug metabolism may play an important role in the efficacy of a given compound.

The exemplary bifunctional molecules C8-6-I (3) and $C_8$-6-N (2) were identified from nanopore analysis as the only tested bifunctional molecules that did not cause a more compact conformation of alpha-synuclein at high concentrations. Nanopore analysis of $C_8$-6-I (3) and $C_8$-6-N (2) were consistent with simultaneous binding to both the N- and C-terminus of alpha-synuclein. These two exemplary bifunctional molecules were also the most effective of the tested compounds at rescuing yeast from alpha-synuclein-induced cell death, and prevented the formation of large alpha-synuclein inclusions in the yeast, allowing yeast strain 2AS to grow normally in 5 mM galactose at a concentration of 0.1 micromolar, while alpha-synuclein-GFP became localized to the periphery of the cell. As well, $C_8$-6-I (3) and $C_8$-6-N (2) were also able to cause the dissolution of preformed foci of alpha-synuclein-GFP and as such are potential drug leads for preventing the progression of Parkinson's Disease by prion-like mechanisms. On the other hand, binding constants as measured by ITC were only of the order of $10^5$ $M^{-1}$, which is lower than most of the other tested bifunctional molecules. Without being bound by theory, this suggests that other factors beyond simple binding affinity may influence the mechanism by which the bifunctional molecules allow cell growth in the presence of high concentrations of alpha-synuclein.

Based on the fact that certain bifunctional molecules prevented and even rescued yeast from alpha-synuclein induced toxicity, and prevented, delayed or reversed aggregation of alpha-synuclein, in a yeast model for Parkinson's Disease and the known role of the aggregation of alpha-synuclein in Parkinson's disease, it can be soundly predicted that such compounds may have potential utility as therapeutic agents to prevent, delay or reverse the effects of Parkinson's Disease in mammals, including humans, and/or that such compounds provide lead compounds for the development of such therapeutic agents. This is confirmed by the fact that in vivo testing of the bifunctional molecule $C_8$-6-I (3) in rats that overexpress alpha-synuclein showed that administration of $C_8$-6-I (3) reduces accumulation and/or aggregation of alpha-synuclein in the substantia nigra of the rats at two tested doses, and further enhances the vigor and success of the rats in a forced swim test in a dose-dependent manner.

The experiments conducted by the inventors also demonstrate that all of the tested compounds bind to alpha-synuclein, in some cases with very high affinity. Bifunctional molecules that bind to alpha-synuclein, and in particular bifunctional molecules that bind to alpha-synuclein with high affinity, may have utility as imaging agents, for example if they are suitably labeled for use in PET scanning.

Example 7.0—Prospective Example—Use of Bifunctional Molecules in PET Scanning

Bifunctional molecules will be labelled with $^{18}$F or $^{1}$C and injected into mice. Tissue distribution will be assessed, notably in the brain and substantia nigra which has the highest concentration of alpha-synuclein. In most patients, by the time clinical symptoms appear, much of the substantia nigra has been destroyed and the disease is irreversible, so early detection is advantageous.

A mouse model of Parkinson's Disease will also be used to study changes in alpha-synuclein distribution with time, which will allow better diagnostic evaluation of PET scanning images taken from subjects believed to be at risk of developing or of having Parkinson's Disease by showing how progression of the disease affects alpha-synuclein distribution.

Synthesis of $^{18}$F-labelled drugs and PET scanning will be performed at the new cyclotron facility at the University of Saskatchewan. Late-stage fluorine incorporation into bifunctional molecules will be optimised. For example, fluoride displacement of a $CH_2$—O-tosyl will be used to produce a $CH_2F$ group on a $C_8$ linked caffeine dimer. Initially the work will show if the bifunctional molecules cross the blood-brain barrier and do not accumulate in other tissues. PET probes of several different bifunctional molecules will be prepared to begin optimisation for brain uptake.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole. While the anticipated or hoped-for utility of certain embodiments has been discussed above, no promise of any utility greater than that explicitly set forth herein should be inferred from this disclosure, and any promise of utility should be assessed independently for each embodiment and each claim set forth herein.

Without limitation, some aspects of the invention include the following:
1. A bifunctional molecule comprising the general structure A-L-B, wherein A and B are alpha-synuclein binding agents (optionally the same alpha-synuclein binding agent) and L is a linker.
2. A bifunctional molecule as defined in aspect 1, wherein the first alpha-synuclein binding agent and the second alpha-synuclein binding agent are the same, so that the bifunctional molecule comprises a dimer.
3. A bifunctional molecule as defined in aspect 1, wherein the first alpha-synuclein binding agent and the second alpha synuclein binding agent are different, so that the bifunctional molecule comprises a chimera.
4. A bifunctional molecule as defined in any one of the preceding aspects or anywhere in this specification, wherein the linker comprises an alkyl, alkenyl or alkynl linker.
5. A bifunctional molecule as defined in any one of the preceding aspects or anywhere in this specification, wherein the linker is halogenated, comprises an aryl group, comprises a cyclic carbon chain, and/or contains one or more heteroatoms.
6. A bifunctional molecule comprising a first alpha-synuclein binding agent and a second alpha-synuclein binding agent covalently joined by a linker, wherein the bifunctional molecule binds to alpha-synuclein and causes the alpha-synuclein to adopt a loop-like conformation, and wherein the loop-like conformation of the alpha-synuclein is optionally established if nanopore analysis indicates a major translocation peak at between −40 pA and −80 pA, wherein optionally at least 70% of the events detected by nanopore analysis comprise translocation events, and wherein optionally the nanopore analysis is conducted with a concentration of 1 micromolar alpha-synuclein and 20 micromolar bifunctional molecule.
7. A method of conducting PET scanning comprising using a bifunctional molecule as defined in any one of the preceding aspects as an imaging agent.
8. A method of conducting PET scanning comprising:
    administering a labelled bifunctional molecule as defined in any one of the preceding aspects or as described in this specification to a subject as an imaging agent;
    evaluating the distribution of alpha-synuclein in the subject's brain, including optionally evaluating the distribution of alpha-synuclein in the substantia nigra;
    comparing the distribution of alpha-synuclein in the subject's brain and/or the subject's substantia nigra to a distribution of alpha-synuclein in the brain and/or the substantia nigra of a control subject known to have or known to have developed Parkinson's Disease; and
    if the distribution of alpha-synuclein in the subject's brain and/or the subject's substantia nigra is similar to the distribution of alpha-synuclein in the control subject's brain and/or the subject's substantia nigra, concluding that the subject has or has an increased likelihood of developing Parkinson's Disease.
9. A method as defined in any one of the preceding aspects, wherein the bifunctional molecule is labelled with $^{18}$F, $^{11}$C, $^{13}$N or $^{15}$O.
10. A method of preventing or delaying the aggregation of alpha-synuclein, comprising administering to a mammal a bifunctional molecule as defined in any one of the preceding aspects or anywhere in this specification.
11. A method of preventing, delaying or slowing the onset of Parkinson's disease, comprising administering to a mammal a bifunctional molecule as defined in any one of the preceding aspects or anywhere in this specification.
12. A method as defined in any one of the preceding aspects, wherein the mammal comprises a human.

REFERENCES

The following references may be of interest with respect to the subject matter described herein. Each of the following references is incorporated by reference herein for all purposes.
(1) Samii, A., Nutt, J. G., and Ransom, B. R. (2004) Parkinson's disease. *Lancet* 363, 1783-1789.
(2) Davie, C. A. (2008) A review of Parkinson's disease. *Br. Med. Bull.* 86, 109-127.
(3) Forno, L. S. (1996) Neuropathology of Parkinson's disease. *J. Neuropathol. Exp. Neurol.* 55, 259-272.
(4) Uversky, V. N. (2008) Alpha-synuclein misfolding and neurodegenerative diseases. *Curr. Protein Pept. Sci.* 9, 507-540.

(5) Georgieva, E. R., Ramlall, T. F., Borbat, P. P., Freed, J. H., and Eliezer, D. (2010). The Lipid-binding Domain of Wild Type and Mutant α-Synuclein: Compactness and interconversion between the broken and extended helix forms. *J. Biol. Chem.* 285, 28261-28274.

(6) Lotharius, J., and Brundin, P. (2002). Pathogenesis of Parkinson's disease: dopamine, vesicles and [alpha]-synuclein. *Nat. Rev. Neurosci.* 3, 932-942.

(7) Lashuel, H. A., Overk, C. R., Oueslati, A., and Masliah, E. (2013). The many faces of [alpha]-synuclein: from structure and toxicity to therapeutic target. *Nat. Rev. Neurosci.* 14, 38-48.

(8) Burré, J., Sharma, M., and Sudhof, T. C. (2012). Systematic Mutagenesis of α-Synuclein Reveals Distinct Sequence Requirements for Physiological and Pathological Activities. *J. Neurosci.* 32, 15227-15242.

(9) Fink, A. L. (2006). The Aggregation and Fibrillation of α-Synuclein. *Acc. Chem. Res.* 39, 628-634.

(10) Binolfi, A., Quintanar, L., Bertoncini, C. W., Griesinger, C., and Fernández, C. O. (2012). Bioinorganic chemistry of copper coordination to alpha-synuclein: Relevance to Parkinson's disease. *Coord. Chem. Rev.* 256, 2188-2201.

(11) Tavassoly, O., Nokhrin, S., Dmitriev, O. Y., and Lee, J. S., (2014) Cu(II) and dopamine bind to alpha-Synuclein and cause large conformational changes, *FEBS J.* 281, 2738-2753

(12) Grosset, D. G., Grosset, K. A., Okun, M. S., and Fernandez, H. H. (2009). Drug treatment of Parkinson's disease. In Parkinson's Disease: Clinician's Desk Reference, Grosset, D. G., Grosset, K. A., Okun, M. S., and Fernandez, H. H., eds. (London: Manson Publishing Ltd), pp. 59-68.

(13) Shulman, J. M., De Jager, P. L., and Feany, M. B. (2011). Parkinson's Disease: Genetics and Pathogenesis. *Annu, Rev. Pathol.* 6, 193-222.

(14) Kraus, A., Groveman, B. R., and Caughey, B. (2013) Prions and the potential transmissability of protein misfolding diseases. *Annu. Rev. Microbiol.* 67, 543-564 (15) Luk, K. C., Kehm, V., Carroll, J., Zhang, B., O'Brien, P., Trojanowski, J. Q., and Lee, V. M.-Y. (2012) Pathological α-synuclein transmission initiates Parkinson-like neurodegeneration in nontransgenic mice. *Science* 338, 949-953.

(16) Jucker, M., and Walker, L. C. (2013) Self-propagation of pathogenic protein aggregates in neurodegenerative diseases. *Nature* 501, 45-51.

(17) Prusiner, S. B. (2012) A unifying role for prions in neurodegenerative diseases. *Science* 336, 1511-1513.

(18) Klein, C., and Westenberger, A. (2012) Genetics of Parkinson's Disease. *Cold Spring Harb. Perspect. Med.* 2:a008888, 1-15.

(19) Feany, M. B., and Pallanck, L. J. (2003) Parkin: A Multipurpose Neuroprotective Agent? *Neuron* 38, 13-16.

(20) Youle, R. J., and Nerendra, D. P. (2011) Mechanisms of Mitophagy. *Nat. Rev. Mol. Cell Biol.* 12, 9-14.

(21) Kakish, J., Lee, D., and Lee, J. S. (2015) Drugs that bind to alpha-synuclein: Neuroprotective or neurotoxic? *ACS Chem. Neurosci.* 6, 1930-1940.

(22) Kamel, F. (2013) Paths from pesticides to Parkinson's. *Science* 341, 722-723

(23) Wang, A., Costello, S., Cockburn, M., Zhang, X., Bronstein, J., and Ritz, B. (2011) Parkinson's risk from ambient exposure to pesticides. *Eur. J. Epidemiol.* 26, 547-555.

(24) Kuter, K., Nowak, P., Golembiowska, K., and Ossowska, K. (2010) Increased reactive oxygen species production in the brain after repeated low-dose pesticide paraquat exposure in rats. A comparison with peripheral tissues. *Neurochem. Res.* 35, 1121-1130.

(25) Postuma, R. B., Lang, A. E., Munhoz, R. P., Charland, K., Pelletier, A., Moscovich, M., Filla, L., Zanatta, D., Romenets, S. R., Altman, R., and Chuang, R., (2012) Caffeine for treatment of Parkinson disease: A randomized controlled trial. *Neurobiology,* 79, 651-658.

(26) Prediger, R. D. (2010) Effects of caffeine in Parkinson's disease: from neuroprotection to the management of motor and non-motor symptoms. *J Alzheimers Dis.* 20, 205-220.

(27) Ross, G. W., and Petrovitch, H. (2001) Current evidence for neuroprotective effects of nicotine and caffeine against Parkinson's disease. *Drugs Aging,* 18, 797-806.

(28) Quik, M., Perez, X. A., and Bordia, T. (2012) Nicotine as a potential neuroprotective agent for Parkinson's disease. *Mov. Disord.* 27, 947-957.

(29) Quik, M. (2004) Smoking, nicotine and Parkinson's disease. *Trends Neurosci.* 27, 561-568.

(30) Patil, S. P., Jain, P. D., Ghumatkar, P. J., Tambe, R., and Sathaye, S. (2014) Neuroprotective effect of metformin in MPTP-induced Parkinson's disease in mice. *Neurosci,* 277, 747-754.

(31) Wahlqvist, M. L., Lee, M-S., Hsu, C-C., Chuang, S-Y., Lee, J-T., and Tsai, H-N. (2012) Metformin-inclusive sulfonylurea therapy reduces the risk of Parkinson's disease occurring with Type 2 diabetes in a Taiwanese population cohort. *Park. Rel. Dis.* 18, 753-758.

(32) Dimpfel, W., and Hoffmann, J. A. (2011) Effects of rasagiline, its metabolite aminoindan and selegiline on glutamate receptor mediated signaling in the rat hippocampus slice in vitro. *BMC Pharmacology* 11, 1-10.

(33) Bar Am, O., Amit, T., and Youdim, M. B. H. (2004) Contrasting neuroprotective and neurotoxic actions of respective metabolites of anti-Parkinson drugs rasagiline and selegiline. *Neurosci. Lett.* 355, 169-172.

(34) Chau, K. Y., Cooper, J. M., and Schapira, A. H. V. (2010) Rasagiline protects against alpha-synuclein induced sensitivity to oxidative stress in dopaminergic cells. *Neurochem. Int.* 57, 525-529.

(35) Bar-Am, O., Weinreb, O., Amit, T., and Youdim, M. B. H. (2010) The neuroprotective mechanism of 1-[R]-aminoindan, the major metabolite of the anti-parkinsonian drug rasagiline. *J. Neurochem.* 112, 1131-1137.

(36) Curtin, K., Fleckenstein, A. E., Robison, R. J., Crookston, M. J., Smith, K. R. and Hanson, G. R. (2015) Methamphetamine/amphetamine abuse and risk of Parkinson's disease in Utah: a population-based assessment. *Drug Alcohol Depend.* 120, 35-40.

(37) Callaghan, R. C., Cunningham, J. K., Sykes, J., and Kish, S. J. (2012) Increased risk of Parkinson's disease in individuals hospitalized with conditions related to the use of methamphetamine or other amphetamine-type drugs. *Drug Alcohol Depend.* 146, 30-38.

(38) Games, D., Valera, E., Spencer, B., Rockenstein, E., Mante, M., Adame, A., Patrick, C., Ubhi, K., Nuber, S., Sacayon, P., Zago, W., Seubert, P., Barbour, R., Schenk, D., and Masliah, E. (2014). Reducing C-Terminal-Truncated Alpha-Synuclein by Immunotherapy Attenuates Neurodegeneration and Propagation in Parkinson's Disease-Like Models. *J. Neurosci.* 34, 9441-9454.

(39) Dufty, B., Warner, L., Hou, S., Jiang, S., Gomez-Isla, T., Leenhouts, K., Oxford, J., Feany, M., Masliah, E., and Rohn, T. (2007). Calpain-Cleavage of α-Synuclein: Connecting Proteolytic Processing to Disease-Linked Aggregation. *Am. J. Pathol.* 170, 1725-1738.

(40) Tavassoly, O., Kakish, J., Nokhrin, S., Dmitriev, O., and Lee, J. (2014). The use of nanopore analysis for discovering drugs which bind to alpha-synuclein for the treatment of Parkinson's disease. *Eur. J. Med.* 88, 44-52.

(41) Stefureac, R., Long, Y. T., Kraatz, H. B., Howard, P. and Lee, J. S. (2006) Transport of alpha-helical peptides through alpha-hemolysin and aerolysin pores. *Biochemistry* 45, 9172-9179.

(42) Madampage, C., Tavassoly, O., Christensen, C., Kumari, M. and Lee, J. S. (2012) Nanopore analysis: An emerging technique for studying the folding and misfolding of proteins. *Prion* 6, 116-123.

(43) Hu, R., Diao, J., Li, J., Tang, Z., Li, X., Leitz, J., Long, J., Liu, J., Yu, D., and Zhao, Q. (2016) Intrinsic and membrane-facilitated a-synuclein oligomerization revealed by label-free detection through solid-state nanopores. *Sci. Rep.* 6, 1-11.

(44) Movileanu, L., Schmittschmitt, J. P., Scholtz, J. M. and Bayley, H. (2005) Interactions of peptides with a protein pore. *Biophys. J.* 89, 1030-45.

(45) Zhao, Q., Jayawardhana, D. A., Wang, D. and Guan, X. (2009) Study of peptide transport through engineered protein channels. *J. Phys. Chem. B* 113, 3572-8.

(46) Stefureac, R. I. and Lee, J. S. (2008) Nanopore analysis of the folding of zinc fingers. *Small* 4, 1646-50.

(47) Tardiff, L., Jui, N. T., Khurana, V., Tambe, M. A., Thompson, M. L., Chung, C. Y., Kamadurai, H. B., Kim, H. T., Lancaster, A. K., Caldwell, K. A., Caldwell, G. A., Rochet, J-C., Buchwald, S. L. and Lindquist, S. (2013) Yeast reveal a druggable Rsp/Nedd4 network that ameliorates alpha-synuclein toxicity. *Science* 342, 979-983.

(48) Su, L. J., Auluck, P. K., Outeiro, T. F., Yeger-Lotem, E., Kritzer, J. A., Tardiff, D. F., Strathearn, K. E., Liu, F., Cao, S., Hamamichi, S., Hill, K. J., Caldwell, K. A., Bell, G. W., Fraenkel, E., Cooper, A. A., Caldwell, G. A., McCaffery, J. M., Rochet, J. C., and Lindquist, S. (2010) Compounds from an unbiased chemical screen reverse both ER-to-Golgi trafficking defects and mitochondrial dysfunction in Parkinson's disease models. *Dis. Model Mech.* 3, 194-208.

(49) Khurana, V., and Lindquist, S. (2010) Modeling neurodegeneration in *Saccharomyces cerevisiae*. Why cook with baker's yeast? *Nat. Rev. Neurosci.* 11, 436-449.

(50) Le Quement, S. T., Nielsen, T. E., and Meldal, M. (2007) Scaffold Diversity through Intramolecular Cascade Reactions of Solid-Supported Cyclic N-Acyliminium Intermediates. *J. Comb. Chem.* 9 (6), 1060-1072.

(51) Kalla, R. V., Elzein, E., Perry, T., Li, X., Palle, V., Varkhedkar, V., Gimbel, A., Maa, T., Zeng, D., and Zablocki, J. (2006) Novel 1,3-Disubstituted 8-(1-benzyl-1H-pyrazol-4-yl) Xanthines: High Affinity and Selective A2B Adenosine Receptor Antagonists. *J. Med. Chem.* 49, 3682-3692.

(52) Turner, E. L., Malo, M. E., Pisclevich, M. G., Dash, M. D., Davies, G. F., Arnason, T. G., and Harkness, T. A. (2010) The *Saccharomyces cerevisiae* anaphase promoting complex interacts with multiple histone modifying enzymes to regulate cell cycle progression. *Eukaryot. Cell* 9, 1418-1431.

(53) Ghavidel, A., Baxi, K., Ignatchenko, V., Prusinkiewics, M., Arnason, T. G., Kislinger, T., Carvalho, C. E., and Harkness, T. A. (2015) A genome scale screen for mutants with delayed exit from mitosis: Ire1-independent induction of autophagy integrates ER homeostasis into mitotic lifespan. *PloS Genet.* 11, e1005429.

(54) Kakish, J., Tavassoly, O., and Lee, J. S. (2015). Rasagiline, a suicide inhibitor of MAO-B, binds to alpha-synuclein. *ACS Chem. Neurosci.* 6, 347-355.

(55) Outeiro T F, Lindquist S (2003) Yeast cells provide insight into alpha-synuclein biology and pathobiology. *Science* 302, 1772-1775.

(56) Le Quement, S. T.; Nielsen, T. E.; Meldal, M., Scaffold Diversity through Intramolecular Cascade Reactions of Solid-Supported Cyclic N-Acyliminium Intermediates. *Journal of Combinatorial Chemistry* 2007, 9 (6), 1060-1072.

(57) Kalla, R. V.; Elzein, E.; Perry, T.; Li, X.; Palle, V.; Varkhedkar, V.; Gimbel, A.; Maa, T.; Zeng, D.; Zablocki, J., Novel 1,3-Disubstituted 8-(1-benzyl-1H-pyrazol-4-yl) Xanthines: High Affinity and Selective A2B Adenosine Receptor Antagonists. *Journal of Medicinal Chemistry* 2006, 49 (12), 3682-3692.

(58) Chu, W.; Zhou, D.; Gaba, V.; Liu, J.; Li, S.; Peng, X.; Xu, J.; Dhavale, D.; Bagchi, D. P.; d'Avignon, A.; Shakerdge, N. B.; Bacskai, B. J.; Tu, Z.; Kotzbauer, P. T.; Mach, R. H., Design, Synthesis, and Characterization of 3-(Benzylidene)indolin-2-one Derivatives as Ligands for alpha-Synuclein Fibrils. *Journal of Medicinal Chemistry* 2015, 58 (15), 6002-6017.

(59) Abelaira, H. M., G. Z. Réus, J. Quevedo, Animal Models as Tools to Study the Pathophysiology of Depression. *Revista Brasileira de Psiquiatria,* 2013, 35(Suppl. 2), pp. S112-S120.

The invention claimed is:

1. A bifunctional molecule comprising a first alpha-synuclein binding agent covalently linked to a second alpha-synuclein binding agent by a linker, comprising one of the following structures (II) or (III):

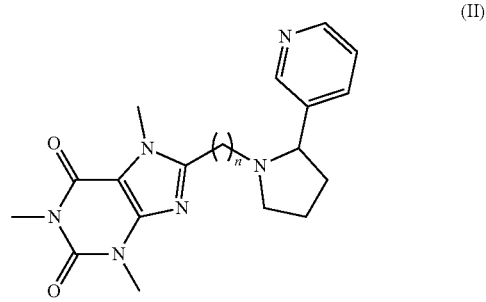

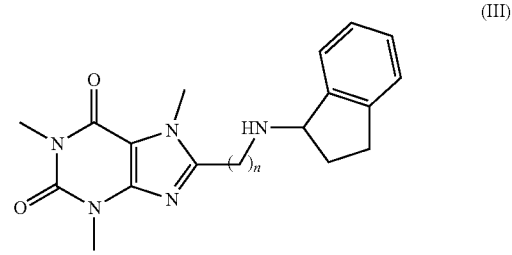

wherein n is an integer between 1 and 10 carbon atoms that defines a linker, wherein the linker is a saturated or unsaturated alkyl linker.

2. A bifunctional molecule as defined in claim 1 comprising one of the following structures (II) or (III):

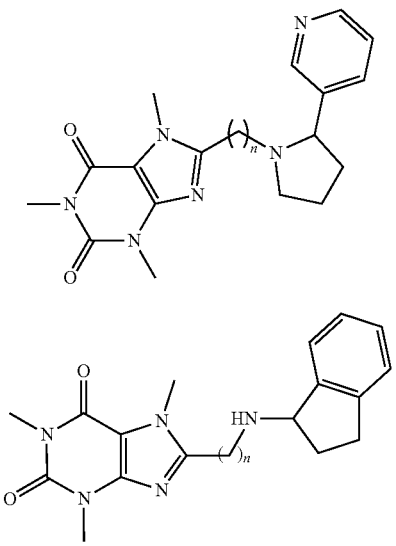

(II)

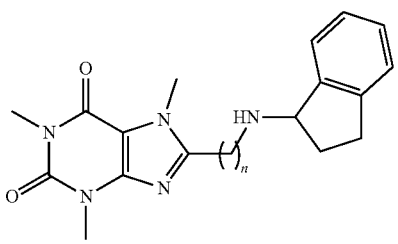

(III)

wherein n is 5, 6 or 7.

3. A bifunctional molecule as defined in claim 1 comprising one of the following structures:

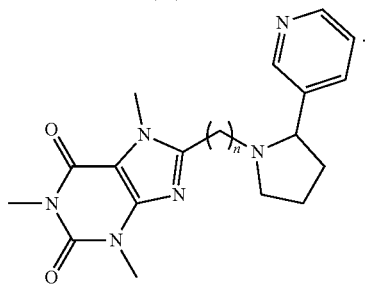

(11) n = 4
(3) n = 6
(12) n = 8

(22) n = 4
(2) n = 6
(23) n = 8

4. A bifunctional molecule as defined in claim 3, comprising one of the following structures:

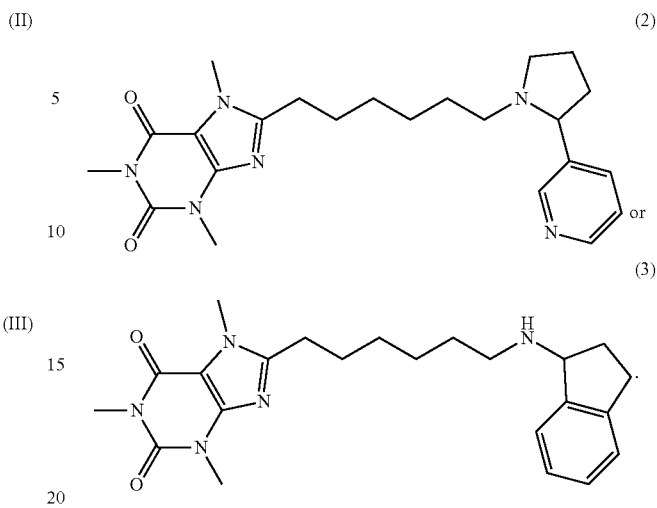

(2)

or (3)

5. A bifunctional molecule as defined in claim 1, wherein the bifunctional molecule binds to alpha-synuclein and causes the alpha-synuclein to adopt a loop-like conformation, wherein optionally the loop-like conformation of the alpha-synuclein is established if nanopore analysis indicates a major translocation peak at between −40 pA and −80 pA and at least 70% of the events detected by nanopore analysis comprise translocation events.

6. A method comprising using a bifunctional molecule as defined in claim 1 as an imaging agent.

7. A method as defined in claim 6 to conduct PET scanning comprising:
administering a labelled bifunctional molecule as defined in claim 1 to a subject as an imaging agent;
evaluating the distribution of alpha-synuclein in the subject's brain;
comparing the distribution of alpha-synuclein in the subject's brain to a distribution of alpha-synuclein in the brain of a control subject known to have or known to have developed Parkinson's Disease; and
if the distribution of alpha-synuclein in the subject's brain is similar to the distribution of alpha-synuclein in the control subject's brain, concluding that the subject has or has an increased likelihood of developing Parkinson's Disease.

8. A kit for diagnosing or detecting Parkinson's Disease or a likelihood of developing Parkinson's Disease by PET scanning, the kit comprising a bifunctional molecule as defined in claim 1, wherein the bifunctional molecule is labelled with $^{18}$F, $^{11}$C, $^{13}$N or $^{15}$O.

9. A method of using a bifunctional molecule as defined in claim 1 to prevent or delay the aggregation of alpha-synuclein in a mammalian subject, the method comprising administering a therapeutically effective amount of the bifunctional molecule to the subject.

* * * * *